US012624091B2

(12) United States Patent (10) Patent No.: US 12,624,091 B2
Pilewski et al. (45) Date of Patent: May 12, 2026

(54) HIV/HCV CROSS-REACTIVE ANTIBODIES AND USES THEREOF

(71) Applicant: VANDERBILT UNIVERSITY, Nashville, TN (US)

(72) Inventors: Kelsey Pilewski, Nashville, TN (US); Ivelin Stefanov Georgiev, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 1102 days.

(21) Appl. No.: 17/600,893

(22) PCT Filed: Apr. 3, 2020

(86) PCT No.: PCT/US2020/026552
§ 371 (c)(1),
(2) Date: Oct. 1, 2021

(87) PCT Pub. No.: WO2020/206232
PCT Pub. Date: Oct. 8, 2020

(65) Prior Publication Data
US 2022/0185870 A1 Jun. 16, 2022

Related U.S. Application Data

(60) Provisional application No. 62/971,477, filed on Feb. 7, 2020, provisional application No. 62/829,526, filed on Apr. 4, 2019.

(51) Int. Cl.
C07K 16/10 (2006.01)

(52) U.S. Cl.
CPC ........ C07K 16/1045 (2013.01); C07K 16/109 (2013.01); *C07K 2317/33* (2013.01)

(58) Field of Classification Search
CPC .............. C07K 16/1045; C07K 16/109; C07K 2317/33
See application file for complete search history.

(56) References Cited

U.S. PATENT DOCUMENTS

| | | | |
|---|---|---|---|
| 4,342,566 A | 8/1982 | Dixon et al. | |
| 5,804,440 A | 9/1998 | Barbas et al. | |
| 6,096,441 A | 8/2000 | Hauser et al. | |
| 2004/0110933 A1 | 6/2004 | Rondon et al. | |
| 2015/0191739 A1 | 7/2015 | La Rosa et al. | |
| 2017/0088620 A1* | 3/2017 | Nioi | C07K 16/2851 |
| 2017/0355756 A1* | 12/2017 | Julien | C07K 16/18 |
| 2018/0282400 A1 | 10/2018 | Mouquet et al. | |

FOREIGN PATENT DOCUMENTS

| | | | |
|---|---|---|---|
| WO | 94/04678 | 3/1994 | |
| WO | 94/29348 | 12/1994 | |
| WO | 2001032893 A1 | 5/2001 | |
| WO | WO-2008068048 A2 * | 6/2008 | .............. A61P 31/10 |
| WO | 2014065822 A1 | 5/2014 | |
| WO | 2018125813 A1 | 7/2018 | |
| WO | 2019/143884 | 7/2019 | |
| WO | 2020033164 | 2/2020 | |

OTHER PUBLICATIONS

Hwang, Kwan-Ki, et al. "IGHV 1-69 B Cell Chronic Lymphocytic Leukemia Antibodies Cross-React with HIV-1 and Hepatitis C Virus Antigens as Well as Intestinal Commensal Bacteria." PloS one 9(3) (2014): e90725. (Year: 2014).*
Chiu, Mark L., et al. "Antibody structure and function: the basis for engineering therapeutics." Antibodies 8(4) (2019): 55. (Year: 2019).*
Rudikoff, Stuart, et al. "Single amino acid substitution altering antigen-binding specificity." Proceedings of the National Academy of Sciences 79(6) (1982): 1979-1983. (Year: 1982).*
Sela-Culang, Inbal, Vered Kunik, and Yanay Ofran. "The structural basis of antibody-antigen recognition." Frontiers in immunology 4 (2013): 302. (Year: 2013).*
International Search Report and Written Opinion dated Aug. 18, 2020, from International Application No. PCT/US2020/026552, 11 pages.
Bailey, Jr et al. "Broadly neutralizing antibodies with few somatic mutations and hepatitis C virus clearance", JCI Insight, 2017;2(9), 17 pages.
Georgiev, Is et al. "Delineating Antibody Recognition in Polyclonal Sera from Patterns of HIV-1 Isolate Neutralization", Science, vol. 340, May 10, 2013, pp. 751-756.
Kohler and Milstein, Nature, 256:495 (1975).
Needleman et al. (1970) J. Mol. Biol. 48: 443-453.
Zoller, M.J. Curr. Opin. Biotechnol. 3:348-354, (1992).
Zabat E.A. et al., (1991) Sequences of proteins of immunological interest. NIH Publication 91-3242.
Al-Lazikani et al., 1997. J. Mol. Biol., 273:927-948.
MacCallum et al., 1996, J. Mol. Biol, 262:732-745.
Lefranc et al., Dev. Comp. Immunol., 2003, 27:55-77.
Honegger and Plückthun, J. Mol. Biol., 2001, 309:657-70.
International Preliminary Report on Patentability issued for Application No. PCT/US2020/026552, dated dated Oct. 14, 2021.
Anonymous. Third Party Observation in connection with International Application No. PCT/US2020/026552. Submitted Aug. 4, 2021.
Burgess Stg et al. A multiplexed protein microarray for the simultaneous serodiagnosis of human immunodeficiency virus/hepatitis C virus infection and typing of whole blood. Analytical Biochemistry. 382(1): 9-15(Nov. 1, 2008).
Chen F et al. VH1-69 antiviral broadly neutralizing antibodies: genetics, structures, and relevance to rational vaccine design. Current opinion in Virology. 34:149-159(Mar. 16, 2019).

(Continued)

*Primary Examiner* — Julie Wu
*Assistant Examiner* — Bryan William Heck
(74) *Attorney, Agent, or Firm* — Meunier Carlin & Curfman LLC

(57) ABSTRACT

The present disclosure relates to antibodies and uses thereof for treating an HIV infection, an HCV infection, or an HIV/HCV co-infection.

19 Claims, 81 Drawing Sheets
(71 of 81 Drawing Sheet(s) Filed in Color)
Specification includes a Sequence Listing.

(56)                   References Cited

OTHER PUBLICATIONS

Leem J. Thesis on: Development of computational methodologies for antibody design. St Anne's College University of Oxford (2016).

Partial Supplementary European Search Report Communication pursuant to Rule 164(1) EPC, issued in connection with European Patent Application No. 20785367.2. May 12, 2023.

Pilewski K et al. Antibody cross-reactivity in chronic HIV/HCV co-infection. The Journal of Immunology. 2021 (1_Suppl):72.7-72. 7, XP093042811(May 1, 2019).

Warter L et al. Human poly- and cross-reactive anti-viral antibodies and their impact on protection and pathology. Immunologic Research. 53(1): 148-161(Mar. 21, 2012).

* cited by examiner

| Antigen name | Virus | Strain/Clade | Native function |
|---|---|---|---|
| BG505.SOSIP | HIV | A | Cell entry |
| B41.SOSIP | HIV | B | Cell entry |
| ConC gp120 | HIV | C | Cell entry |
| AE.A244 gp120 | HIV | AE | Cell entry |
| JFH-1 E2core | HCV | JFH1 (genotype 2a) | Cell entry |
| H77 E2core | HCV | H77 (genotype 1a) | Cell entry |
| H77 E1E2 | HCV | H77 (genotype 1a) | Cell entry |

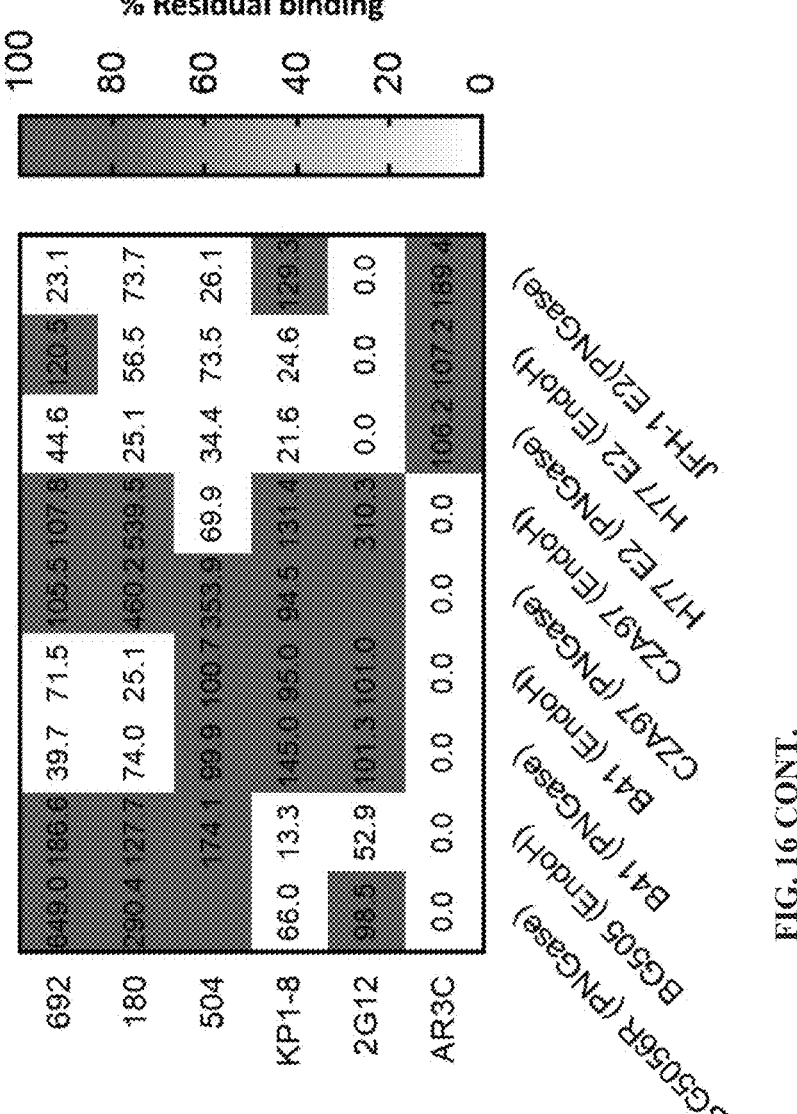
FIG. 16 CONT.
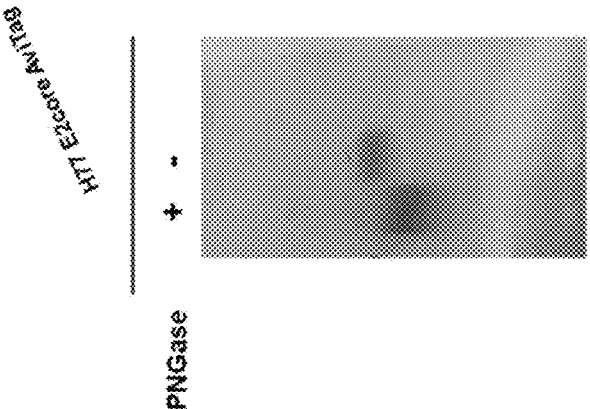

BG505 gp140 (SOSIP)

PDB: 4ZMJ

H77 E2core

PDB: 4MWF.D

Polyreactivity mAb

Joe Balsomo, Bachmann group

| PID | Sex | Yr of Infection | Infection Status | Secondary Infection | HIV Medication |
|-----|-----|-----------------|------------------|---------------------|----------------|
| ci10014 | M | 2003 | Chronic | HepC | NA |

HCV infection?

Blood draw 09/25/2003

Blood draw 11/03/2005

HIV infection 2003

Blood draw 10/14/2004

Blood draw 03/21/2006

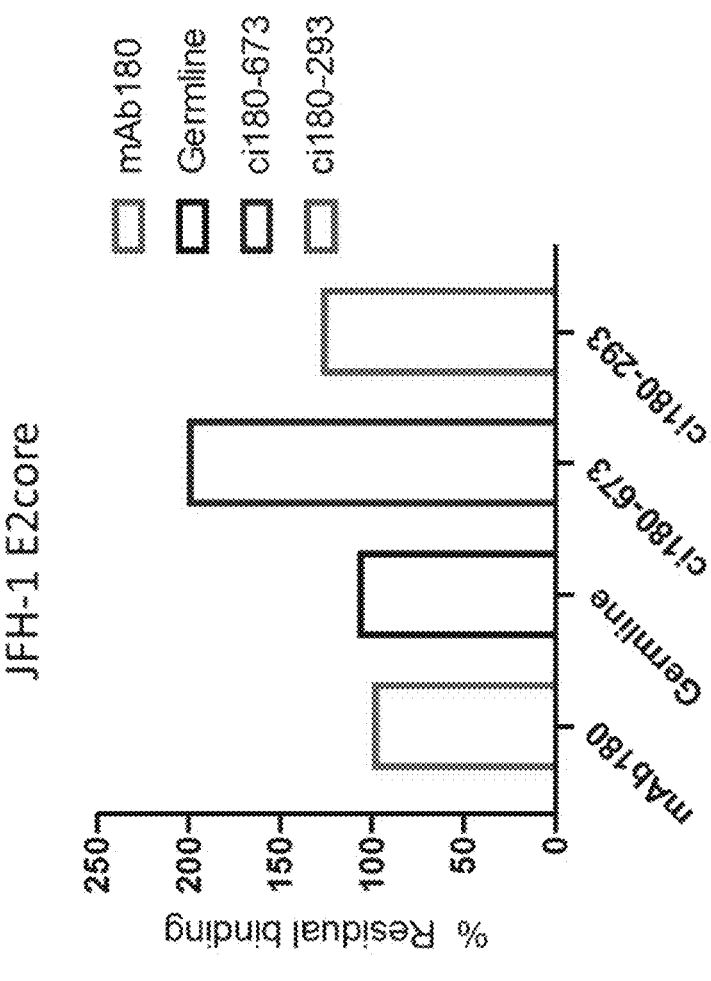
FIG. 31B
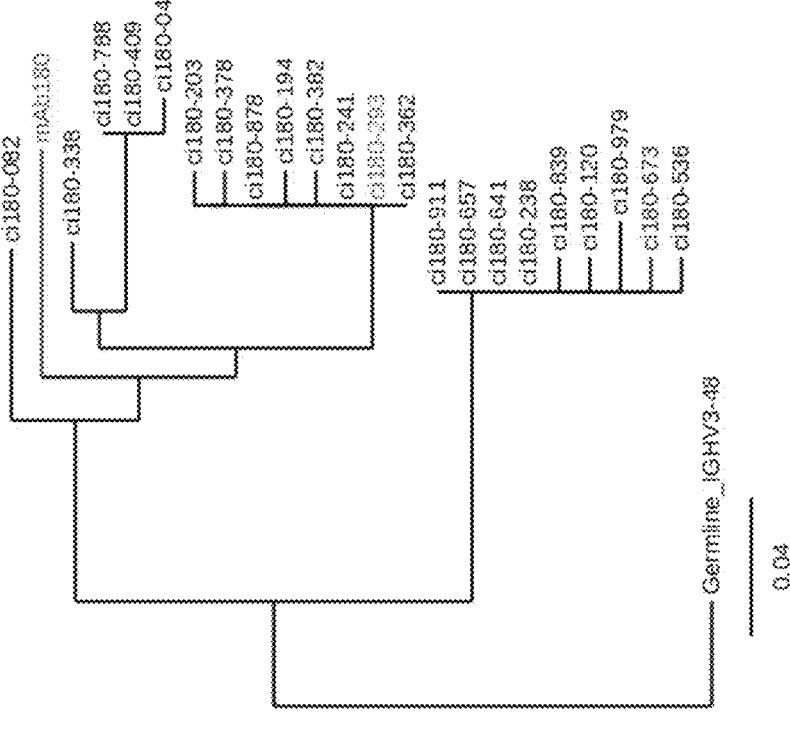

- HCV co-infection with HIV leads to:
  - HCV and HIV viral load (VL)
  - Progression to fibrosis and liver failure
  - Cardiovascular disease and stroke risk
  - HAART and DAA-associated adverse effects
  - Infection-related mortality HIV Env subtype diversity HCV E1E2 genotypic diversity Distance
—— 0.05

- BCR vs. Antibody
  - Antibodies= secreted BCR

- Clonotype
  - B cells with related sequences that are assumed to have originated from the same progenitor

- Gene/junctional diversity vs. affinity maturation

Infection Time

>24 HIV/HCV co-infected donors, accounting for >100 samples

| Patient ID | # time points |
|---|---|
| 10014 | 13 |
| 10015 | 9 |
| 10027 | 10 |

| Year post HIV infection (ypi) | 0.5 ypi | ~1.5 ypi | 3 ypi |
|---|---|---|---|
| PBMC draw date | 9/25/2003 | 10/14/2004 | 03/22/2006 |

3. Use fluorescence-activated cell sorting to separate single, and double antigen-positive memory B cells.

| Antibody | IGHV | IGHJ | CDRH3 |
|---|---|---|---|
| A2 | V4-59 | J4-2 | CAREQRDYXSGFDYW |
| A12 | V4-39 | J4-2 | CARLRRDGSYHHGAPFYFDNW |
| B4 | V4-34 | J4-2 | CARGGYQDSAGYADYW |
| B6 | V3-48 | J4-2 | CARGGRDLVRGLVMTDFFDEW |
| B12 | V4-39 | J4-2 | CARLRWSSSWYYRFDYW |
| C4 | V3-15 | J2-1 | CTTAFSMKYCSSTNCPRSDWYFDLW |

HIV/HCV Cross-Reactive Antibody V$_H$ Mutations

Highest binding to both BG505 and E2 Avi

FIG. 54

SDS PAGE:
BG505Avi

Primary: 3BNC117

Secondary: anti-
human IgG HRP

SDS PAGE:
BG505Avi

Primary: B12

Secondary: anti-
human IgG HRP

SDS PAGE: E2Avi

Primary: AP33

Secondary: anti-
human IgG HRP

SDS PAGE: E2Avi

Primary: B12

Secondary: anti-
human IgG HRP

| Subtype | TIER | Pseudoviruses | B12(Run1) | B12 (Run2) |
|---------|------|---------------|-----------|------------|
| C | | MW965 | 27.4 | 39 |
| B | 1A | MN.3 | 22 | 24.2 |
| C | | 6644 | 15.2 | 41.2 |
| C | | DU156 | 25.4 | 25.8 |
| C | | CT349 | 26.4 | 18.6 |
| C | 1B | CAP37 | >50 | 17.6 |
| C | | CE1176 | >50 | >50 |
| A | 2 | BG505 | 33.8 | >50 |
| | | 6322 | >50 | |
| | | 620345 | >50 | |
| | | 6471 | >50 | |
| | | 97ZA | >50 | |
| | | X2088 | >50 | |
| | 4 | CAP210 | >50 | |
| | Control | MuLV | 22 | 16 |

FIG. 60

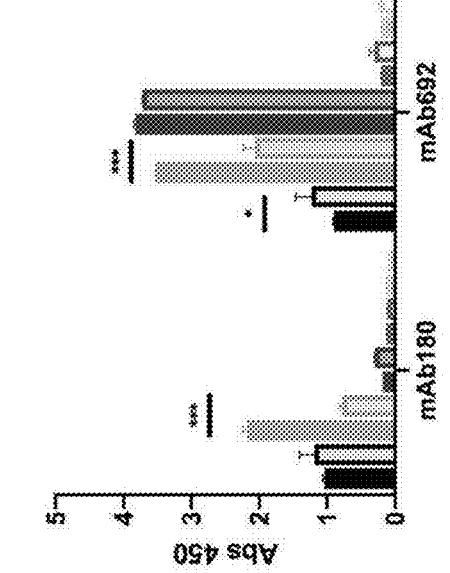
FIG. 69
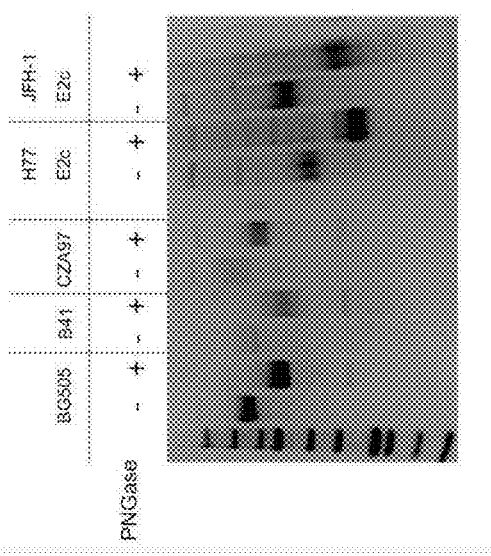

| | LPS | | Insulin | | WCL | |
| --- | --- | --- | --- | --- | --- | --- |
| | 1 | 2 | 3 | 4 | 5 | 6 |
| A — mAb180HC+722104-180LC | 0.05 | 0.05 | 0.051 | 0.048 | 0.045 | 0.047 |
| B — mAb180HC+71759-180LC | 0.041 | 0.043 | 0.054 | 0.043 | 0.043 | 0.044 |
| C — mAb180HC+671946-180LC | 0.04 | 0.042 | 0.053 | 0.048 | 0.042 | 0.041 |
| D — 359673-180HC+mAb180LC | 0.048 | 0.041 | 0.047 | 0.043 | 0.045 | 0.056 |
| E — 452878-180HC+mAb180LC | 0.043 | 0.044 | 0.042 | 0.046 | 0.043 | 0.043 |
| F — VRC01 | 0.051 | 0.046 | 0.05 | 0.057 | 0.22 | 0.075 |
| G — AP33 | 0.089 | 0.051 | 0.054 | 0.053 | 0.069 | 0.074 |
| H — Blank | 0.044 | 0.044 | 0.045 | 0.042 | 0.05 | 0.045 |

FIG. 70

| 1A | | BG505 sc Avi (WT) | BG505 sc Avi (WT) | CZA97 sc Avi (WT) | CZA97 sc Avi (WT) |
|---|---|---|---|---|---|
| 2A | mAb692 | 2.434 | 2.451 | 3.466 | 3.261 |
| Germline except CDR3 3A | germline 692 | 0.929 | 0.877 | 2.755 | 2.538 |
| 4A | g692HC+692LC | 1.257 | 1.185 | 3.073 | 2.608 |
| 5A | 692HC+g692LC | 2.103 | 2.156 | 3.357 | 3.439 |
| Earliest lineage member 6A | 58666-692LC+ 692 HC | 0.186 | 0.184 | 1.995 | 1.765 |
| 7A | AP33 | 0.073 | 0.056 | 0.046 | 0.055 |
| 8A | PG9 | 0.404 | 0.361 | 0.058 | 0.057 |
| 9A | Blank | 0.065 | 0.051 | 0.06 | 0.049 |

FIG. 71

| | H7E3 | H7E3 | [PH-1 G2] | [PH-1 G2] | E1E2 | E1E2 | LPS | LPS | Insulin | Insulin | WCL | WCL |
|---|---|---|---|---|---|---|---|---|---|---|---|---|
| mAb692 | 0.317 | 0.316 | 0.172 | 0.18 | 0.179 | 0.158 | 0.098 | 0.084 | 0.096 | 0.098 | 0.084 | 0.084 |
| germline-G92 | 0.134 | 0.141 | 0.113 | 0.112 | 0.097 | 0.096 | 0.068 | 0.062 | 0.072 | 0.066 | 0.086 | 0.078 |
| g692HC-692LC | 1.094 | 1.118 | 0.805 | 0.812 | 0.622 | 0.588 | 0.099 | 0.128 | 0.126 | 0.143 | 0.732 | 0.749 |
| 692HC-gG92LC | 0.174 | 0.171 | 0.142 | 0.113 | 0.074 | 0.125 | 0.065 | 0.066 | 0.14 | 0.154 | 0.052 | 0.054 |
| g692HC-g211-692HC | 0.506 | 0.482 | 0.335 | 0.322 | 0.282 | 0.256 | 0.147 | 0.147 | 0.094 | 0.122 | 0.131 | 0.138 |
| dE10 | | | | | | | 0.08 | 0.154 | 0.347 | 0.252 | 0.657 | 0.826 |
| PG16 (AP33 WCL) | 0.147 | 0.142 | 0.152 | 0.141 | 0.121 | 0.137 | 0.061 | 0.061 | 0.065 | 0.057 | 0.184 | 0.201 |
| AP33 (blank WCL) | 4.483 | 4.463 | 4.351 | 4.379 | 4.337 | 4.341 | 0.058 | 0.053 | 0.064 | 0.058 | 0.04 | 0.038 |

HIV/HCV CROSS-REACTIVE ANTIBODIES AND USES THEREOF

CROSS REFERENCE TO RELATED APPLICATIONS

This application is a United States National Phase Patent Application of International Patent Application Number PCT/US2020/026552, filed on Apr. 3, 2020, which claims the benefit of U.S. Provisional Patent Application Ser. No. 62/829,526 filed Apr. 4, 2019 and U.S. Provisional Patent Application Ser. No. 62/971,477 filed Feb. 7, 2020, the disclosures of which are expressly incorporated herein by reference.

STATEMENT REGARDING FEDERALLY SPONSORED RESEARCH

This invention was made with government support under Grant Nos. AI131722 and AI152693, awarded by the National Institutes of Health. The government has certain rights in the invention.

REFERENCE TO SEQUENCE LISTING

The Sequence Listing submitted Apr. 3, 2020, as a text file named "10644-095WO1_2020_04_03_ST25.txt," created on Apr. 3, 2020, and having a size of 4 MB is hereby incorporated by reference pursuant to 37 C.F.R. § 1.52 (e)(5).

FIELD

The present disclosure relates to antibodies and uses thereof for treating an HIV infection, an HCV infection, or an HIV/HCV co-infection.

BACKGROUND

HIV and HCV on their own are associated with devastating pathologies, affecting up to 200 million people combined. The prevalence of co-infection with these two pathogens is also high, estimated at 4-5 million people worldwide. While the global health burden of these viruses has been lessened significantly by the advent of highly active anti-retroviral therapy (HAART) and direct-acting antivirals (DAA) for HIV and HCV respectively, these therapies are expensive and require high patient compliance to often complex drug regimens. Furthermore, re-infection rates are high, especially for HIV/HCV co-infected individuals, which have been reported as having the highest risk of re-infection with either virus, with re-infection rates >20%. Therefore, even though effective drug therapies for HIV and HCV already exist, a number of factors including drug resistance, patient compliance, and likelihood of re-infection, strongly motivate work toward developing alternative therapeutic and prophylactic tools. Such new tools will be of great utility in the setting of HIV/HCV co-infection, where the chronic exposure to two constantly evolving pathogens leads to significantly exacerbated health problems compared to mono-infection with either pathogen. What is needed are novel compositions and methods for treating HIV and HCV mono-infections and HIV/HCV co-infection.

SUMMARY

Disclosed herein are recombinant antibodies and uses thereof for preventing, treating, inhibiting, or reducing HIV and/or HCV infection.

In some aspects, disclosed herein is a recombinant antibody, said antibody comprising a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRL3 comprises an amino acid sequence at least 60% identical to

```
                                    (SEQ ID NO: 13)
      MQPLQLPDT, (SEQ ID NO: 25)
      QQSYNVPT, (SEQ ID NO: 39)
      HQSSSLPFT, (SEQ ID NO: 49)
      QHFYSSPPT, (SEQ ID NO: 88)
      CLYAGSYSWV,
      or (SEQ ID NO: 101)
      QVWDSSSEHVV;
``` and/or

CDRH3 comprises an amino acid sequence at least 60% identical to

```
                                    (SEQ ID NO: 104)
      ARVAPPGVVNNKWFDI, (SEQ ID NO: 110)
      ARSEKRVTMTRKIKGRWFGP, (SEQ ID NO: 1817)
      CAAGLWSGDLSRPRYSDSW, (SEQ ID NO: 1818)
      CAKGLTTESRLEFW, (SEQ ID NO: 1819)
      CVSSWGPESPYYFDYW,
      or (SEQ ID NO: 1820)
      CAREYCTGGDCHFFLDYW.
```

In some embodiments, the CDRL3 comprises at least one amino acid substitution when compared to SEQ ID NO: 13, 25, 39, 49, 88, or 101.

In some embodiments, the at least one amino acid substitution is selected from the group consisting of a) at position 1 when compared to SEQ ID NO: 13, wherein the substituting amino acid residue is K;

b) at position 3 when compared to SEQ ID NO: 13, wherein the substituting amino acid residue is selected from the group consisting of A, T, G, V, D, Y, and F;

c) at position 6 when compared to SEQ ID NO: 13, wherein the substituting amino acid residue is selected from the group consisting of H, S, T, P, I, V, P, R, and V;

d) at position 9 when compared to SEQ ID NO: 13, wherein the substituting amino acid residue is selected from the group consisting of Y, L, H, P, I, G, C, J, R, and Q;

e) at position 5 when compared to SEQ ID NO: 25, wherein the substituting amino acid residue is selected from the group consisting of T, P, Y, R, I, G, and S;

f) at position 6 when compared to SEQ ID NO: 25, wherein the substituting amino acid residue is selected from the group consisting of A, T, and P;

g) at position 7 when compared to SEQ ID NO: 25, wherein the substituting amino acid residue is selected from the group consisting of W, A, R, G and L;

h) at position 3 when compared to SEQ ID NO: 39, wherein the substituting amino acid residue is T;

i) at position 4 when compared to SEQ ID NO: 39, wherein the substituting amino acid residue is selected from the group consisting of R, G, T, Y, A, and K;

j) at position 6 when compared to SEQ ID NO: 39, wherein the substituting amino acid residue is F;

k) at position 7 when compared to SEQ ID NO: 39, wherein the substituting amino acid residue is selected from the group consisting of G, Q, L, and S.

l) at position 8 when compared to SEQ ID NO: 39, wherein the substituting amino acid residue is selected from the group consisting of G, Q, Y, W, H, and L;

m) at position 9 when compared to SEQ ID NO: 39, wherein the substituting amino acid residue is selected from the group consisting of A, P, and S.

n) at position 3 when compared to SEQ ID NO: 49, wherein the substituting amino acid residue is L;

o) at position 5 when compared to SEQ ID NO: 49, wherein the substituting amino acid residue is T;

p) at position 6 when compared to SEQ ID NO: 49, wherein the substituting amino acid residue is selected from the group consisting of N, D, and K;

q) at position 2 when compared to SEQ ID NO: 88, wherein the substituting amino acid residue is selected from the group consisting of S, P and T;

r) at position 6 when compared to SEQ ID NO: 88, wherein the substituting amino acid residue is R;

s) at position 8 when compared to SEQ ID NO: 88, wherein the substituting amino acid residue is selected from the group consisting of N, W, and T;

t) at position 9 when compared to SEQ ID NO: 88, wherein the substituting amino acid residue is A;

u) at position 2 when compared to SEQ ID NO: 101, wherein the substituting amino acid residue is selected from the group consisting of M, A, and L;

v) at position 3 when compared to SEQ ID NO: 101, wherein the substituting amino acid residue is C;

w) at position 4 when compared to SEQ ID NO: 101, wherein the substituting amino acid residue is Y;

x) at position 7 when compared to SEQ ID NO: 101, wherein the substituting amino acid residue is N; and y) at position 8 when compared to SEQ ID NO: 101, wherein the substituting amino acid residue is D.

In some embodiments, the CDRL3 comprises an amino acid sequence selected from the group consisting of SEQ ID NOs: 1-12, 14-24, 26-38, 40-48, 50-87, and 89-100. In some embodiments, the CDRL3 comprises an amino acid sequence selected from the group consisting of SEQ ID NOs: 1-12, 14-24, 26-38, 40-48, 50-51, and 89-100.

In some embodiments, the VL comprises an amino acid sequence selected from the group consisting of SEQ ID NOs: 119-1693.

In some embodiments, the CDRL3 comprises an amino acid sequence selected from SEQ ID NOs: 13, 25, 39, 49, 88, 101, and 1883-1888. In some embodiments, the CDRL1 comprises an amino acid sequence selected from SEQ ID NOs: 13120-13125. In some embodiments, the CDRL2 comprises an amino acid sequence selected from SEQ ID NOs: 13126-13131.

In some embodiments, the VL comprises an amino acid sequence selected from SEQ ID NOs: 119, 227, 242, 351, 1399, 1406, and 1899-1904.

In some embodiments, the CDRH3 comprises at least one amino acid substitution when compared to SEQ ID NO: 104, 110, 1817, 1818, 1819, or 1820. In some embodiments, the at least one amino acid substitution is selected from the group consisting of a) at position 3 when compared to SEQ ID NO: 104, wherein the substituting amino acid residue is G or I;

b) at position 4 when compared to SEQ ID NO: 104, wherein the substituting amino acid residue is S, T, or P;

c) at position 9 when compared to SEQ ID NO: 104, wherein the substituting amino acid residue is A;

d) at position 11 when compared to SEQ ID NO: 104, wherein the substituting amino acid residue is K or H;

e) at position 14 when compared to SEQ ID NO: 104, wherein the substituting amino acid residue is L;

f) at position 16 when compared to SEQ ID NO: 104, wherein the substituting amino acid residue is L or T;

g) at position 1 when compared to SEQ ID NO: 110, wherein the substituting amino acid residue is T or S;

h) at position 5 when compared to SEQ ID NO: 110, wherein the substituting amino acid residue is N or P;

i) at position 7 when compared to SEQ ID NO: 110, wherein the substituting amino acid residue is I, N, K, or L;

j) at position 9 when compared to SEQ ID NO: 110, wherein the substituting amino acid residue is L or T;

k) at position 10 when compared to SEQ ID NO: 110, wherein the substituting amino acid residue is A or V;

l) at position 11 when compared to SEQ ID NO: 110, wherein the substituting amino acid residue is L.

m) at position 17 when compared to SEQ ID NO: 110, wherein the substituting amino acid residue is S;

n) at position 19 when compared to SEQ ID NO: 110, wherein the substituting amino acid residue is D; and o) at position 20 when compared to SEQ ID NO: 110, wherein the substituting amino acid residue is S.

In some embodiments, the CDRH3 comprises an amino acid sequence selected from the group consisting of SEQ ID NOs: 102-103, 105-109, and 111-118.

In some embodiments, the VH comprises an amino acid sequence selected from the group consisting of SEQ ID NOs: 1694-1756.

In some embodiments, the CDRH3 comprises an amino acid sequence selected from the group consisting of SEQ ID NOs: 104, 110, and 1817-1822. In some embodiments, the CDRH1 comprises an amino acid sequence selected from SEQ ID NOs: 13102-13107. In some embodiments, the CDRH2 comprises an amino acid sequence selected from SEQ ID NOs: 13108-13113.

In some embodiments, the VH comprises an amino acid sequence selected from the group consisting of SEQ ID NOs: 1895-1898, 1694, and 1718.

In some embodiments, the recombinant antibody disclosed herein is selected from the group consisting of a) a recombinant antibody comprising the CDRL3 of SEQ ID NO: 88 or 1887 and the CDRH3 of SEQ ID NO: 104 or 1821;

b) a recombinant antibody comprising the CDRL3 of SEQ ID NO: 101 or 1888 and the CDRH3 of SEQ ID NO: 110 or 1822;

c) a recombinant antibody comprising the CDRL3 of SEQ ID NO: 13 or 1883 and the CDRH3 of SEQ ID NO: 1817;

d) a recombinant antibody comprising the CDRL3 of SEQ ID NO: 25 or 1884 and the CDRH3 of SEQ ID NO: 1818;

e) a recombinant antibody comprising the CDRL3 of SEQ ID NO: 39 or 1885 and the CDRH3 of SEQ ID NO: 1819; and f) a recombinant antibody comprising the CDRL3 of SEQ ID NO: 49 or 1886 and the CDRH3 of SEQ ID NO: 1820.

In some embodiments, the recombinant antibody binds to at least one HIV antigen and/or at least one HCV antigen.

In some aspects, disclosed herein is a nucleic acid encoding the recombinant antibody of any preceding aspect.

In some aspects, disclosed herein is a host cell comprising the expression cassette or plasmid of any preceding aspect.

In some aspects, disclosed herein is a method of producing a recombinant antibody comprising cultivating or maintaining the host cell of any preceding aspect under conditions to produce said recombinant antibody.

In some aspects, disclosed herein is a method of treating, preventing, reducing, and/or inhibiting HIV/HCV co-infection comprising administering to a subject a therapeutically effective amount of the recombinant antibody of any preceding aspect.

In some aspects, disclosed herein is a method of treating, preventing, reducing, and/or inhibiting HIV infection comprising administering to a subject a therapeutically effective amount of the recombinant antibody of any preceding aspect.

In some aspects, disclosed herein is a method of treating, preventing, reducing, and/or inhibiting HCV infection comprising administering to a subject a therapeutically effective amount of the recombinant antibody of any preceding aspect.

DESCRIPTION OF DRAWINGS

The patent or application file contains at least one drawing executed in color. Copies of this patent or patent application publication with color drawing(s) will be provided by the Office upon request and payment of the necessary fee.

The accompanying figures, which are incorporated in and constitute a part of this specification, illustrate aspects described below.

FIG. 24A. Identified HIV/HCV mAbs show minimal polyreactivity as measured by ELISA binding to non-specific antigens: lipopolysaccharide (LPS), human recombinant insulin, and whole cell lysates (HEp-2, A549). FIG. 24B. Identified HIV/HCV mAbs show minimal polyreactivity as measured by ELISA binding to cardiolipin and nuclear antigens (ANA). FIG. 24C. HIV/HCV mAb180 shows no polyreactivity as measured by indirect immunofluorescence staining on HEp-2 cells. HIV/HCV mAb692 shows moderate polyreactivity as measured by indirect immunofluorescence staining on HEp-2 cells. DAPI-stained nuclei and FITC-conjugated antibody. FIG. 24D. This figure is cropped from images in FIG. 24C with DIC filter applied.

FIG. 29A shows mAb692 heavy chain development and relative positions of tested intermediate heavy chain sequences shown in various colors (left). Each of the colored heavy chain was paired with 692 light chain and tested for ELISA binding to recombinant HIV antigen (right). FIG. 29B shows mAb692 heavy chain development and relative positions of tested intermediate heavy chain sequences shown in various colors (left). Each of the colored heavy chain was paired with 692 light chain and tested for ELISA binding to recombinant HCV antigen (right).

FIGS. 31A-31B show that mAb180 acquired mutations are required for HIV recognition. FIG. 31A shows mAb180 heavy chain development and relative positions of tested intermediate heavy chain sequences shown in various colors (left). Each of the colored heavy chain was paired with 180 light chain and tested for ELISA binding to recombinant HIV antigen (right). FIG. 31B shows mAb180 heavy chain development and relative positions of tested intermediate heavy chain sequences shown in various colors (left). Each of the colored heavy chain was paired with 180 light chain and tested for ELISA binding to recombinant HCV antigen (right).

(FIG. 36A) LIBRA-Seq turns antigen-BCR interactions into "sequence-able" events. Antigen screening library size is constrained only by unique oligo barcodes. The technology allows for high throughput mapping of BCR specificity, and turns antigen-BCR interactions into "sequence-able" events, exponentially increasing screening library sizes. (FIG. 36B) Further, using LIBRA-seq one can map not only whether a given B cell was positive for an antigen, but which antigen(s) and substantially decrease functional validation time.

FIG. 49A shows PCR products at the correct size for the heavy chain gene run an agarose gel stained with EtBr.

FIG. 49B shows protein bands at the correct size for reduced and non-reduced antibody run on an SDS-PAGE gel stained with COOMASSIE™blue.

```
                                   (SEQ ID NO: 13144)
EVQLVESGPGLVKPSETLSLTCTVSGGSISYSSYYWGWIRQPPGKGLEWI

GSIYYSGSTYSNPSLKSRVTISVDTSKNQFSLKLSSVTAADTAVYYCARL

RWSSSWYYRFDYWGQGTLVTVSS;

(SEQ ID NO: 13145)
QLQLQESGPGLVKPSETLSLTCTVSGGSISSSSYYWGWIRQPPGKGLEWI

GSIYYSGSTYYNPSLKSRVTISVDTSKNQFSLKLSSVTAADTAVYYCARY

FDYWGQGTLVTVSS;

(SEQ ID NO: 13146)
QVQLVQSGGQMKKPGESMRISCRASGYEFIDCTLNWIRLAPGKRPEWMGW

LKPRGGAVNYARPLQGRVTMTRDVYSDTAFLELRSLTVDDTAVYFCTRGK

NCDYNWDFEHWGRGTPVIVSS;

(SEQ ID NO: 13147)
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCARAE

YFQHWGQGTLVTVSS.
```

Figure 55:
Figure 55:
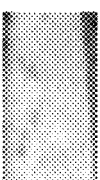
Figure 55:
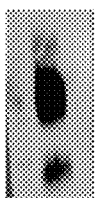
Figure 55:

FIG. 55 shows B12 antibody recognition to denatured proteins.

Figure 56:
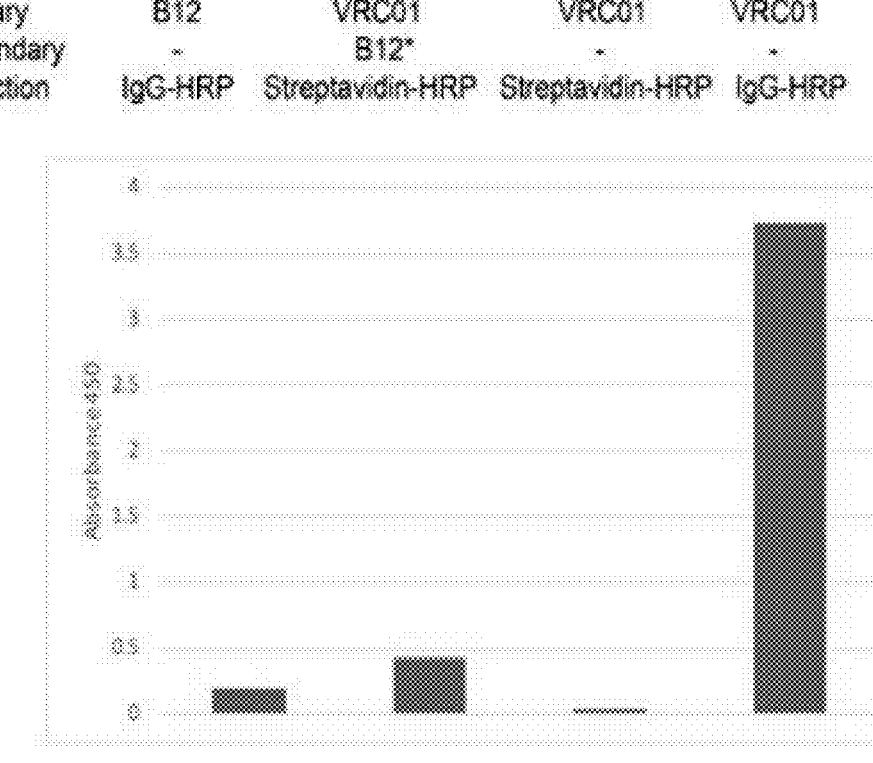
Figure 56:
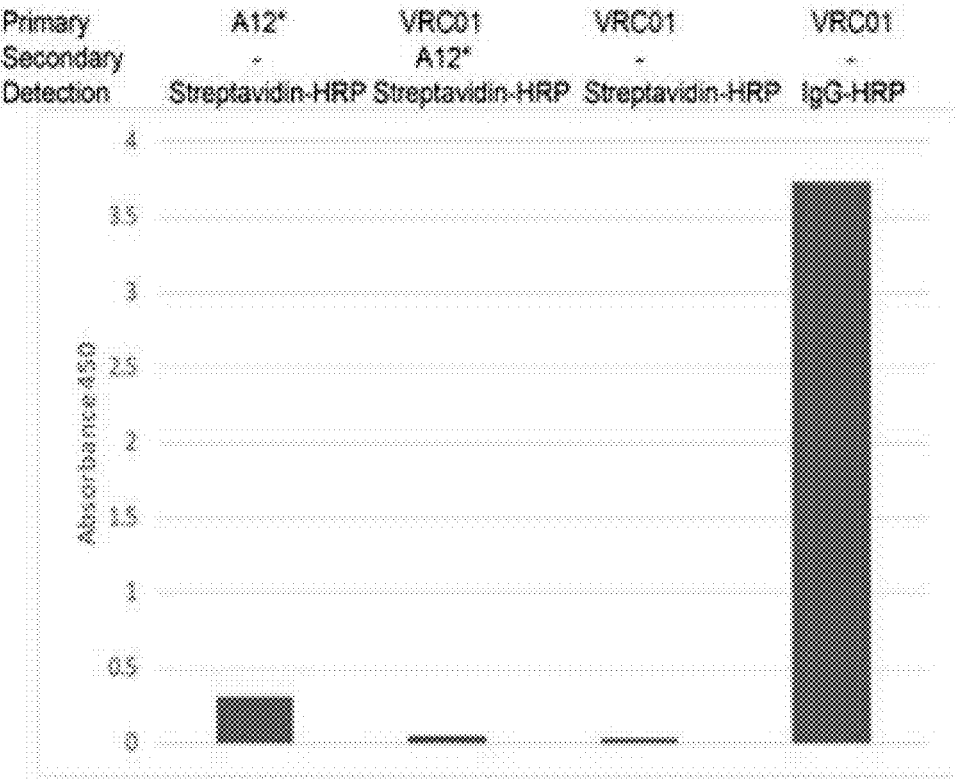
Figure 56:
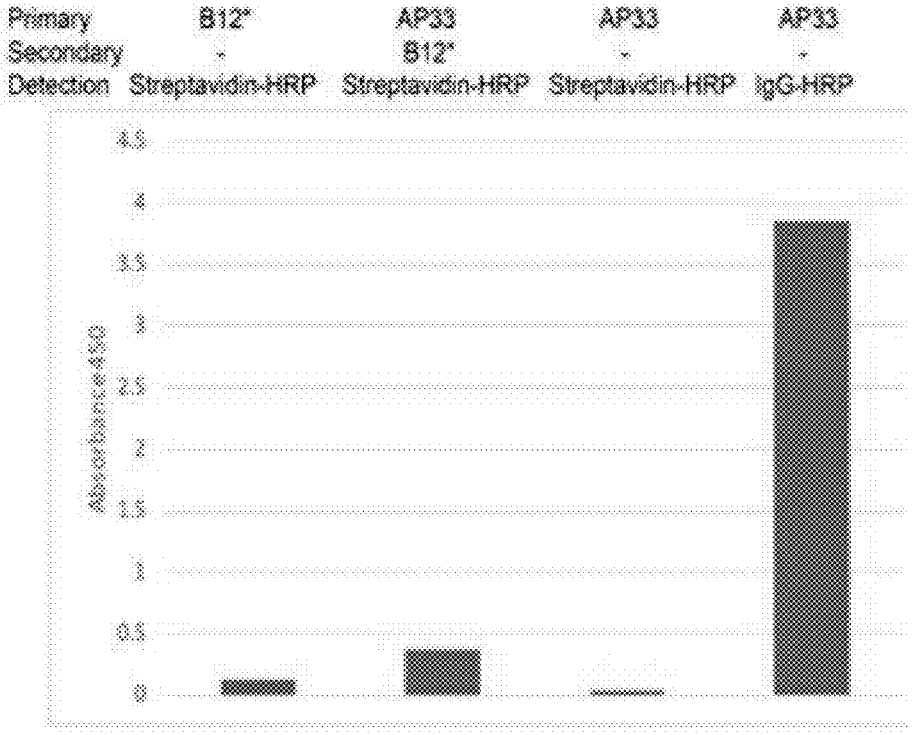
Figure 56:
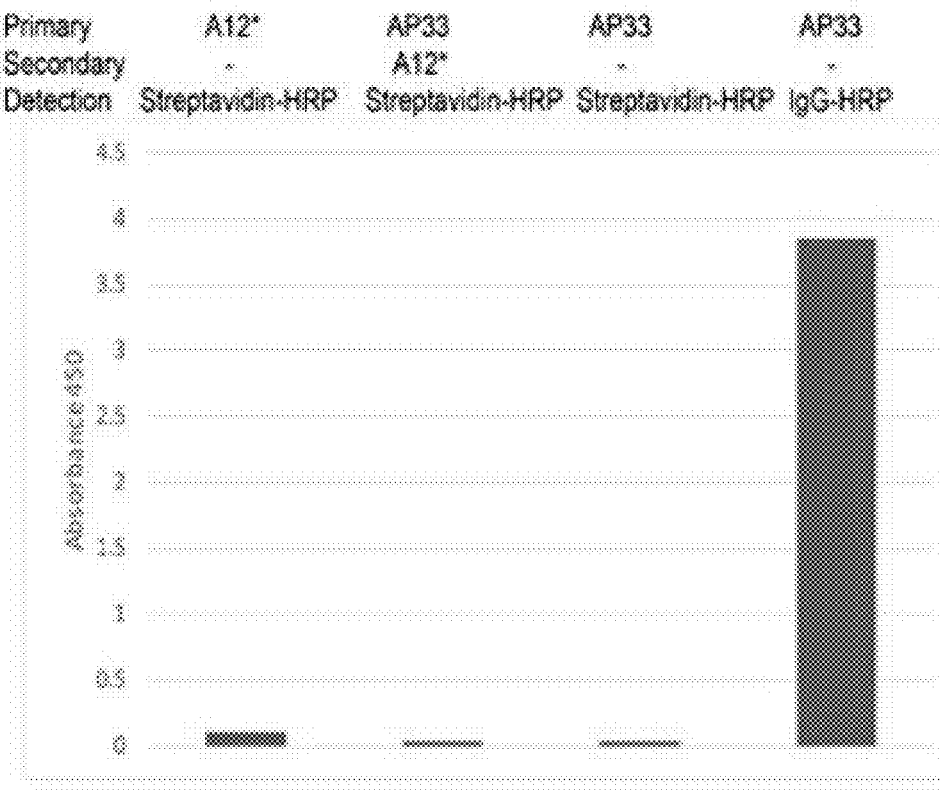

FIG. 56 shows that receptor binding site antibodies do not disrupt B12 binding.

Figure 57:
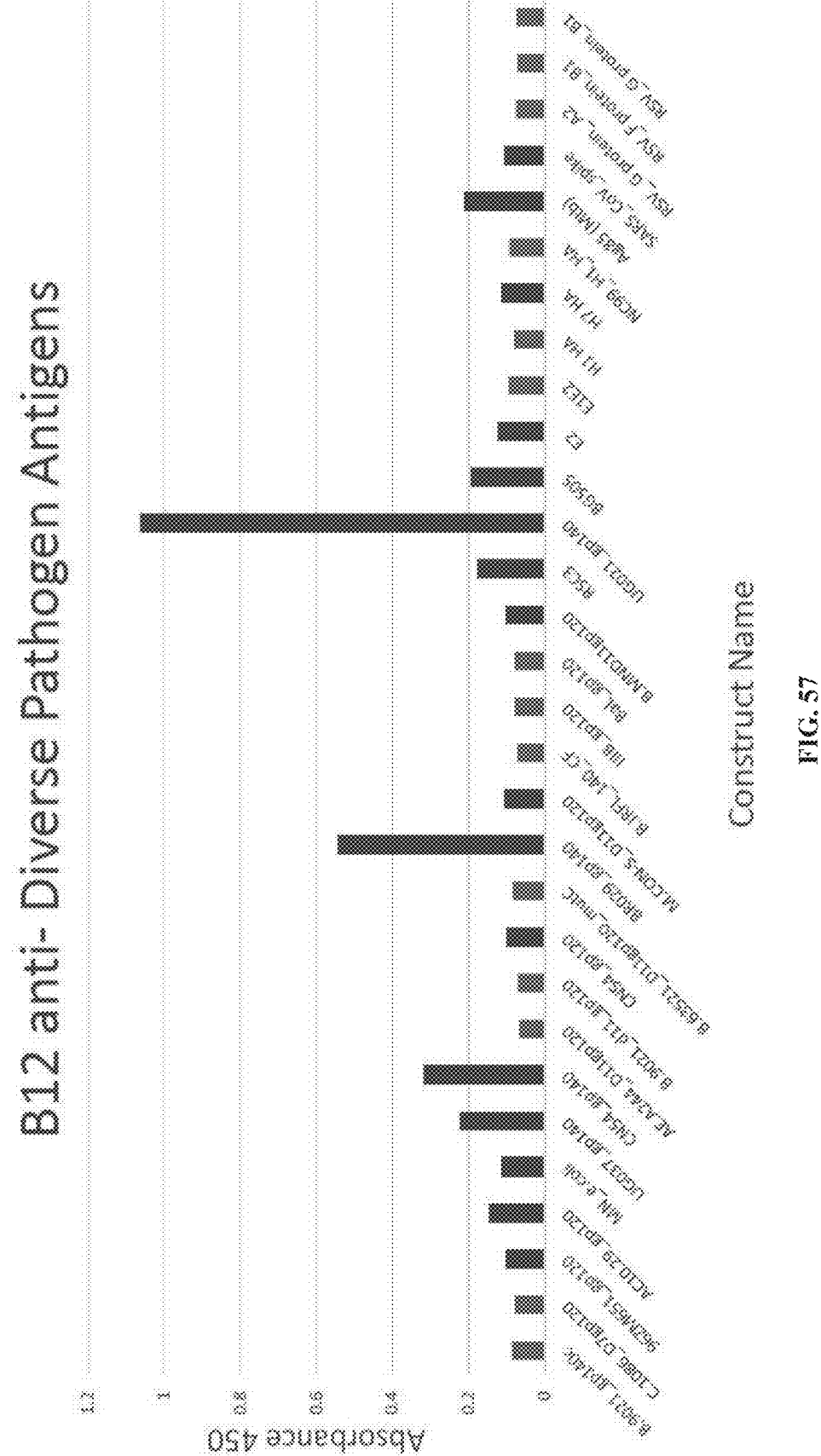

FIG. 57 shows that B12 antibody recognizes a wide range of pathogen antigens. Darker shading indicates B12 binding 3X background or more.

Figure 58:
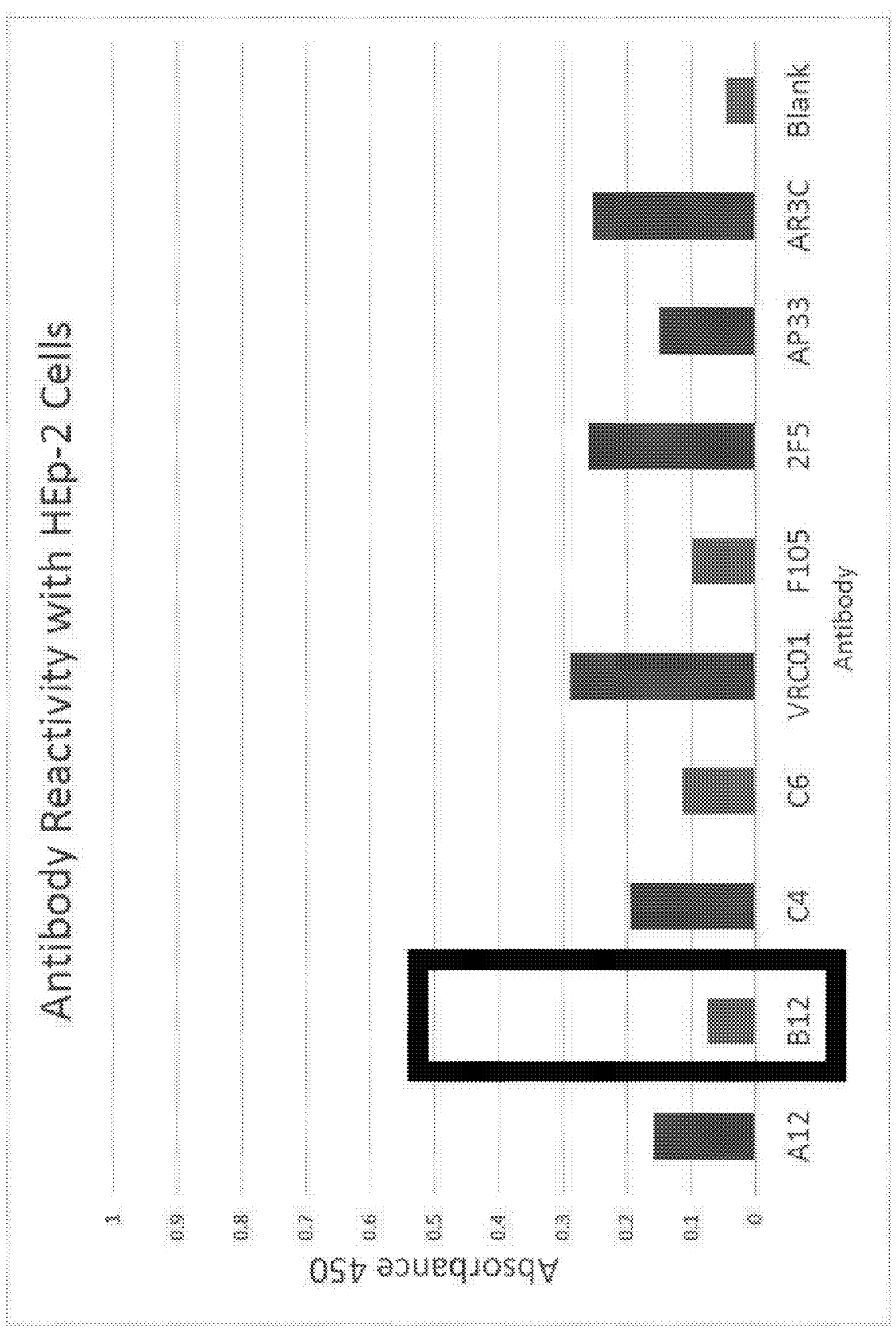

FIG. 58 shows that B12 is not polyreactive in HEp-2 ELISA.

Figure 59A:
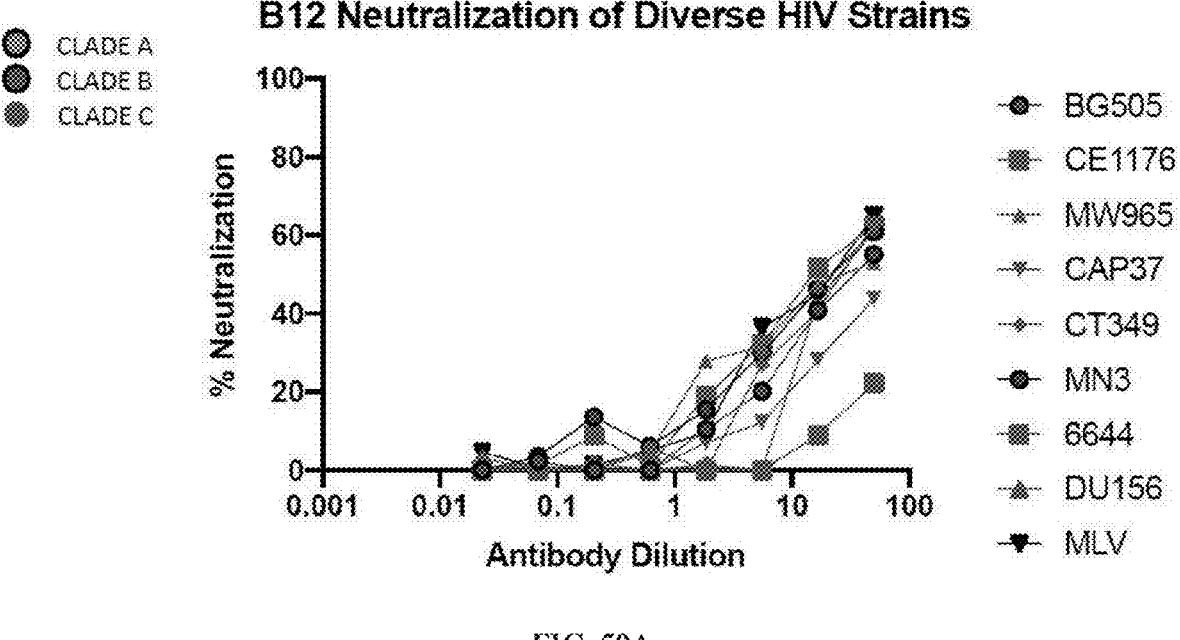
Figure 59B:
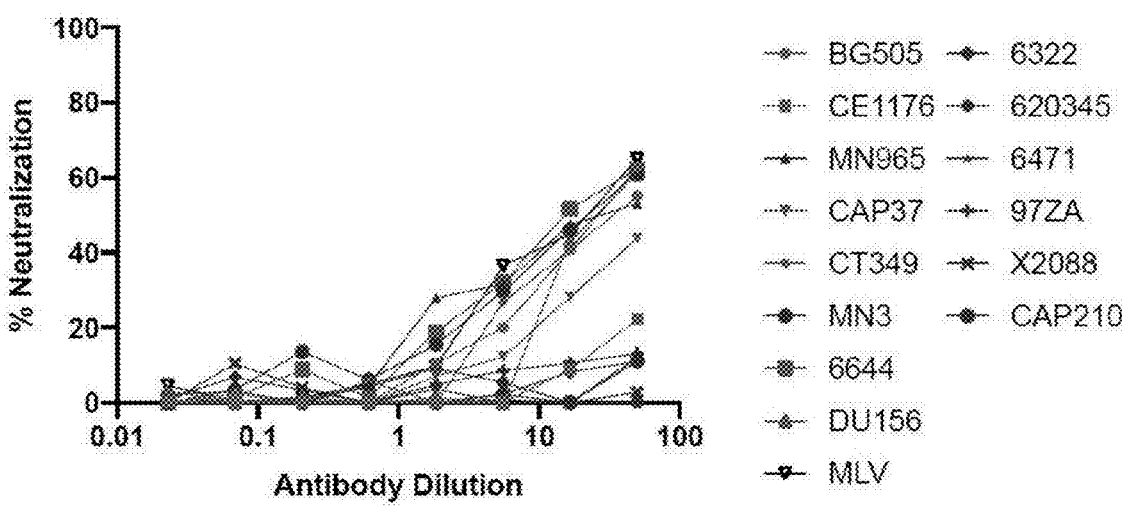

FIG. 59A-59B show antibody B12 neutralization. FIG. 59A shows levels of neutralization colored by HIV clade A: BG505 B: MN.3 C: CE1176, MW965, CAP37, CT349, 6644, DU156; Control: MLV; MLV env but the rest of the virus is HIV. FIG. 59B shows levels of neutralization colored according to HIV neutralization tier: Tier 1A: MN965, MN.3; Tier 1B: CAP37, CT349, 6644, DU156; Tier 2: BG505, CE1176; Tier 4:6322, 620345, 6471, 97ZA, X2088, CAP210 MLV.

FIG. 60 shows that B12 antibody neutralizes several HIV pseudotyped viruses. Shown is the concentration of antibody at which neutralization was 50% inhibited. IC50 was given in μg/ml.

Figure 61:
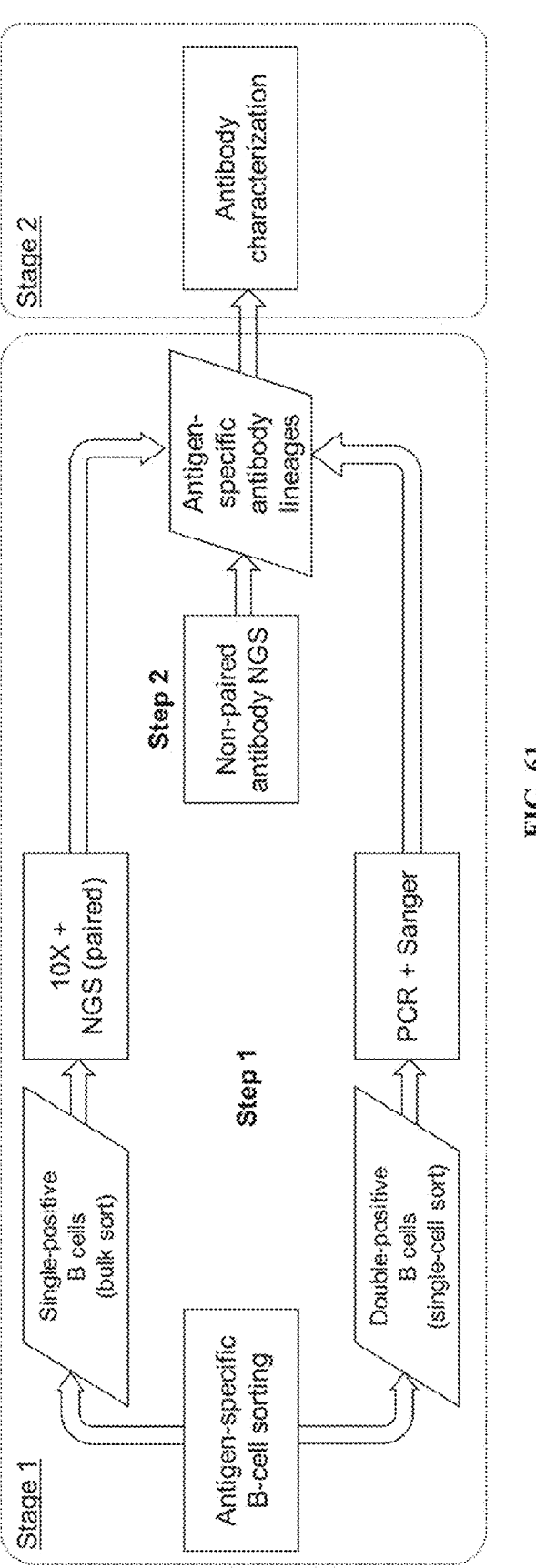

FIG. 61 shows experiment design for identifying antigen-specific antibodies in HIV/HCV co-infected individuals. Single-positive B cells (positive for either the HIV antigen probe or the HCV antigen probe) are the focus of step 1, whereas the double-positive B cells (positive for both the HIV and HCV antigen probes) are the focus of step 2.

Figures 62A, 62B:
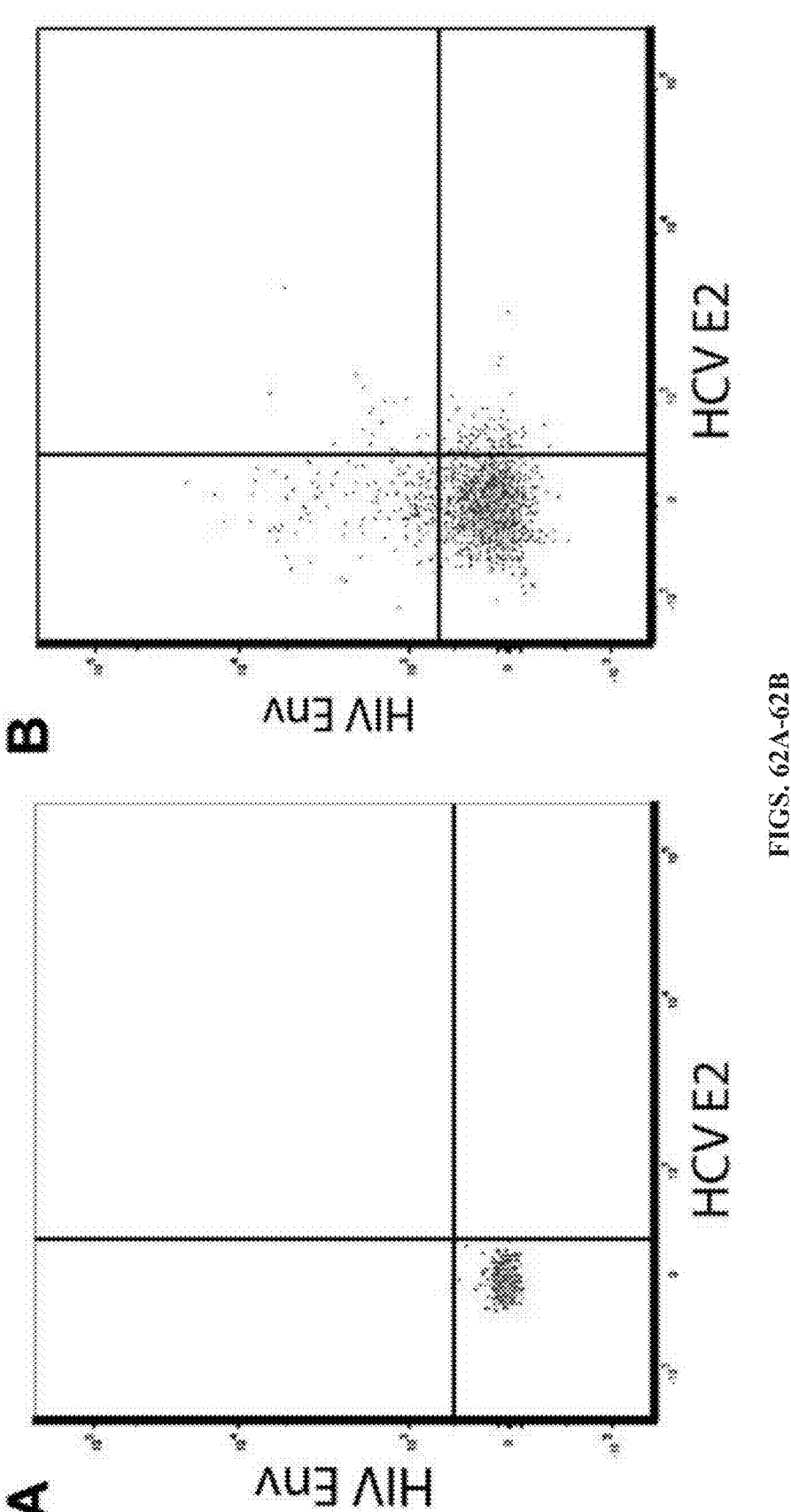

FIGS. 62A-62B shows identification of HIV- and HCV-specific B cells. PBMCs were stained for IgG+, memory B cells, as well as for HIV and HCV antigens, as described in the text. FIG. 62A shows that no antigen-positive B cells were identified from PBMCs from a non-infected individual. FIG. 62B shows that single- and double-antigen-positive B cells were identified from PBMCs from an HIV/HCV co-infected individual.

Figure 63:
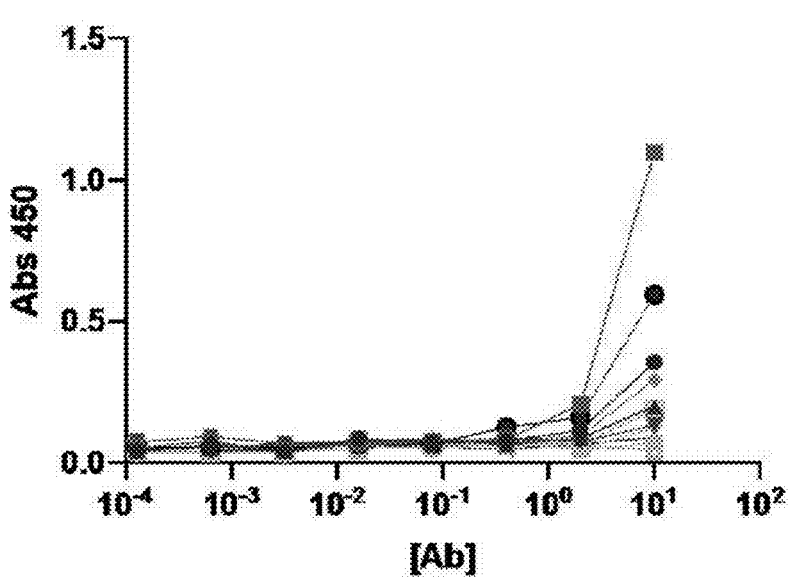
Figure 63:
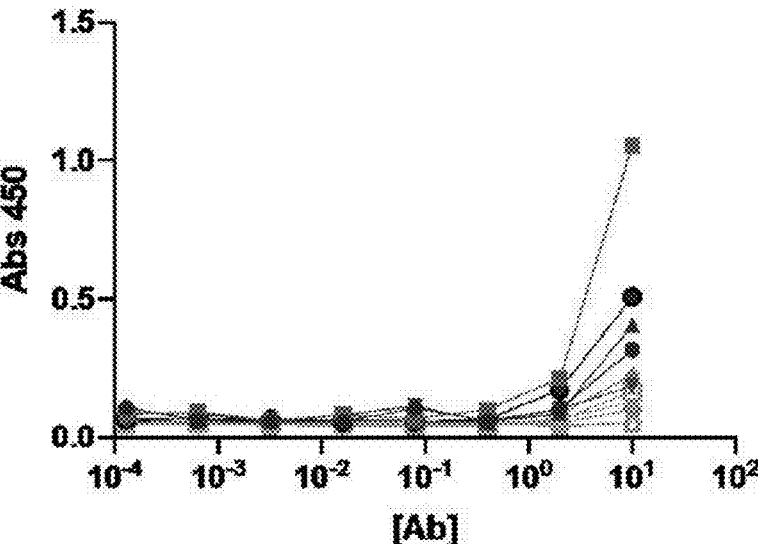

FIG. 63 shows HIV/HCV cross-reactive antibody binding to HIV (BG505.664.SOSIP) and HCV (HCV H77 E2core) antigens as measured by direct or sandwich ELISA.

Figure 64:
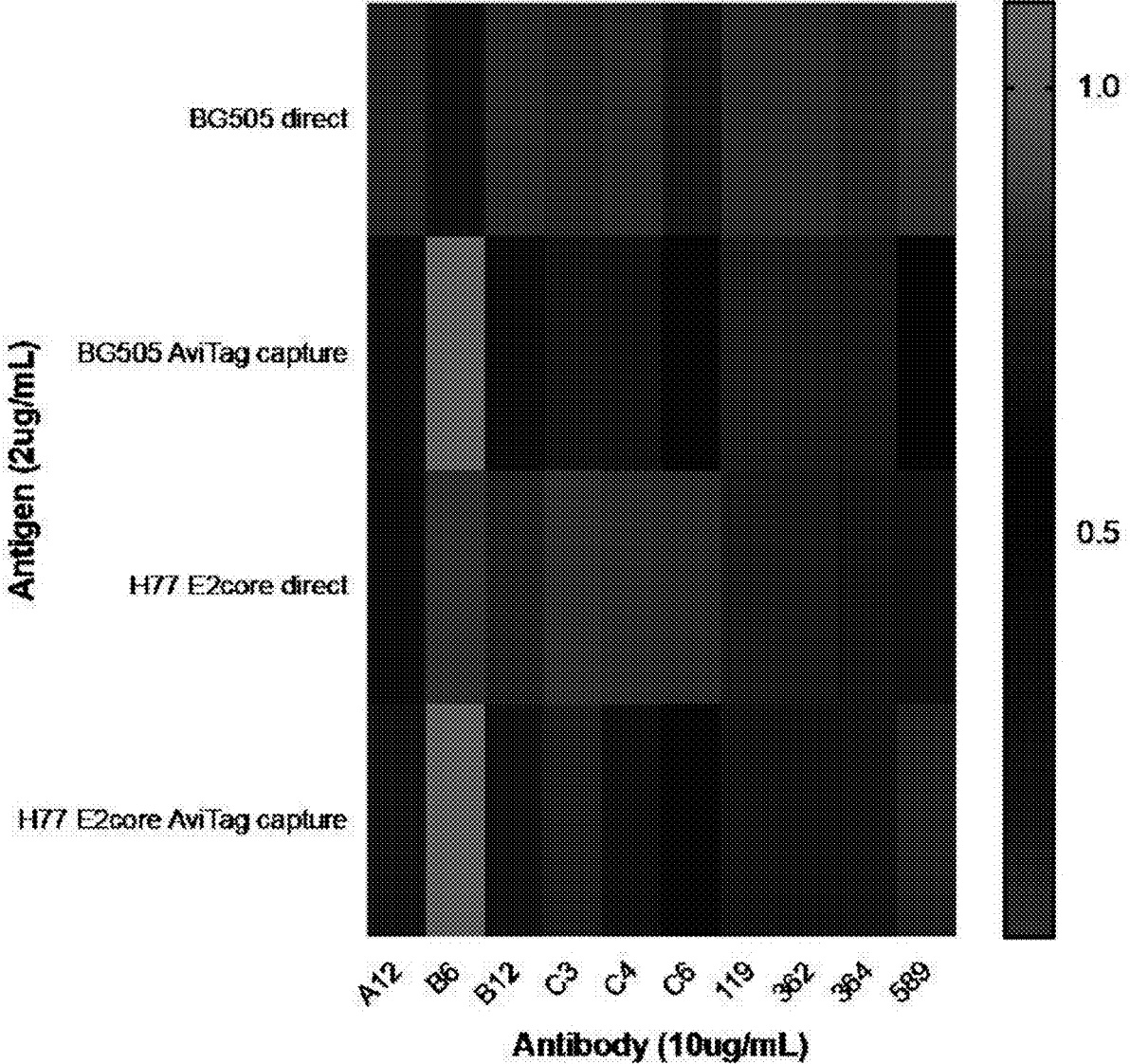

FIG. 64 shows the data from FIG. 63 displayed as a heatmap of ELISA binding.

Figure 65:
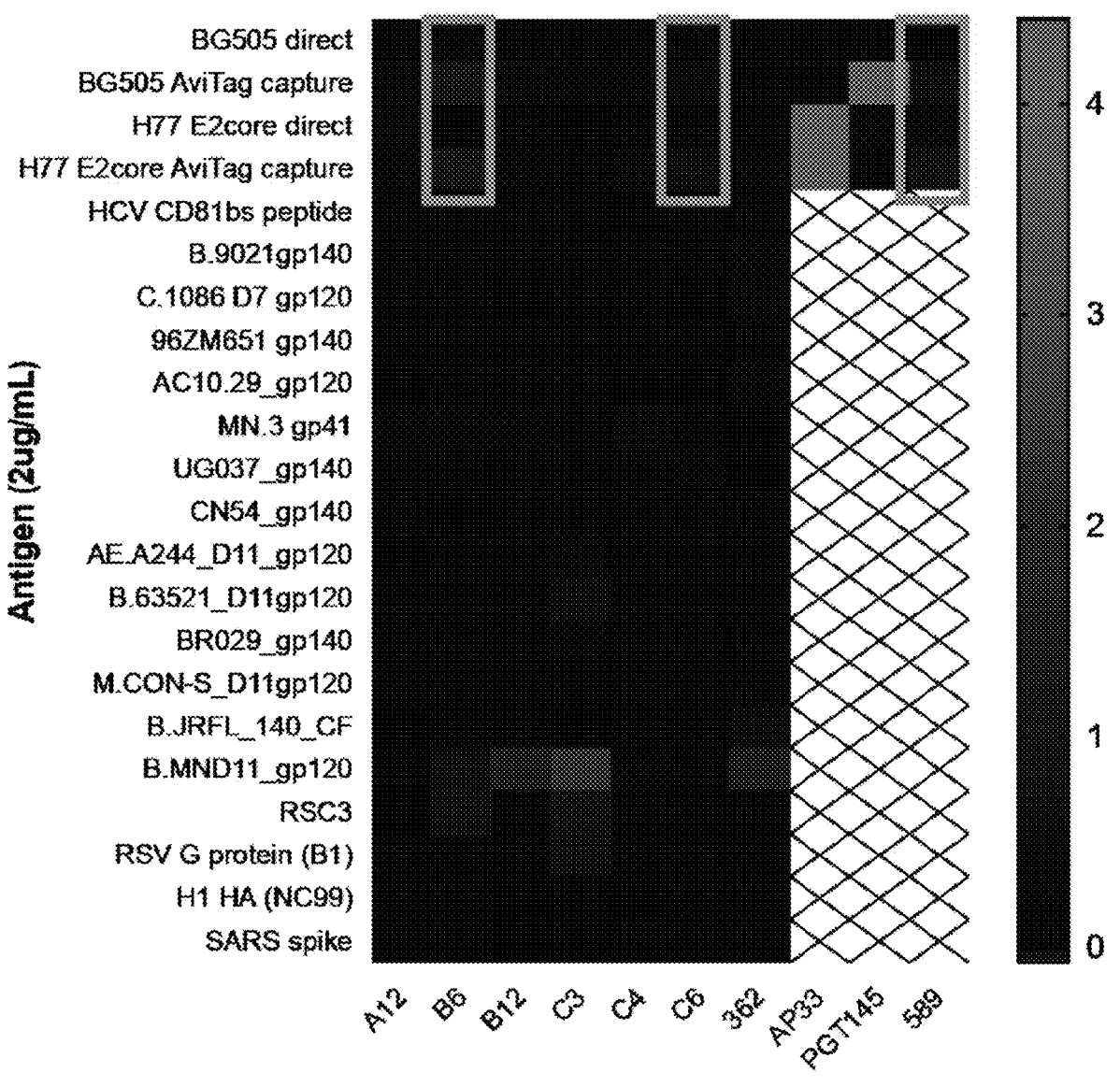

FIG. 65 shows ELISA binding of HIV/HCV mAbs to a panel of HIV and HCV antigens shown as a heatmap.

Figure 66:
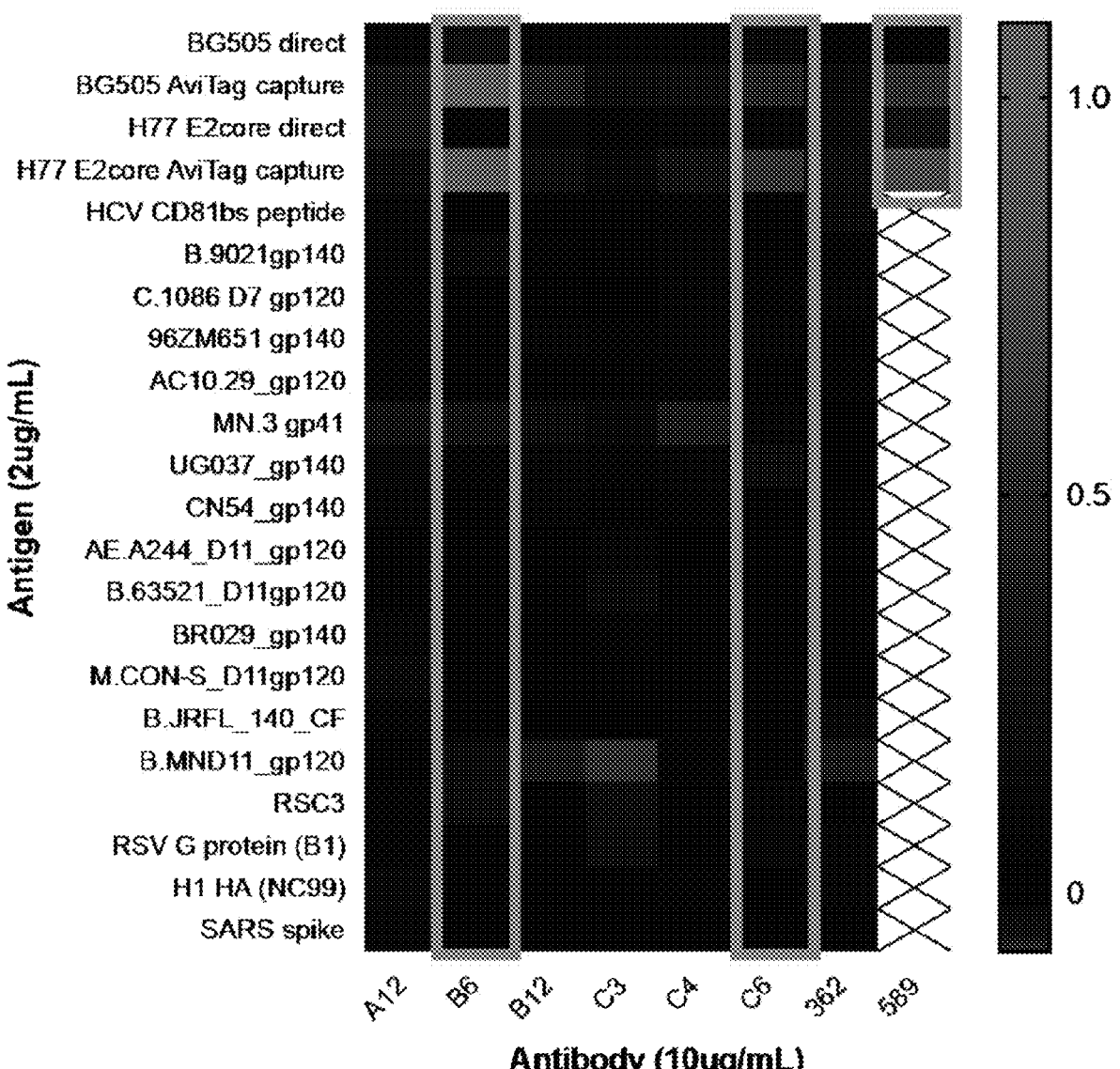

FIG. 66 shows same data as FIG. 65, minus AP33 and PGT145 antibody rows.

Figures 67A, 67B:
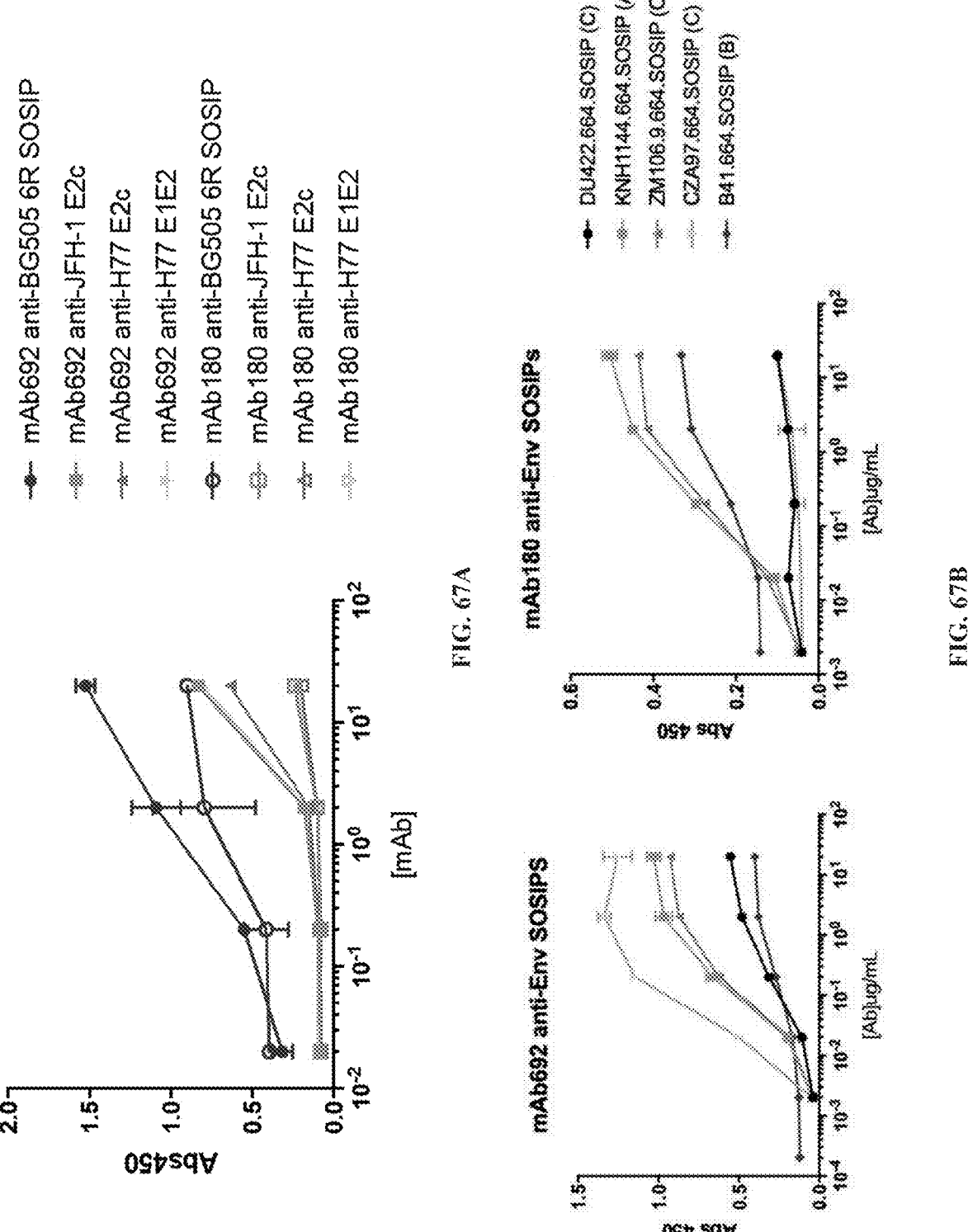
Figure 67C:
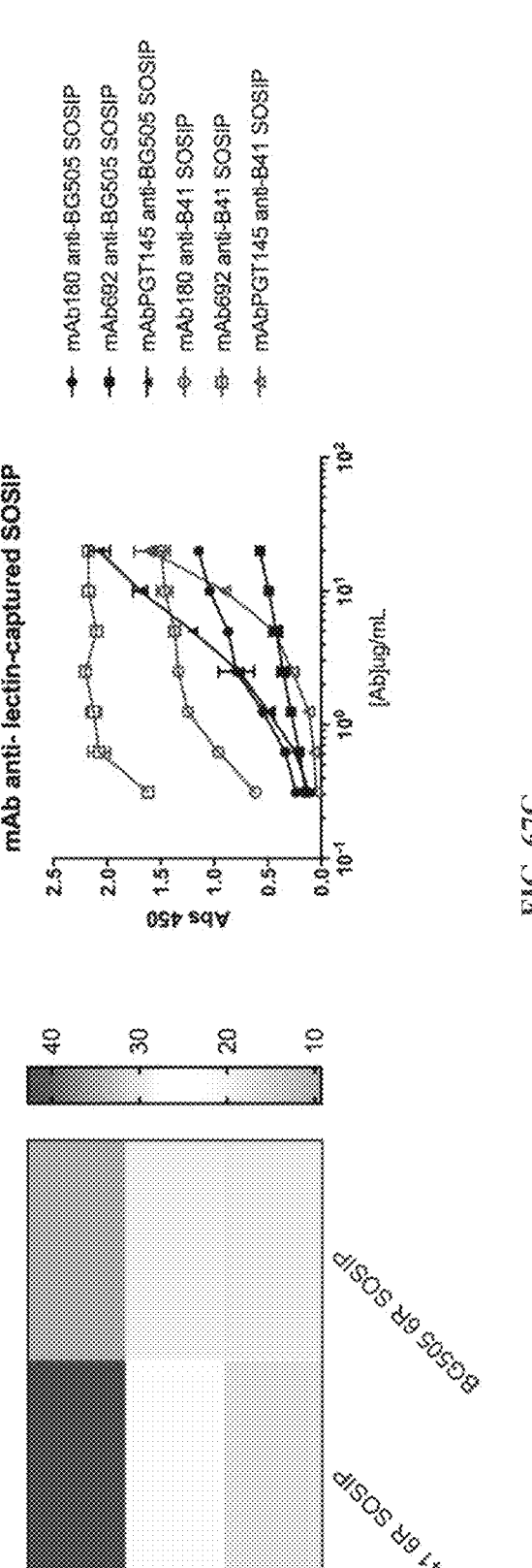

FIGS. 67A-67C show HIV/HCV cross-reactive antibody binding to HIV and HCV antigens as measured by lectin capture ELISA with antigens shown. In FIG. 67A, all antigens anti-AVITAG™ captured, blocked in 1% BSA and incubated at 37° C. In FIG. 67B, all antigens anti-AVITAG™ captured, blocked in 5% FBS and incubated at RT. In FIG. 67C, all antigens were lectin-captured, blocked in 5% FBS and incubated at RT.

Figure 68:
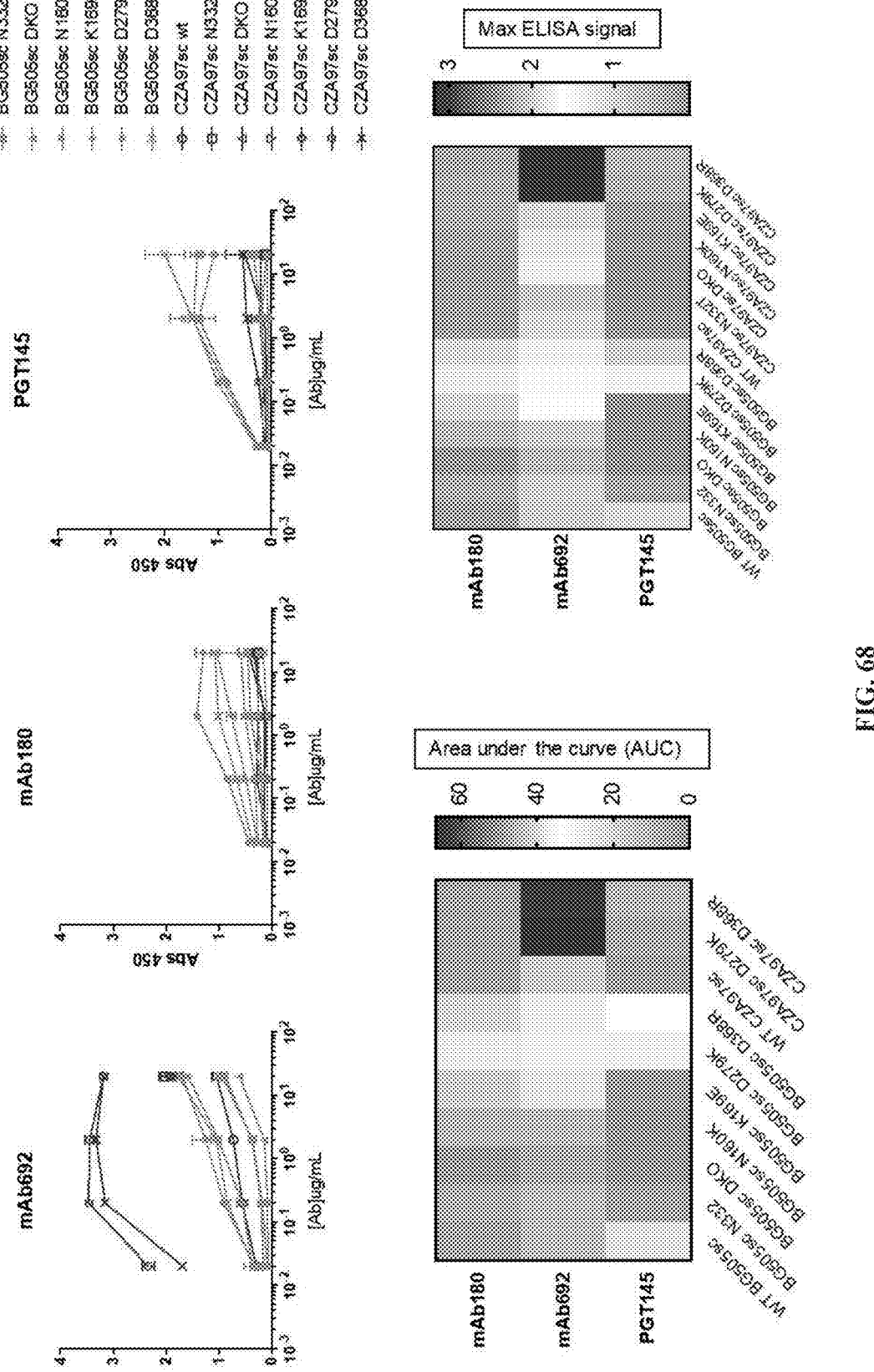

FIG. 68 shows HIV/HCV cross-reactive antibody binding to epitope knockout antigens to define where on the viral structure these antibodies bind. All antigens anti-AVITAG™ captured, blocked in 5% FBS and incubated at RT.

FIG. 69 shows HIV/HCV cross-reactive antibody binding to natively glycosylated and PNGase de-glycosylated HIV and HCV antigens.

FIG. 70 shows polyreactivity ELISA tests of mAb180 lineage members.

FIG. 71 shows mAb692 and relatives binding patterns.

Figure 72:
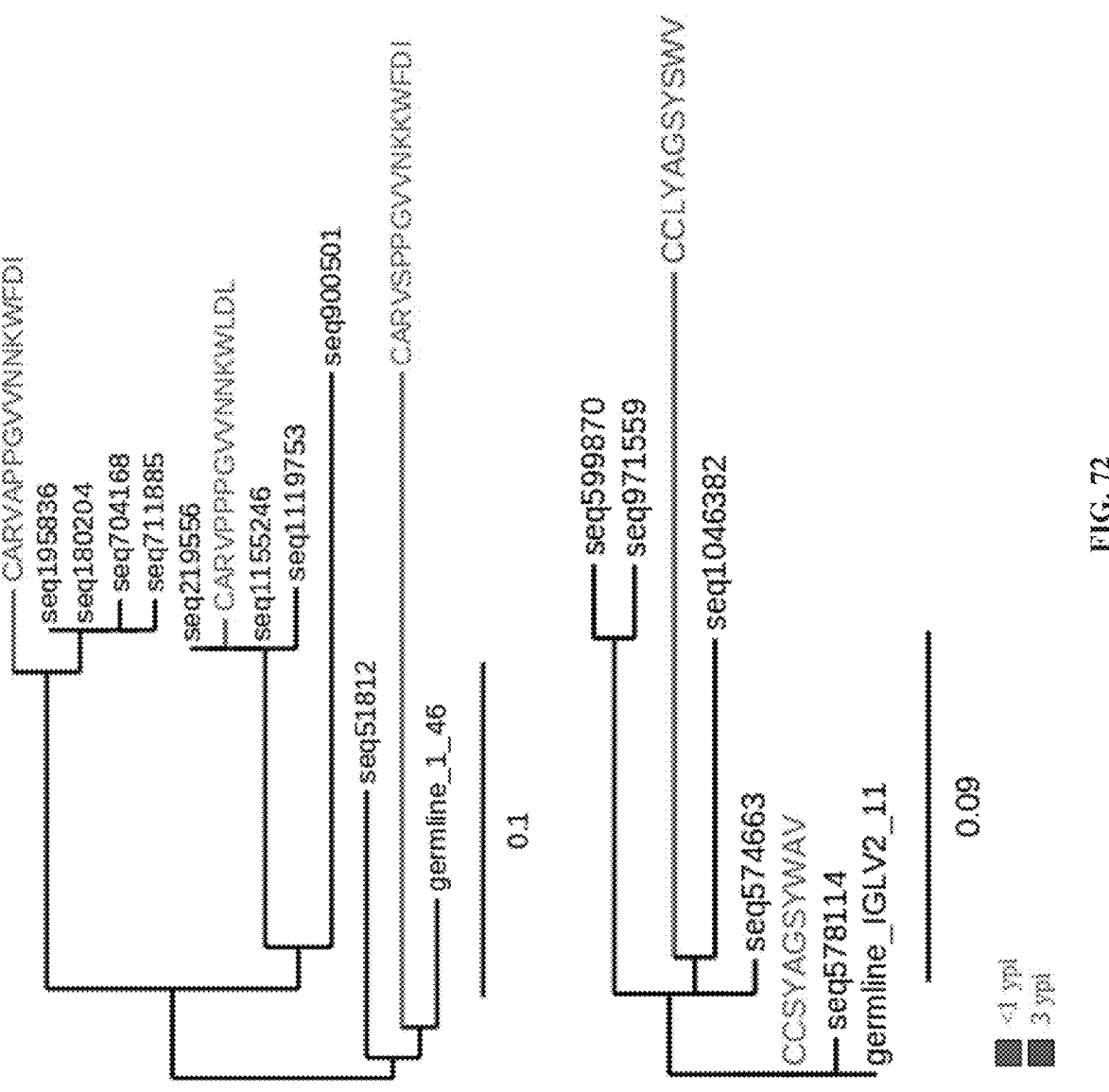

FIG. 72 shows mAb692 lineage tracing from <1 ypi. HIV/HCV cross-reactive antibodies identified in previous figures are shown in red. All other sequences in the tree are from 0.79ypi which were identified using unpaired NGS (ARCHER™ BCR IMMUNOVERSE™ kit). Sequences in FIG. 72: CARVAPPGVVNNKWFDI (SEQ ID NO: 13148); CARVPPPGVVNNKWLDL (SEQ ID NO: 13149); CARVSPPGVVNKKWFDI (SEQ ID NO: 13150); CCLY-AGSYSWV (SEQ ID NO: 13151); CCSYAGSYWAV (SEQ ID NO: 13152).

Figure 73A:
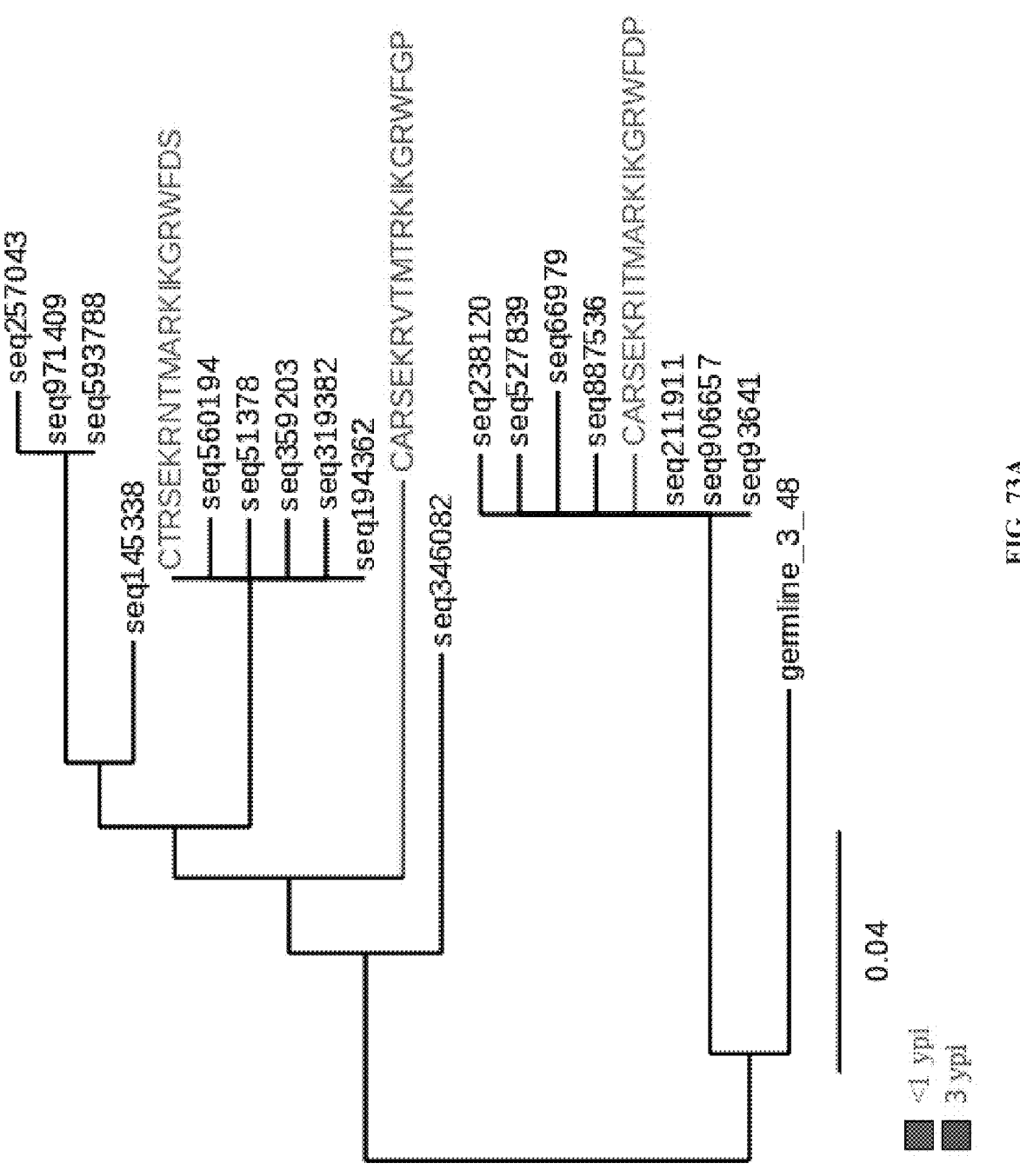
Figure 73B:
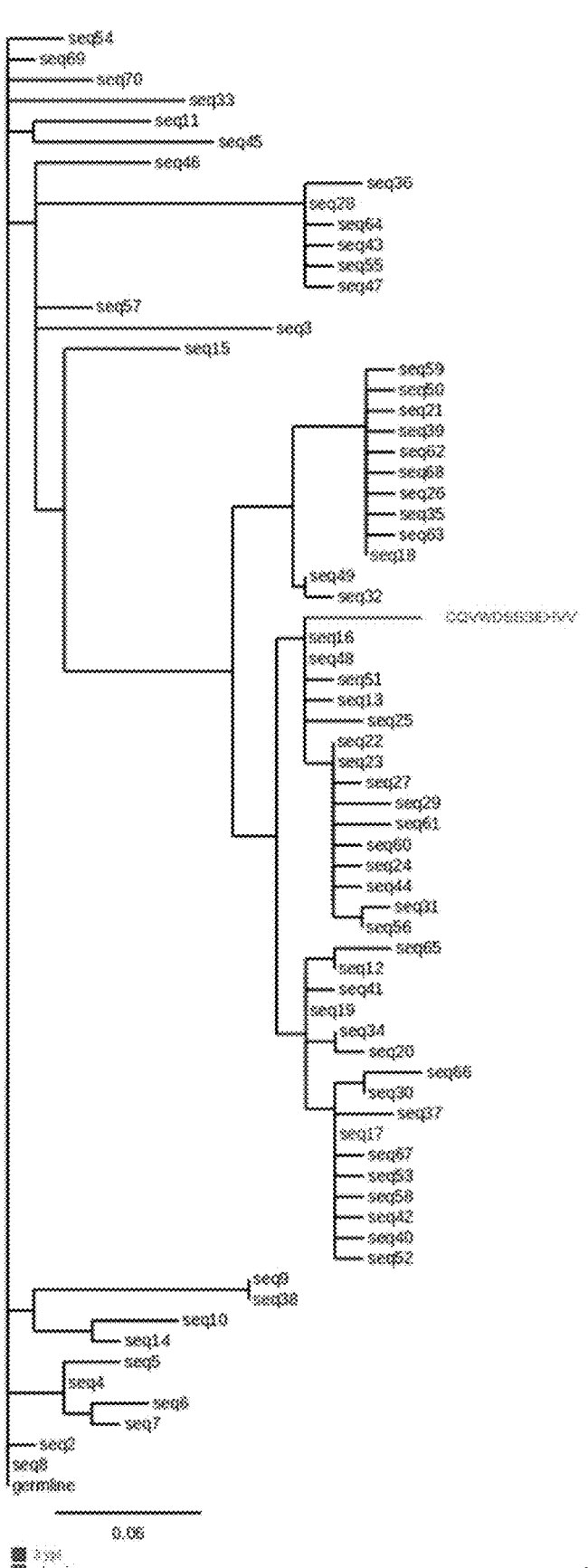

FIGS. 73A-73B show mAb180 lineage tracing from <1 ypi. HIV/HCV cross-reactive antibodies identified in previous figures are shown in red. All other sequences in the tree are from 0.79ypi which were identified using unpaired NGS (ARCHER™ BCR IMMUNOVERSE™ kit).

FIG. 73A shows the sequence development of mAb180 heavy chain and FIG. 73B shows mAb180 light chain. These figures were generated as maximum likelihood phylogenetic trees using PhyML. Sequences in FIG. 73A: CTRSEKRN-TMARKIKGRWFDS (SEQ ID NO: 13153); CARSEKRVTMTRKIKGRWFGP (SEQ ID NO: 13154); CARSEKRITMARKIKGRWFDP (SEQ ID NO: 13155). Sequences in FIG. 73B: CQVWDSSSEHVV (SEQ ID NO: 1888).

Figures 74A, 74B:
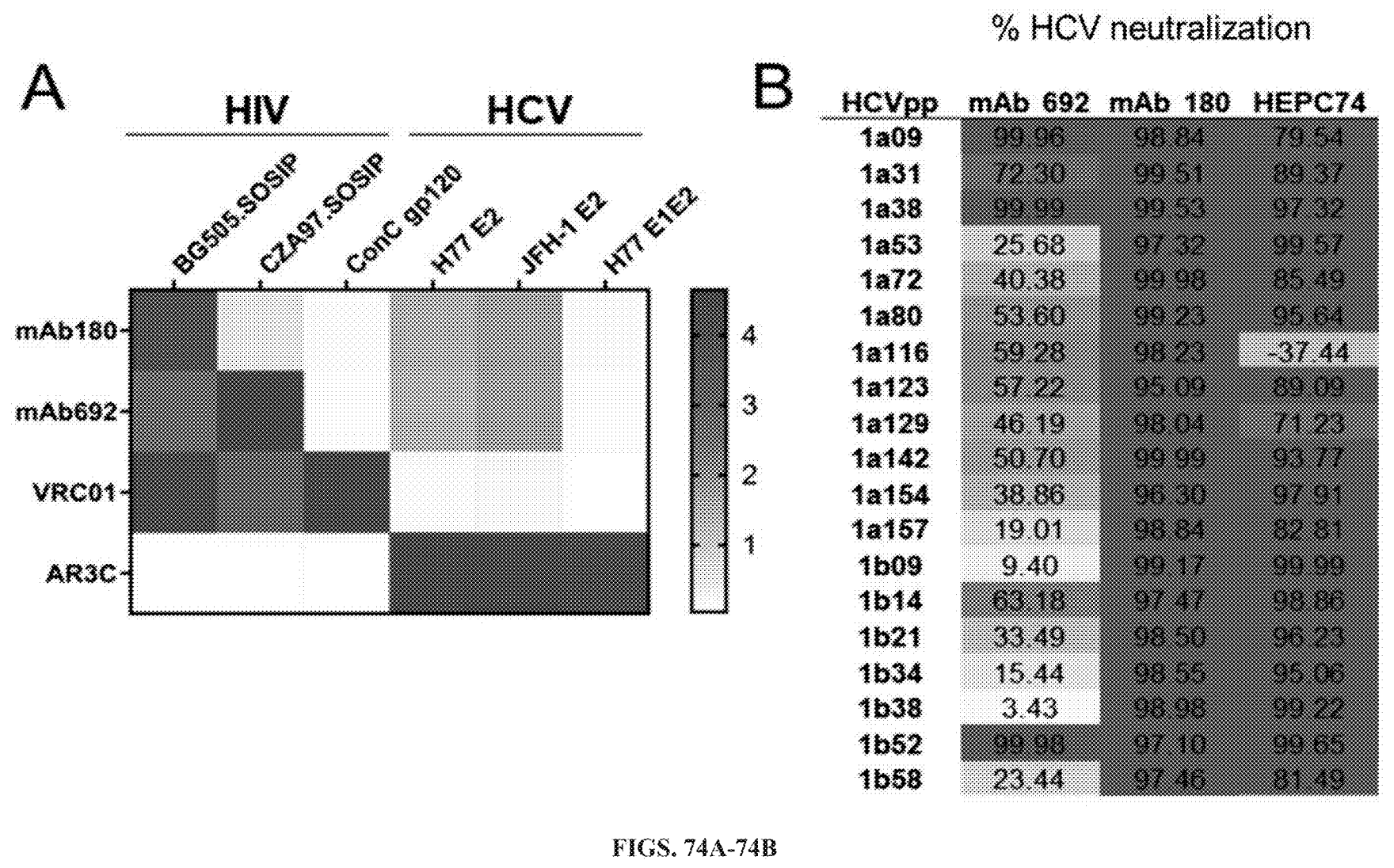

FIGS. 74A-74B show mAbs 180 and 692 show cross-reactive binding and HCV neutralization. FIG. 74A shows newly identified mAbs 180 and 692 cross-reactive binding confirmed by ELISA (heatmap of average Abs450 values at 20 μg/ml ab, from duplicates); VRC01 (HIV) and AR3C (HCV) are shown as controls. FIG. 74B shows exceptional HCV neutralization breadth for mAb 180 against a panel of 19 HCV pseudoparticles, shown as % neutralized virus at 100 μg/ml ab. The prior broadest known HEPC74 neutralization antibody is shown as a control.

Figure 75:
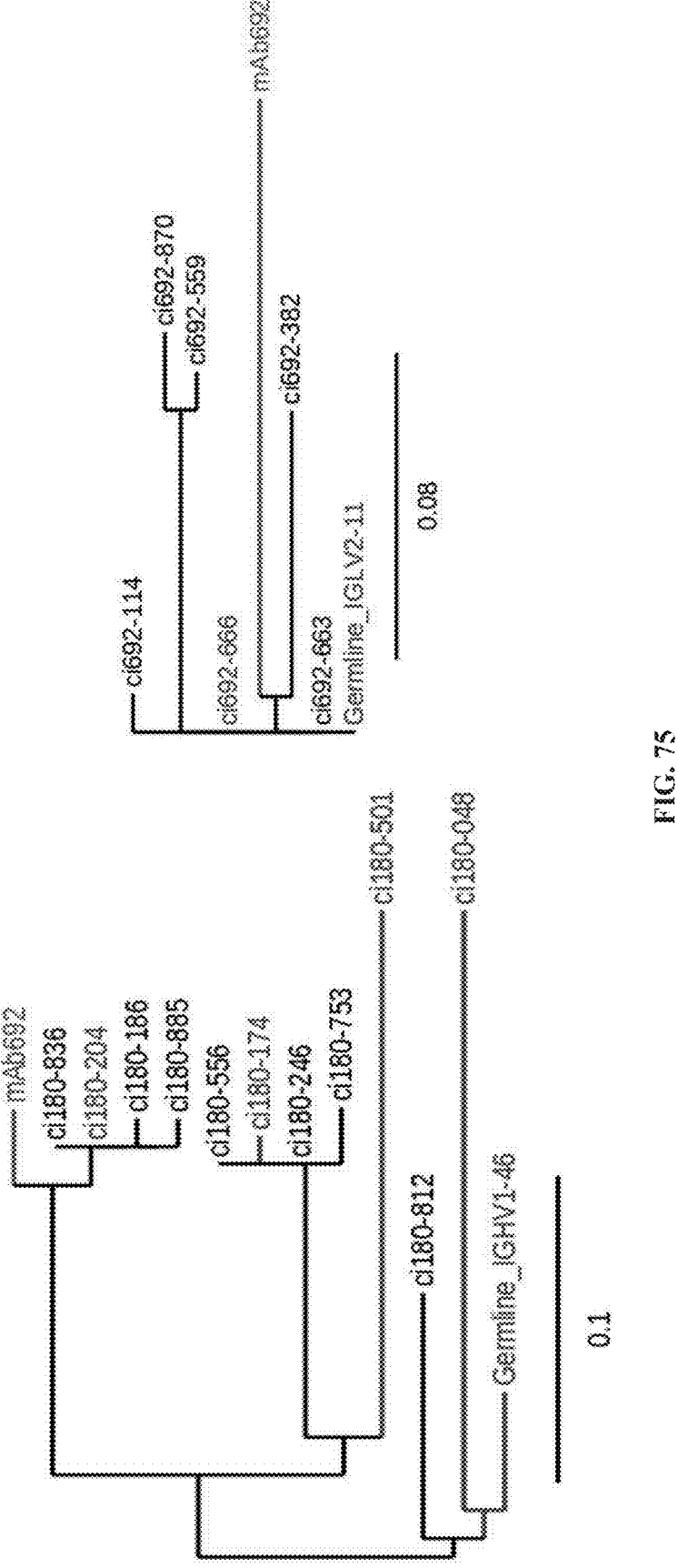

FIG. 75 shows mAb692 evolution.

DETAILED DESCRIPTION

HIV/HCV co-infection is remarkably common, affecting 4-5 million people worldwide. Shared routes of transmission and high endemic areas contribute to high rates of re-infection and rapid viral spread. While the global health burden of these viruses has been lessened significantly by the advent of highly active antiretroviral therapy (HAART) and direct-acting antivirals (DAA) for HIV and HCV respectively, these therapies are expensive and require high patient compliance to often complex drug regimens, leading to questions of their realistic efficacy. Given this, developing novel therapeutics and vaccines remains a world health priority.

Utilized primarily for their incredible specificity, polyreactive antibodies can confer a selective advantage in the fight against highly mutable pathogens such as HIV and HCV. Current antibody-based vaccine design efforts are focused on eliciting broadly neutralizing antibodies (bNAbs), yet how these multi-specific antibodies are elicited remains unclear. To interrogate the limits of this viral polyreactivity, virus-specific antibody responses in HIV/HCV coinfection are investigated. In order to identify HIV/HCV cross-reactive antibodies, antigen-specific B cell sorting of infected peripheral blood mononuclear cells were used. Using fluorescence-activated cell sorting with fluorescently-labeled antigen probes, multiple antibodies that recognize both HIV and HCV envelope proteins with varying binding strengths were identified. The current disclosure shows the first evidence of antibody cross-reactivity across virus species.

Therefore, in some aspects, disclosed herein are recombinant antibodies that specifically binds a viral protein of HIV and/or a viral protein of HCV and uses thereof for treating/preventing/inhibiting/reducing HIV/HCV co-infection, as well as HIV and HCV mono-infections.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

The term "about" as used herein when referring to a measurable value such as an amount, a percentage, and the like, is meant to encompass variations of ±20%, ±10%, ±5%, or ±1% from the measurable value.

"Administration" to a subject or "administering" includes any route of introducing or delivering to a subject an agent. Administration can be carried out by any suitable route, including oral, intravenous, intraperitoneal, intranasal, inhalation and the like. Administration includes self-administration and the administration by another.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

As used herein, the term "antigen" refers to a molecule that is capable of binding to an antibody. In some embodiments, the antigen stimulates an immune response such as by production of antibodies specific for the antigen.

In the present invention, "specific for" and "specificity" means a condition where one of the molecules is involved in selective binding. Accordingly, an antibody that is specific for one antigen selectively binds that antigen and not other antigens.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. The antibodies can be tested for their desired activity using the in vitro assays described herein, or by analogous methods, after which their in vivo therapeutic and/or prophylactic activities are tested according to known clinical testing methods. Native antibodies are usually heterotetrameric glycoproteins of about 150,000 daltons, composed of two identical light (L) chains and two identical heavy (H) chains. Each heavy chain has at one end a variable domain (VH) followed by a number of constant domains. Each light chain has a variable domain at one end (VL) and a constant domain at its other end. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

Each antibody molecule is made up of the protein products of two genes: heavy-chain gene and light-chain gene. The heavy-chain gene is constructed through somatic recombination of V, D, and J gene segments. In human, there are 51 VH, 27 DH, 6 JH, 9 CH gene segments on human chromosome 14. The light-chain gene is constructed through somatic recombination of V and J gene segments. There are 40 Vκ, 31 Vλ, 5 Jκ, 4 Jλ gene segments on human chromosome 14 (80 VJ). The heavy-chain constant domains that correspond to the different classes of immunoglobulins are called α, δ, ε, γ, and μ, respectively. The "light chains" of antibodies from any vertebrate species can be assigned to one of two clearly distinct types, called kappa (κ) and lambda (λ), based on the amino acid sequences of their constant domains.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or antigen binding fragment thereof" or "antibody or fragments thereof" encompasses chimeric antibodies and hybrid antibodies, with dual or multiple antigen or epitope specificities, and fragments, such as F(ab')2, Fab', Fab, Fv, sFv, scFv, nano-antibody and the like, including hybrid fragments. Thus, fragments of the antibodies that retain the ability to bind their specific antigens are provided. Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The terms "antigen binding site", "binding site" and "binding domain" refer to the specific elements, parts or amino acid residues of a polypeptide, such as an antibody, that bind the antigenic determinant or epitope.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, K and A light chains refer to the two major antibody light chain isotypes.

The term "CDR" as used herein refers to the "complementarity determining regions" of the antibody which consist of the antigen binding loops. (Kabat E. A. et al., (1991) Sequences of proteins of immunological interest. NIH Publication 91-3242). Each of the two variable domains of an antibody Fv fragment contain, for example, three CDRs.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. The amino acid sequence boundaries of a CDR can be determined by one of skill in the art using any of a number of known numbering schemes, including those described by Kabat et al., supra ("Kabat" numbering scheme): Al-Lazikani et al., 1997. J. Mol. Biol., 273:927-948 ("Chothia" numbering scheme); MacCallum et al., 1996, J. Mol. Biol, 262:732-745 ("Contact" numbering scheme); Lefranc et al., Dev. Comp. Immunol., 2003, 27:55-77 ("IMGT" numbering scheme); and Honegge and Pluckthun, J. Mol. Biol., 2001, 309:657-70 ("AHo" numbering scheme); each of which is incorporated by reference in its entirety.

"Composition" refers to any agent that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, a bacterium, a vector, polynucleotide, cells, salts, esters, amides, proagents, active metabolites, isomers, fragments, analogs, and the like. When the term "composition" is used, then, or when a particular composition is specifically identified, it is to be understood that the term includes the composition per se as well as pharmaceutically acceptable, pharmacologically active vector, polynucleotide, salts, esters, amides, proagents, conjugates, active metabolites, isomers, fragments, analogs, etc. In some aspects, the composition disclosed herein comprises a recombinant antibody that specifically binds to a HIV and/or HCV antigen.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition. The severity of a disease or disorder, as well as the ability of a treatment to prevent, treat, or mitigate, the disease or disorder can be measured, without implying any limitation, by a biomarker or by a clinical parameter. In some embodiments, the term "effective amount of a recombinant antibody" refers to an amount of a recombinant antibody sufficient to prevent, treat, or mitigate a HIV/HCV coinfection, HIV mono-infection, and/or HCV mono-infection.

The "fragments" or "functional fragments," whether attached to other sequences or not, can include insertions, deletions, substitutions, or other selected modifications of particular regions or specific amino acids residues, provided the activity of the fragment is not significantly altered or impaired compared to the nonmodified peptide or protein. These modifications can provide for some additional property, such as to remove or add amino acids capable of disulfide bonding, to increase its bio-longevity, to alter its secretory characteristics, etc. In any case, the functional fragment must possess a bioactive property, such as binding to HIV and/or HCV antigen, and/or ameliorating the viral infection.

The term "identity" or "homology" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conservative substitutions as part of the sequence identity. A polynucleotide or polynucleotide region (or a polypeptide or polypeptide region) that has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art. Such alignment can be provided using, for instance, the method of Needleman et al. (1970) J. Mol. Biol. 48:443-453, implemented conveniently by computer programs such as the Align program (DNAstar, Inc.).

The term "increased" or "increase" as used herein generally means an increase by a statically significant amount;

for example, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "nanobody", "$V_HH$", "$V_HH$ antibody fragment" and "single domain antibody" are used indifferently and designate a variable domain of a single heavy chain of an antibody of the type found in Camelidae, which are without any light chains, such as those derived from Camelids as described in PCT Publication No. WO 94/04678, which is incorporated by reference in its entirety.

The term "reduced", "reduce", "reduction", or "decrease" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

"Nucleotide," "nucleoside," "nucleotide residue," and "nucleoside residue," as used herein, can mean a deoxyribonucleotide, ribonucleotide residue, or another similar nucleoside analogue. A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

The method and the system disclosed here including the use of primers, which are capable of interacting with the disclosed nucleic acids, such as the antigen barcode as disclosed herein. In certain embodiments the primers are used to support DNA amplification reactions. Typically, the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically, the disclosed primers hybridize with the disclosed nucleic acids or region of the nucleic acids or they hybridize with the complement of the nucleic acids or complement of a region of the nucleic acids.

The term "amplification" refers to the production of one or more copies of a genetic fragment or target sequence, specifically the "amplicon". As it refers to the product of an amplification reaction, amplicon is used interchangeably with common laboratory terms, such as "PCR product."

The term "polypeptide" refers to a compound made up of a single chain of D- or L-amino acids or a mixture of D- and L-amino acids joined by peptide bonds.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g. a foreign gene) can be introduced into a host cell, so as to transform the host and promote expression (e.g. transcription and translation) of the introduced sequence.

The term "host cell" as used herein shall refer to primary subject cells trans-formed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "gene" or "gene sequence" refers to the coding sequence or control sequence, or fragments thereof. A gene may include any combination of coding sequence and control sequence, or fragments thereof. Thus, a "gene" as referred to herein may be all or part of a native gene. A polynucleotide sequence as referred to herein may be used interchangeably with the term "gene", or may include any coding sequence, non-coding sequence or control sequence, fragments thereof, and combinations thereof. The term "gene" or "gene sequence" includes, for example, control sequences upstream of the coding sequence (for example, the ribosome binding site).

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, New Jersey), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

The term "specificity" refers to the number of different types of antigens or antigenic determinants to which a particular antigen-binding molecule (such as the recombinant antibody of the invention) can bind. As used herein, the term "specifically binds," as used herein with respect to a recombinant antibody refers to the recombinant antibody's preferential binding to one or more epitopes as compared with other epitopes. Specific binding can depend upon binding affinity and the stringency of the conditions under which the binding is conducted. In one example, an antibody specifically binds an epitope when there is high affinity binding under stringent conditions.

It should be understood that the specificity of an antigen-binding molecule (e.g., the recombinant antibodies of the present invention) can be determined based on affinity and/or avidity. The affinity, represented by the equilibrium constant for the dissociation of an antigen with an antigen-binding molecule ($K_D$), is a measure for the binding strength between an antigenic determinant and an antigen-binding site on the antigen-binding molecule: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as the recombinant antibodies of the present invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the recombinant antibodies of the invention) will bind to their antigen with a dissociation constant ($K_D$) of $10^{-5}$ to $10^{-12}$ moles/liter or less, and preferably $10^{-7}$ to $10^{-12}$ moles/liter or less, and more preferably $10^{-8}$ to $10^{-12}$ moles/liter.

"Therapeutically effective amount" refers to the amount of a composition such as recombinant antibody that will elicit the biological or medical response of a tissue, system, animal, or human that is being sought by the researcher, veterinarian, medical doctor or other clinician over a generalized period of time. In some embodiments, a desired response is reduction of HIV and/or HCV titers in a subject. In some embodiments, the desired response is mitigation of HIV/HCV co-infection or HIV/HCV mono-infection and/or related symptoms. In some instances, a desired biological or medical response is achieved following administration of multiple dosages of the composition to the subject over a period of days, weeks, or years. The therapeutically effective amount will vary depending on the composition, the disorder or conditions and its severity, the route of administration, time of administration, rate of excretion, drug combination, judgment of the treating physician, dosage form, and the age, weight, general health, sex and/or diet of the subject to be treated. The therapeutically effective amount of recombinant antibodies as described herein can be determined by one of ordinary skill in the art.

A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, such as decreased viral titers, decreased viral RNA levels, increase in CD4 T lymphocyte counts, and/or prolonged survival of a subject. It will be understood, that the total daily usage of the compositions and formulations as disclosed herein will be decided by the attending physician within the scope of sound medical judgment. The exact amount required will vary depending on factors such as the type of disease being treated.

The terms "treat," "treating," "treatment," and grammatical variations thereof as used herein, include partially or completely delaying, alleviating, mitigating or reducing the intensity of one or more attendant symptoms of a cancer or condition and/or alleviating, mitigating or impeding one or more causes of a cancer. Treatments according to the invention may be applied preventively, prophylactically, palliatively or remedially. Prophylactic treatments are administered to a subject prior to onset (e.g., before obvious signs of an infection), during early onset (e.g., upon initial signs and symptoms of an infection), after an established development of an infection, or during chronic infection. Prophylactic administration can occur for several minutes to months prior to the manifestation of an infection.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

Antibodies and Compositions

In some aspects, disclosed herein is a recombinant antibody, said antibody comprising a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein CDRL3 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to

```
                                    (SEQ ID NO: 13)
    MQPLQLPDT, (SEQ ID NO: 25)
    QQSYNVPT, (SEQ ID NO: 39)
    HQSSSLPFT, (SEQ ID NO: 49)
    QHFYSSPPT, (SEQ ID NO: 88)
    CLYAGSYSWV,
    or (SEQ ID NO: 101)
    QVWDSSSEHVV;
``` and/or

CDRH3 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to

```
                                    (SEQ ID NO: 104)
    ARVAPPGVVNNKWFDI, (SEQ ID NO: 110)
    ARSEKRVTMTRKIKGRWFGP, (SEQ ID NO: 1817)
    CAAGLWSGDLSRPRYSDSW, (SEQ ID NO: 1818)
    CAKGLTTESRLEFW, (SEQ ID NO: 1819)
    CVSSWGPESPYYFDYW,
    or (SEQ ID NO: 1820)
    CAREYCTGGDCHFFLDYW.
```

In some aspects, disclosed herein is a recombinant antibody, said antibody comprising a light chain variable region (VL) that comprises a light chain complementarity determining region (CDRL) 1, CDRL2, and CDRL3 or a heavy chain variable region (VH) that comprises a heavy chain complementarity determining region (CDRH) 1, CDRH2, and CDRH3, wherein CDRL3 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to

```
                              (SEQ ID NO: 13)
    MQPLQLPDT, (SEQ ID NO: 25)
    QQSYNVPT, (SEQ ID NO: 39)
    HQSSSLPFT, (SEQ ID NO: 49)
    QHFYSSPPT, (SEQ ID NO: 88)
    CLYAGSYSWV,
    or (SEQ ID NO: 101)
    QVWDSSSEHVV;
``` and/or

CDRH3 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to

```
                             (SEQ ID NO: 104)
    ARVAPPGVVNNKWFDI, (SEQ ID NO: 110)
    ARSEKRVTMTRKIKGRWFGP, (SEQ ID NO: 1817)
    CAAGLWSGDLSRPRYSDSW, (SEQ ID NO: 1818)
    CAKGLTTESRLEFW, (SEQ ID NO: 1819)
    CVSSWGPESPYYFDYW,
    or (SEQ ID NO: 1820)
    CAREYCTGGDCHFFLDYW.
```

In some embodiments, the CDRL3 comprises at least one amino acid substitution when compared to SEQ ID NO: 13, 25, 39, 49, 88, or 101. In some embodiments, the CDRL3 comprises at least 1, 2, 3, 4, 5, or 6 substitutions when compared to SEQ ID NO: 13. In some embodiments, the CDRL3 comprises at least 1, 2, 3, 4, 5, or 6 amino acid substitutions when compared to SEQ ID NO: 25. In some embodiments, the CDRL3 comprises at least 1, 2, 3, 4, 5, or 6 amino acid substitutions when compared to SEQ ID NO: 39. In some embodiments, the CDRL3 comprises at least 1, 2, 3, 4, 5, or 6 amino acid substitutions when compared to SEQ ID NO: 49. In some embodiments, the CDRL3 comprises at least 1, 2, 3, 4, 5, or 6 amino acid substitutions when compared to SEQ ID NO: 88. In some embodiments, the CDRL3 comprises at least 1, 2, 3, 4, 5, or 6 amino acid substitutions when compared to 101.

In some embodiments, the at least one amino acid substitution is selected from the group consisting of a) at position 1 when compared to SEQ ID NO: 13, wherein the substituting amino acid residue is K;

b) at position 3 when compared to SEQ ID NO: 13, wherein the substituting amino acid residue is selected from the group consisting of A, T, G, V, D, Y, and F;

c) at position 6 when compared to SEQ ID NO: 13, wherein the substituting amino acid residue is selected from the group consisting of H, S, T, P, I, V, P, R, and V;

d) at position 9 when compared to SEQ ID NO: 13, wherein the substituting amino acid residue is selected from the group consisting of Y, L, H, P, I, G, C, J, R, and Q;

e) at position 5 when compared to SEQ ID NO: 25, wherein the substituting amino acid residue is selected from the group consisting of T, P, Y, R, I, G, and S;

f) at position 6 when compared to SEQ ID NO: 25, wherein the substituting amino acid residue is selected from the group consisting of A, T, and P;

g) at position 7 when compared to SEQ ID NO: 25, wherein the substituting amino acid residue is selected from the group consisting of W, A, R, G and L;

h) at position 3 when compared to SEQ ID NO: 39, wherein the substituting amino acid residue is T;

i) at position 4 when compared to SEQ ID NO: 39, wherein the substituting amino acid residue is selected from the group consisting of R, G, T, Y, A, and K;

j) at position 6 when compared to SEQ ID NO: 39, wherein the substituting amino acid residue is F;

k) at position 7 when compared to SEQ ID NO: 39, wherein the substituting amino acid residue is selected from the group consisting of G, Q, L, and S.

l) at position 8 when compared to SEQ ID NO: 39, wherein the substituting amino acid residue is selected from the group consisting of G, Q, Y, W, H, and L;

m) at position 9 when compared to SEQ ID NO: 39, wherein the substituting amino acid residue is selected from the group consisting of A, P, and S.

n) at position 3 when compared to SEQ ID NO: 49, wherein the substituting amino acid residue is L;

o) at position 5 when compared to SEQ ID NO: 49, wherein the substituting amino acid residue is T;

p) at position 6 when compared to SEQ ID NO: 49, wherein the substituting amino acid residue is selected from the group consisting of N, D, and K;

q) at position 2 when compared to SEQ ID NO: 88, wherein the substituting amino acid residue is selected from the group consisting of S, P and T;

r) at position 6 when compared to SEQ ID NO: 88, wherein the substituting amino acid residue is R;

s) at position 8 when compared to SEQ ID NO: 88, wherein the substituting amino acid residue is selected from the group consisting of N, W, and T;

t) at position 9 when compared to SEQ ID NO: 88, wherein the substituting amino acid residue is A;

u) at position 2 when compared to SEQ ID NO: 101, wherein the substituting amino acid residue is selected from the group consisting of M, A, and L;

v) at position 3 when compared to SEQ ID NO: 101, wherein the substituting amino acid residue is C;

w) at position 4 when compared to SEQ ID NO: 101, wherein the substituting amino acid residue is Y;

x) at position 7 when compared to SEQ ID NO: 101, wherein the substituting amino acid residue is N; and y) at position 8 when compared to SEQ ID NO: 101, wherein the substituting amino acid residue is D.

Accordingly, in some embodiments, the recombinant antibody of any preceding aspect comprises a CDRL3 comprising an amino acid sequence selected from the group consisting of SEQ ID NOs: 1-12, 14-24, 26-38, 40-48, 50-87, and 89-100. In some embodiments, the recombinant antibody of any preceding aspect comprises a CDRL3 comprising an amino acid sequence selected from the group consisting of SEQ ID NOs: 1-12, 14-24, 26-38, 40-48, 50-51, and 89-100.

Accordingly, in some embodiments, the recombinant antibody disclosed herein comprises a VL that comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NOs: 119-1693. In some embodiments, the VL comprises an amino acid sequence selected from the group consisting of SEQ ID NOS: 119-1693.

In some embodiments, the recombinant antibody of any preceding aspect comprises a CDRL3 that comprises an amino acid sequence selected from SEQ ID NOs: 13, 25, 39, 49, 88, 101, and 1883-1888. In some embodiments, the CDRL3 comprises an amino acid sequence of SEQ ID NO: 13. In some embodiments, the CDRL3 comprises an amino acid sequence of SEQ ID NO: 25. In some embodiments, the CDRL3 comprises an amino acid sequence of SEQ ID NO: 39. In some embodiments, the CDRL3 comprises an amino acid sequence of SEQ ID NO: 49. In some embodiments, the CDRL3 comprises an amino acid sequence of SEQ ID NO: 88. In some embodiments, the CDRL3 comprises an amino acid sequence of SEQ ID NO: 101. In some embodiments, the CDRL3 comprises an amino acid sequence of SEQ ID NO: 1883. In some embodiments, the CDRL3 comprises an amino acid sequence of SEQ ID NO: 1884. In some embodiments, the CDRL3 comprises an amino acid sequence of SEQ ID NO: 1885. In some embodiments, the CDRL3 comprises an amino acid sequence of SEQ ID NO: 1886. In some embodiments, the CDRL3 comprises an amino acid sequence of SEQ ID NO: 1887. In some embodiments, the CDRL3 comprises an amino acid sequence of SEQ ID NO: 1888.

In some embodiments, the recombinant antibody of any preceding aspect comprises a CDRL1 that comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) selected from SEQ ID NOs: 13120-13125. In some embodiments, the recombinant antibody of any preceding aspect comprises a CDRL1 that comprises an amino acid sequence selected from SEQ ID NOs: 13120-13125. In some embodiments, the CDRL1 comprises an amino acid sequence of SEQ ID NO: 13120. In some embodiments, the CDRL1 comprises an amino acid sequence of SEQ ID NO: 13121. In some embodiments, the CDRL1 comprises an amino acid sequence of SEQ ID NO: 13122. In some embodiments, the CDRL1 comprises an amino acid sequence of SEQ ID NO: 13123. In some embodiments, the CDRL1 comprises an amino acid sequence of SEQ ID NO: 13124. In some embodiments, the CDRL1 comprises an amino acid sequence of SEQ ID NO: 13125.

In some embodiments, the recombinant antibody of any preceding aspect comprises a CDRL2 that comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) selected from SEQ ID NOs: 13126-13131. In some embodiments, the recombinant antibody of any preceding aspect comprises a CDRL2 that comprises an amino acid sequence selected from SEQ ID NOs: 13126-13131. In some embodiments, the CDRL2 comprises an amino acid sequence of SEQ ID NO: 13126. In some embodiments, the CDRL2 comprises an amino acid sequence of SEQ ID NO: 13127. In some embodiments, the CDRL2 comprises an amino acid sequence of SEQ ID NO: 13128. In some embodiments, the CDRL2 comprises an amino acid sequence of SEQ ID NO: 13129. In some embodiments, the CDRL2 comprises an amino acid sequence of SEQ ID NO: 13130. In some embodiments, the CDRL2 comprises an amino acid sequence of SEQ ID NO: 13131.

Accordingly, in some embodiments, the recombinant antibody disclosed herein comprises a VL that comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NOs: 119, 227, 242, 351, 1399, 1406, and 1899-1904. In some embodiments, the VL comprises an amino acid sequence selected from the group consisting of SEQ ID NOs: SEQ ID NOs: 119, 227, 242, 351, 1399, 1406, and 1899-1904.

In some embodiments, the recombinant antibody of any preceding aspect comprises a CDRH3, wherein the CDRH3 comprises at least one amino acid substitution when compared to SEQ ID NO: 104, 110, 1817, 1818, 1819, or 1820. In some embodiments, the CDRH3 comprises at least 1, 2, 3, 4, 5, or 6 substitutions when compared to SEQ ID NO: 104. In some embodiments, the CDRH3 comprises at least 1, 2, 3, 4, 5, or 6 amino acid substitutions when compared to SEQ ID NO: 110. In some embodiments, the CDRH3 comprises at least 1, 2, 3, 4, 5, or 6 amino acid substitutions when compared to SEQ ID NO: 1817. In some embodiments, the CDRH3 comprises at least 1, 2, 3, 4, 5, or 6 amino acid substitutions when compared to SEQ ID NO: 1818. In some embodiments, the CDRH3 comprises at least 1, 2, 3, 4, 5, or 6 amino acid substitutions when compared to SEQ ID NO: 1819. In some embodiments, the CDRH3 comprises at least 1, 2, 3, 4, 5, or 6 amino acid substitutions when compared to 1820.

In some embodiments, a CDR sequence (for example CDRL1, CDRL2, CDRL3, CDRH1, CDRH2, or CDRH3) comprises one amino acid mutation, two amino acid mutations, three amino acid mutations, four amino acid mutations, five amino acid mutations, etc. when compared to a CDR sequence as disclosed herein.

In some embodiments, the recombinant antibody is a monoclonal antibody. In some embodiments, the recombinant antibody is an isolated antibody. In some embodiments, the recombinant antibody is an antibody or antigen binding fragment thereof. In some embodiments, combinations of antibodies or antigen binding fragments thereof disclosed herein are used for treating HIV infection, HCV infection, or HIV/HCV co-infection.

In some embodiments, the at least one amino acid substitution is selected from the group consisting of a) at position 3 when compared to SEQ ID NO: 104, wherein the substituting amino acid residue is G or I;

b) at position 4 when compared to SEQ ID NO: 104, wherein the substituting amino acid residue is S, T, or P;

c) at position 9 when compared to SEQ ID NO: 104, wherein the substituting amino acid residue is A;

d) at position 11 when compared to SEQ ID NO: 104, wherein the substituting amino acid residue is K or H;

e) at position 14 when compared to SEQ ID NO: 104, wherein the substituting amino acid residue is L;

f) at position 16 when compared to SEQ ID NO: 104, wherein the substituting amino acid residue is L or T;

g) at position 1 when compared to SEQ ID NO: 110, wherein the substituting amino acid residue is T or S;

h) at position 5 when compared to SEQ ID NO: 110, wherein the substituting amino acid residue is N or P;

i) at position 7 when compared to SEQ ID NO: 110, wherein the substituting amino acid residue is I, N, K, or L;

j) at position 9 when compared to SEQ ID NO: 110, wherein the substituting amino acid residue is L or T;

k) at position 10 when compared to SEQ ID NO: 110, wherein the substituting amino acid residue is A or V;

l) at position 11 when compared to SEQ ID NO: 110, wherein the substituting amino acid residue is L.

m) at position 17 when compared to SEQ ID NO: 110, wherein the substituting amino acid residue is S;

n) at position 19 when compared to SEQ ID NO: 110, wherein the substituting amino acid residue is D; and o) at position 20 when compared to SEQ ID NO: 110, wherein the substituting amino acid residue is S.

Accordingly, in some embodiments, the recombinant antibody of any preceding aspect comprises a CDRH3 comprising an amino acid sequence selected from the group consisting of SEQ ID NOs: 102-103, 105-109, and 111-118.

Accordingly, in some embodiments, the recombinant antibody disclosed herein comprises a VH that comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NOs: 1694-1756. In some embodiments, the VL comprises an amino acid sequence selected from the group consisting of SEQ ID NOs: 1694-1756.

In some embodiments, the recombinant antibody of any preceding aspect comprises a CDRH3 that comprises an amino acid sequence selected from SEQ ID NOs: 104, 110, and 1817-1822. In some embodiments, the CDRH3 comprises an amino acid sequence of SEQ ID NO: 104. In some embodiments, the CDRH3 comprises an amino acid sequence of SEQ ID NO: 110. In some embodiments, the CDRH3 comprises an amino acid sequence of SEQ ID NO: 1817. In some embodiments, the CDRH3 comprises an amino acid sequence of SEQ ID NO: 1818. In some embodiments, the CDRH3 comprises an amino acid sequence of SEQ ID NO: 1819 In some embodiments, the CDRH3 comprises an amino acid sequence of SEQ ID NO: 1820. In some embodiments, the CDRH3 comprises an amino acid sequence of SEQ ID NO: 1821. In some embodiments, the CDRH3 comprises an amino acid sequence of SEQ ID NO: 1822.

In some embodiments, the recombinant antibody of any preceding aspect comprises a CDRH1 that comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) selected from SEQ ID NOs: 13102-13107. In some embodiments, the recombinant antibody of any preceding aspect comprises a CDRH1 that comprises an amino acid sequence selected from SEQ ID NOs: 13102-13107. In some embodiments, the CDRH1 comprises an amino acid sequence of SEQ ID NO: 13102. In some embodiments, the CDRH1 comprises an amino acid sequence of SEQ ID NO: 13103. In some embodiments, the CDRH1 comprises an amino acid sequence of SEQ ID NO: 13104. In some embodiments, the CDRH1 comprises an amino acid sequence of SEQ ID NO: 13105. In some embodiments, the CDRH1 comprises an amino acid sequence of SEQ ID NO: 13106. In some embodiments, the CDRH1 comprises an amino acid sequence of SEQ ID NO: 13107.

In some embodiments, the recombinant antibody of any preceding aspect comprises a CDRH2 that comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) selected from SEQ ID NOs: 13108-13113. In some embodiments, the recombinant antibody of any preceding aspect comprises a CDRH2 that comprises an amino acid sequence selected from SEQ ID NOs: 13108-13113. In some embodiments, the CDRH2 comprises an amino acid sequence of SEQ ID NO: 13108. In some embodiments, the CDRH2 comprises an amino acid sequence of SEQ ID NO: 13109. In some embodiments, the CDRH2 comprises an amino acid sequence of SEQ ID NO: 13110. In some embodiments, the CDRH2 comprises an amino acid sequence of SEQ ID NO: 13111. In some embodiments, the CDRH2 comprises an amino acid sequence of SEQ ID NO: 13112. In some embodiments, the CDRH2 comprises an amino acid sequence of SEQ ID NO: 13113.

In some embodiments, the CDRH3 comprises an amino acid sequence selected from the group consisting of SEQ ID NOs: 13138-13143, 13148-13150, and 13153-13155.

In some embodiments, the CDRL3 comprises an amino acid sequence selected from the group consisting of SEQ ID NOs: 13151 and 13152.

In some embodiments, the recombinant antibody disclosed herein comprises an amino acid sequence selected from SEQ ID NOs: 13144, 13145, 13146, and 13147.

Accordingly, in some embodiments, the recombinant antibody disclosed herein comprises a VH that comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NOs: 1895-1898, 1694, and 1718. In some embodiments, the VH comprises an amino acid sequence selected from the group consisting of SEQ ID NOs: SEQ ID NOs: 1895-1898, 1694, and 1718.

In some embodiments, disclosed herein is a recombinant antibody that is selected from the group consisting of a) a recombinant antibody comprising the CDRL3 of SEQ ID NO: 88 or 1887 and the CDRH3 of SEQ ID NO: 104 or 1821;

b) a recombinant antibody comprising the CDRL3 of SEQ ID NO: 101 or 1888 and the CDRH3 of SEQ ID NO: 110 or 1822;

c) a recombinant antibody comprising the CDRL3 of SEQ ID NO: 13 or 1883 and the CDRH3 of SEQ ID NO: 1817;

d) a recombinant antibody comprising the CDRL3 of SEQ ID NO: 25 or 1884 and the CDRH3 of SEQ ID NO: 1818;

e) a recombinant antibody comprising the CDRL3 of SEQ ID NO: 39 or 1885 and the CDRH3 of SEQ ID NO: 1819; and f) a recombinant antibody comprising the CDRL3 of SEQ ID NO: 49 or 1886 and the CDRH3 of SEQ ID NO: 1820.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13102,
CDRH2 is SEQ ID NO: 13108,
CDRH3 is SEQ ID NO: 1817,
CDRL1 is SEQ ID NO: 13120,
CDRL2 is SEQ ID NO: 13126, and
CDRL3 is SEQ ID NO: 13 or 1883.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13103,
CDRH2 is SEQ ID NO: 13109,
CDRH3 is SEQ ID NO: 1818,
CDRL1 is SEQ ID NO: 13121,
CDRL2 is SEQ ID NO: 13127, and
CDRL3 is SEQ ID NO: 25 or 1884.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13104,
CDRH2 is SEQ ID NO: 13110,
CDRH3 is SEQ ID NO: 1819,
CDRL1 is SEQ ID NO: 13122,
CDRL2 is SEQ ID NO: 13128, and
CDRL3 is SEQ ID NO: 39 or 1885.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13105,
CDRH2 is SEQ ID NO: 13111,
CDRH3 is SEQ ID NO: 1820,
CDRL1 is SEQ ID NO: 13123,
CDRL2 is SEQ ID NO: 13129, and
CDRL3 is SEQ ID NO: 49 or 1886.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13106,
CDRH2 is SEQ ID NO: 13112,
CDRH3 is SEQ ID NO: 104 or 1821,
CDRL1 is SEQ ID NO: 13124,
CDRL2 is SEQ ID NO: 13130, and
CDRL3 is SEQ ID NO: 88 or 1887.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13107,
CDRH2 is SEQ ID NO: 13113,
CDRH3 is SEQ ID NO: 110 or 1822,
CDRL1 is SEQ ID NO: 13125,
CDRL2 is SEQ ID NO: 13131, and
CDRL3 is SEQ ID NO: 101 or 1888.

In some embodiments, the recombinant antibody of any preceding aspect further comprises a framework region (FWR) 1, FWR2, FWR3, and/or FWR4.

In some embodiments, the recombinant antibody of any preceding aspect, wherein the FWRH1 is encoded by a polynucleotide comprising a nucleic acid sequence selected from SEQ ID NOs: 3881-4334.

In some embodiments, the recombinant antibody of any preceding aspect, wherein the FWRH2 is encoded by a polynucleotide comprising a nucleic acid sequence selected from SEQ ID NOs: 4335-4793.

In some embodiments, the recombinant antibody of any preceding aspect, wherein the FWRH3 is encoded by a polynucleotide comprising a nucleic acid sequence selected from SEQ ID NOs: 4794-5346.

In some embodiments, the recombinant antibody of any preceding aspect, wherein the FWRH4 is encoded by a polynucleotide comprising a nucleic acid sequence selected from SEQ ID NOs: 5347-5576.

In some embodiments, the recombinant antibody of any preceding aspect, wherein the CDRH1 is encoded by a polynucleotide comprising a nucleic acid sequence selected from SEQ ID NOs: 5577-6052.

In some embodiments, the recombinant antibody of any preceding aspect, wherein the CDRH2 is encoded by a polynucleotide comprising a nucleic acid sequence selected from SEQ ID NOs: 6053-6533.

In some embodiments, the recombinant antibody of any preceding aspect, wherein the CDRH3 is encoded by a polynucleotide comprising a nucleic acid sequence selected from SEQ ID NOs: 6534-7770.

In some embodiments, the recombinant antibody of any preceding aspect, wherein the FWRL1 is encoded by a polynucleotide comprising a nucleic acid sequence selected from SEQ ID NOs: 9190-9645.

In some embodiments, the recombinant antibody of any preceding aspect, wherein the FWRL2 is encoded by a polynucleotide comprising a nucleic acid sequence selected from SEQ ID NOs: 9646-10150.

In some embodiments, the recombinant antibody of any preceding aspect, wherein the FWRL3 is encoded by a polynucleotide comprising a nucleic acid sequence selected from SEQ ID NOs: 10151-10734.

In some embodiments, the recombinant antibody of any preceding aspect, wherein the FWRL4 is encoded by a polynucleotide comprising a nucleic acid sequence selected from SEQ ID NOs: 10735-11022.

In some embodiments, the recombinant antibody of any preceding aspect, wherein the CDRL1 is encoded by a polynucleotide comprising a nucleic acid sequence selected from SEQ ID NOs: 11023-11522.

In some embodiments, the recombinant antibody of any preceding aspect, wherein the CDRL2 is encoded by a polynucleotide comprising a nucleic acid sequence selected from SEQ ID NOs: 11523-11766.

In some embodiments, the recombinant antibody of any preceding aspect, wherein the CDRL3 is encoded by a polynucleotide comprising a nucleic acid sequence selected from SEQ ID NOs: 11767-13101.

Figures 27, 28:
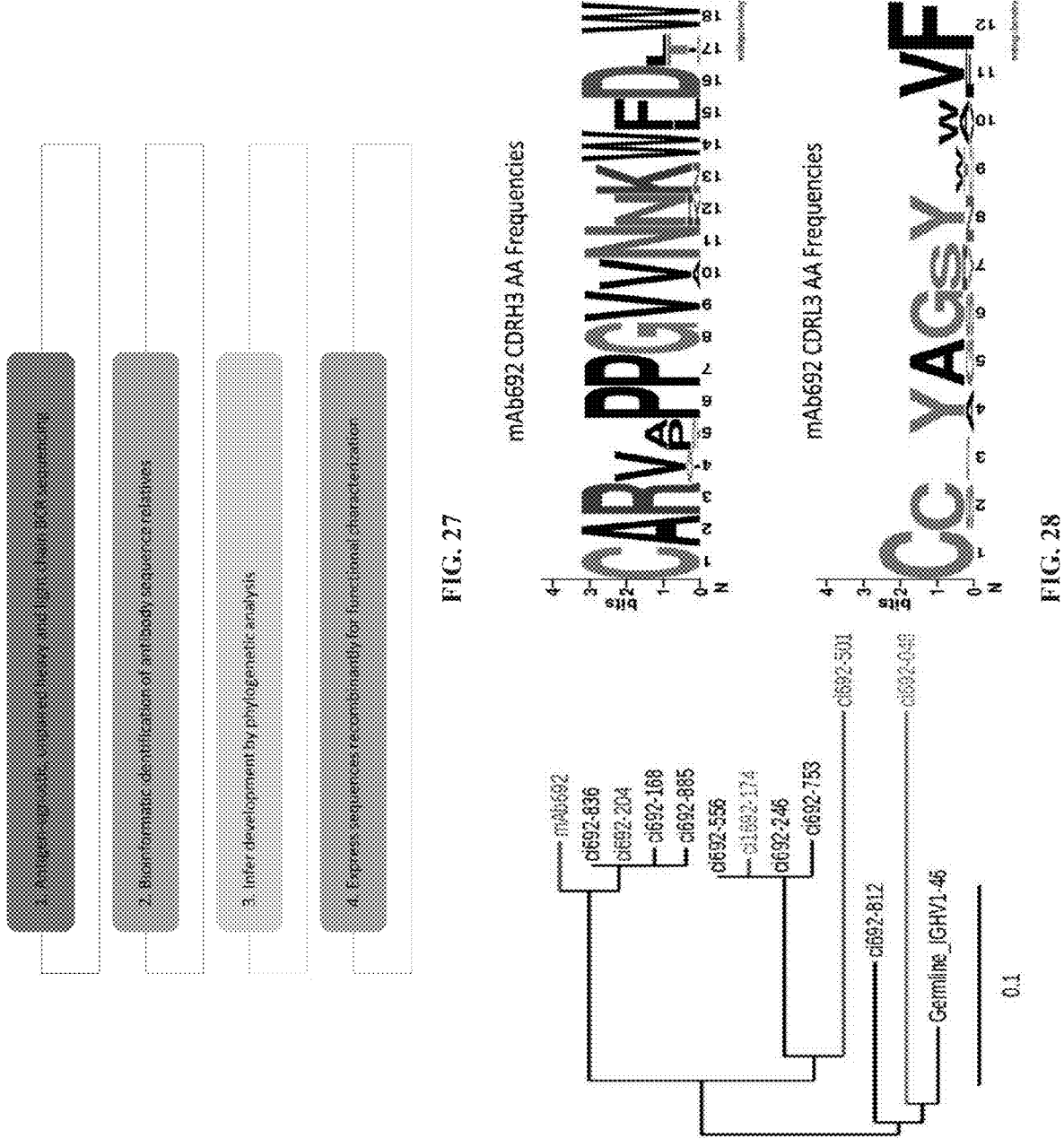
FIG. 27 shows the experimental workflow for identifying HIV/HCV mAb relative sequences.
FIG. 28 shows mAb692 development and sequence.
Figures 29A, 29B:
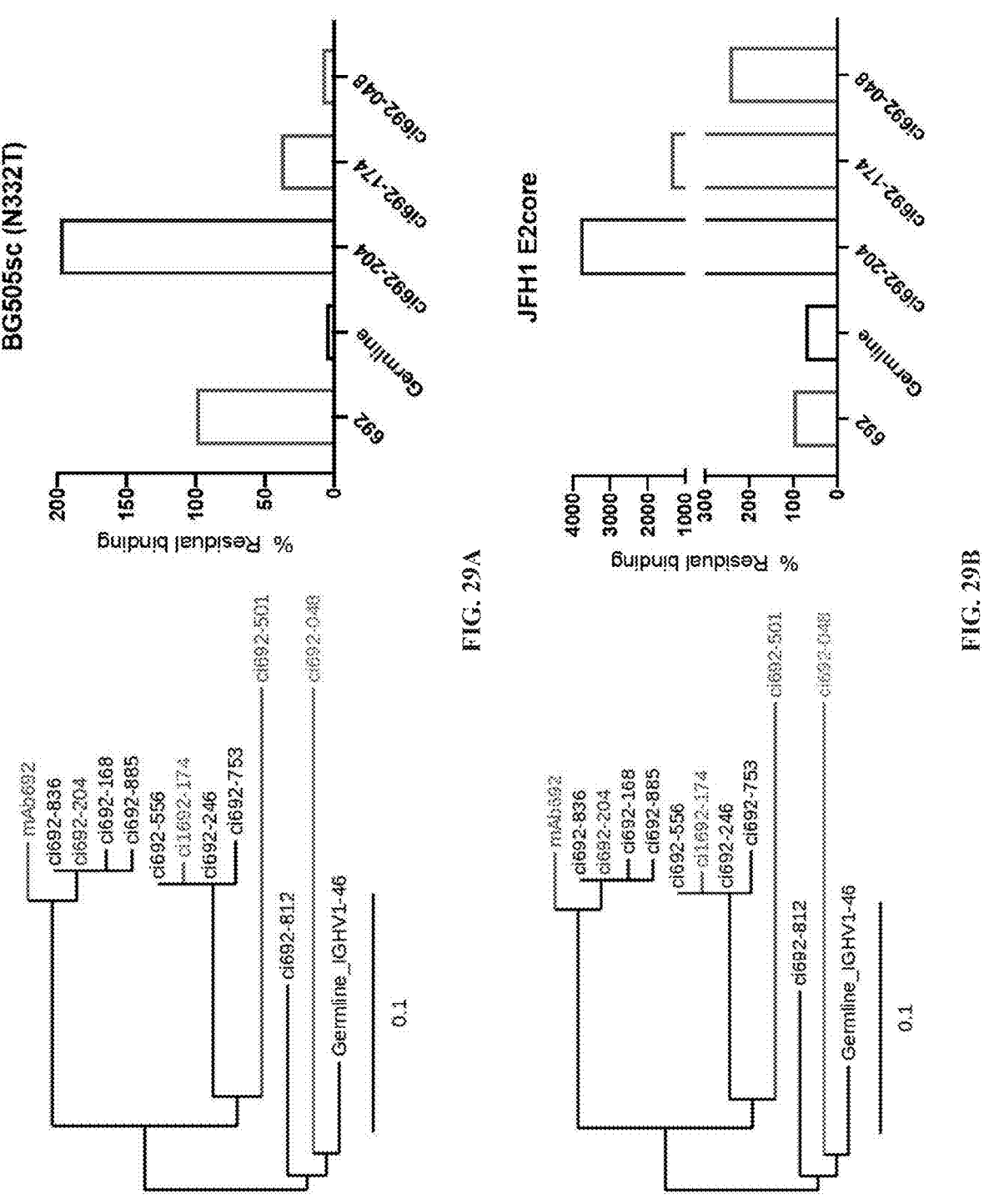
FIGS. 29A-29B shows that acquired mutations alter antigen specificity.
Figure 30:
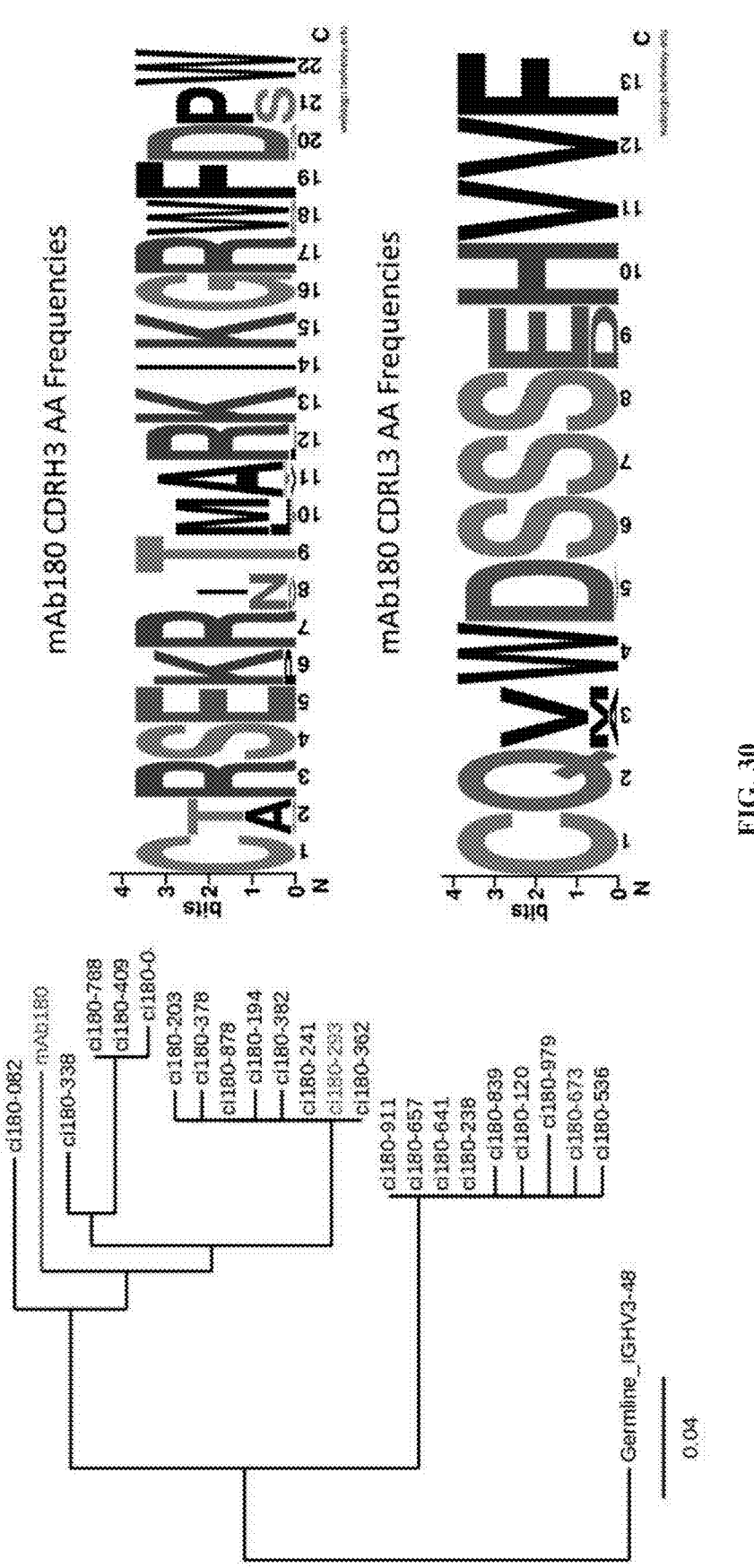
FIG. 30 shows mAb180 development and sequence.
Figure 31A:
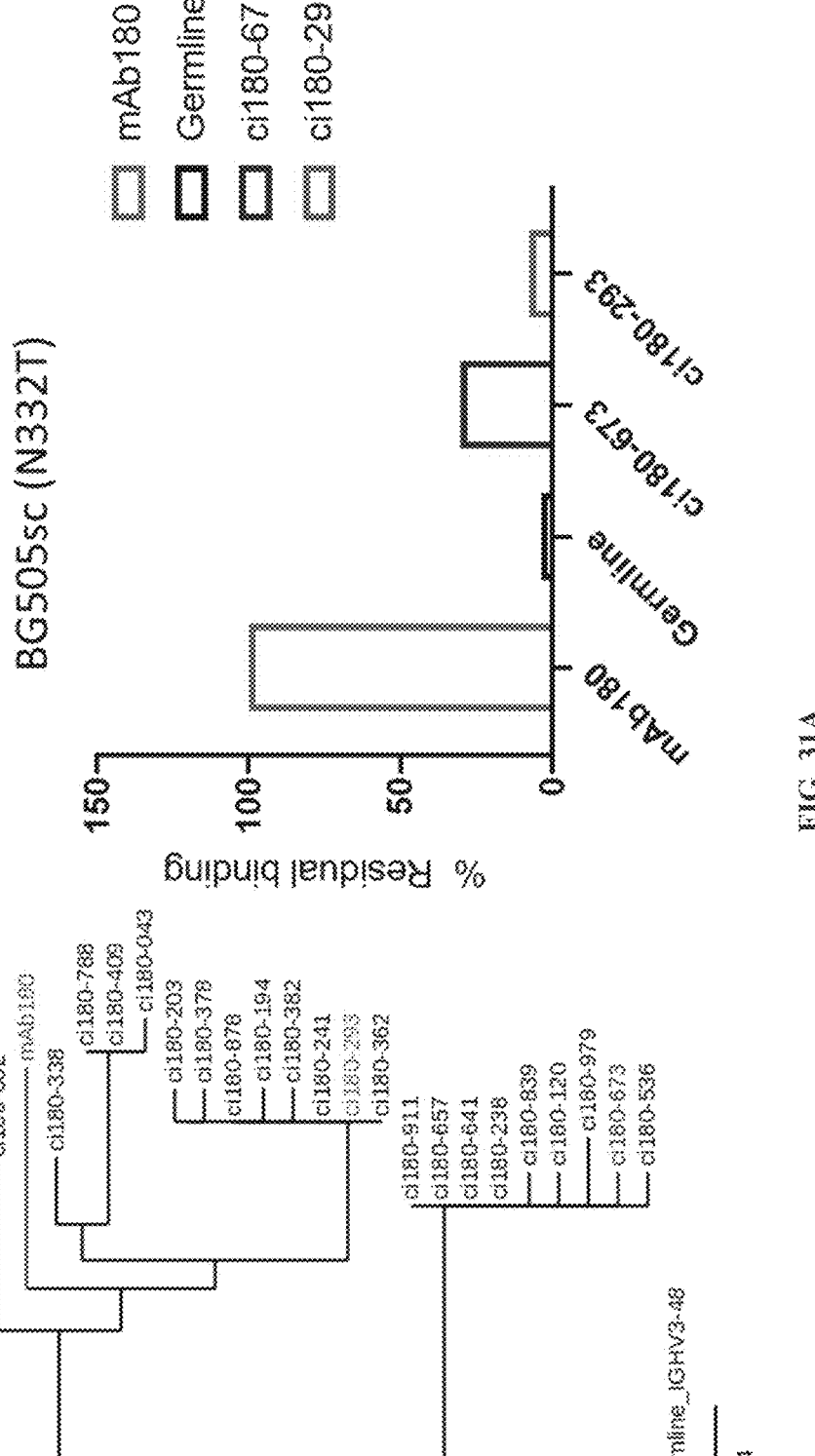
Figure 32:
FIG. 32 shows epidemiology of HIV and HCV mono- and co-infection and significance of the current study.
Figure 32:
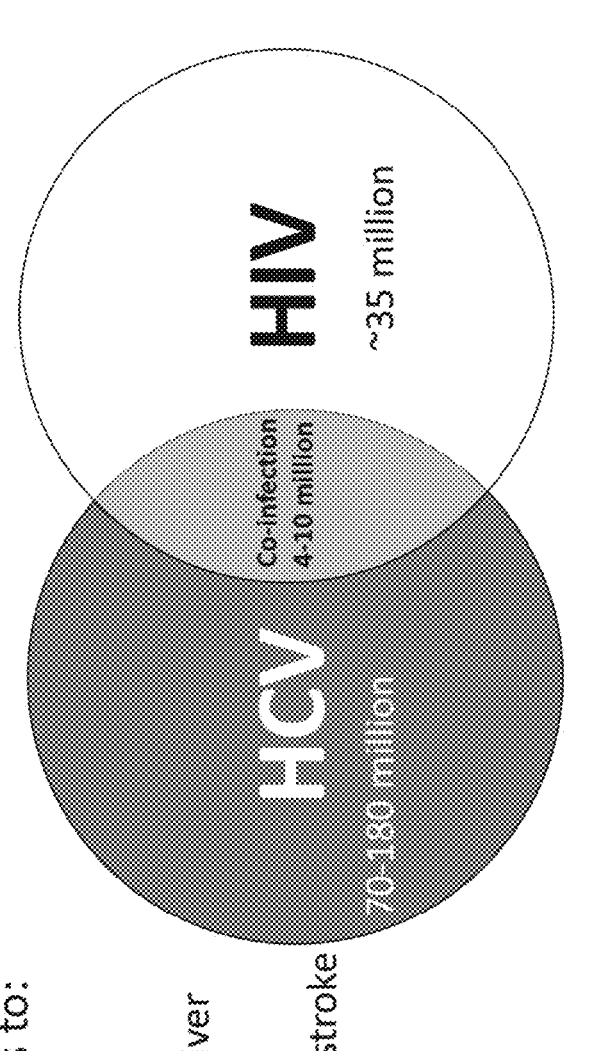
Figure 33A:
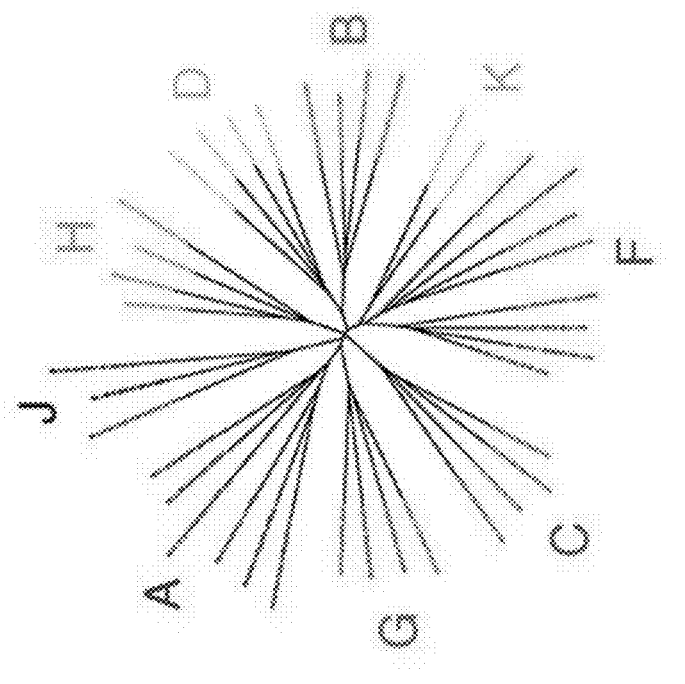
FIGS. 33A-33B show the diversity of HCV (FIG. 33A) and HIV (FIG. 33B) proteins, which renders the difficulties of vaccine development to treat these viruses.
Figure 33B:
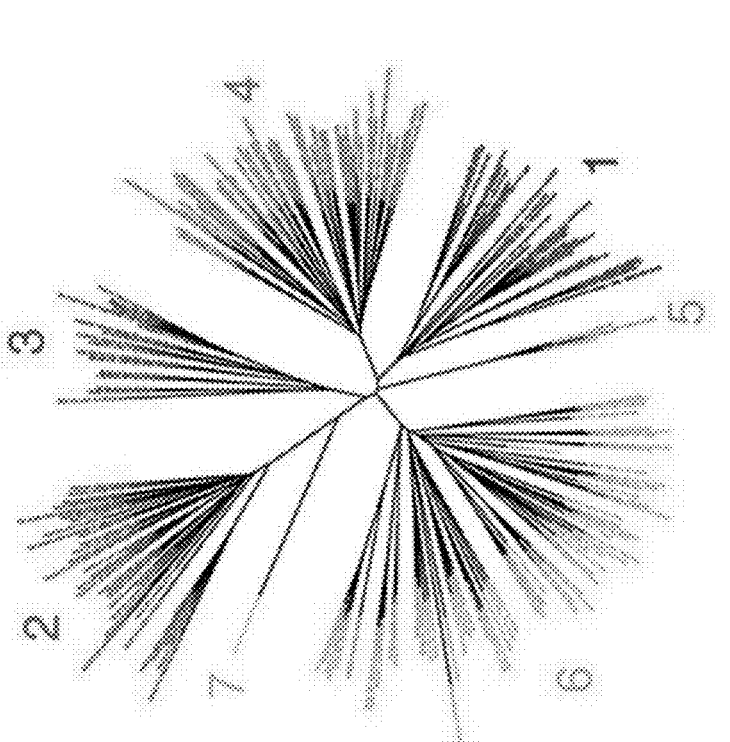
Figure 34:
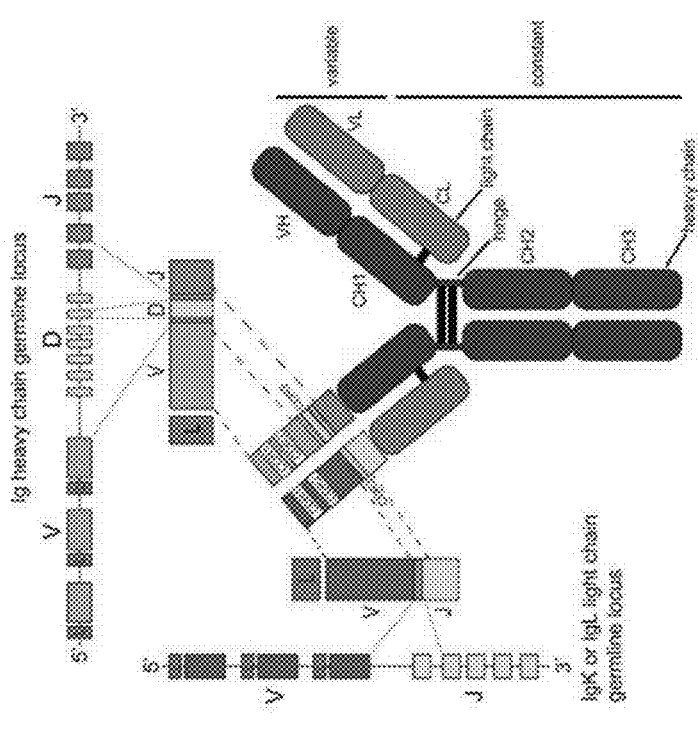
FIG. 34 depicts schematic representation of antibody structures.
Figure 35:
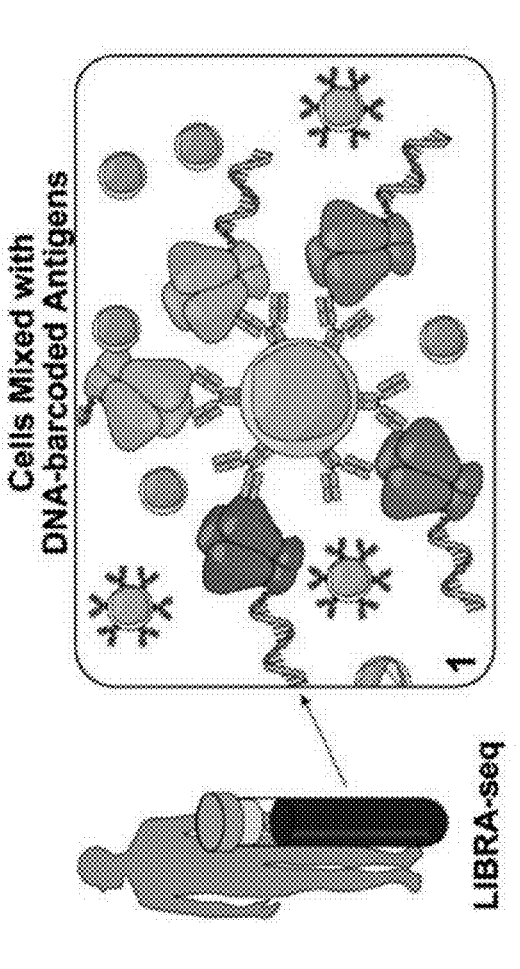
FIG. 35 shows LIBRA-seq: high throughput mapping of b cell receptor specificities.
Figure 35:
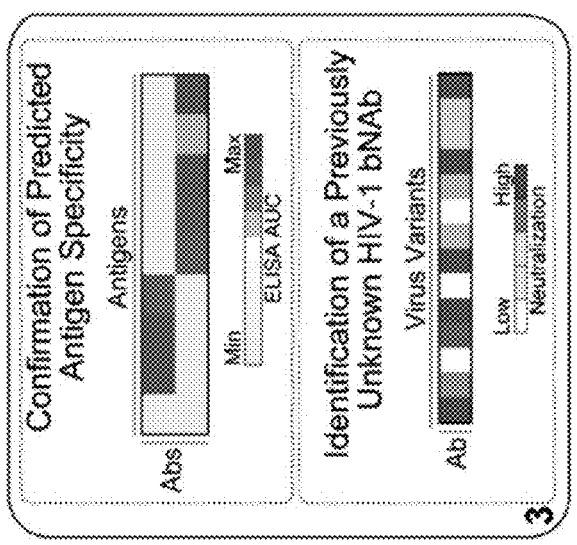
Figure 35:
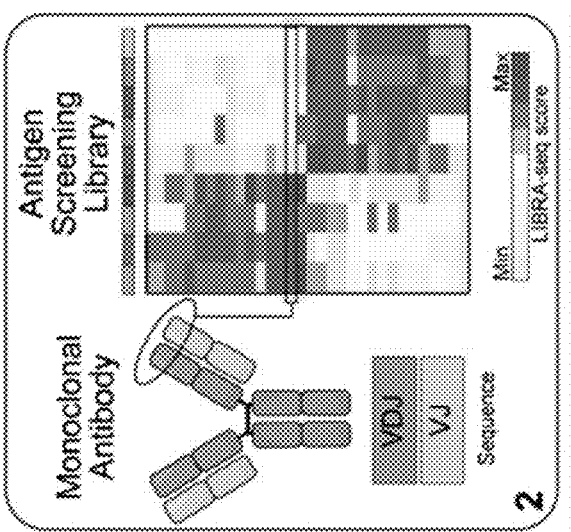
Figure 36A:
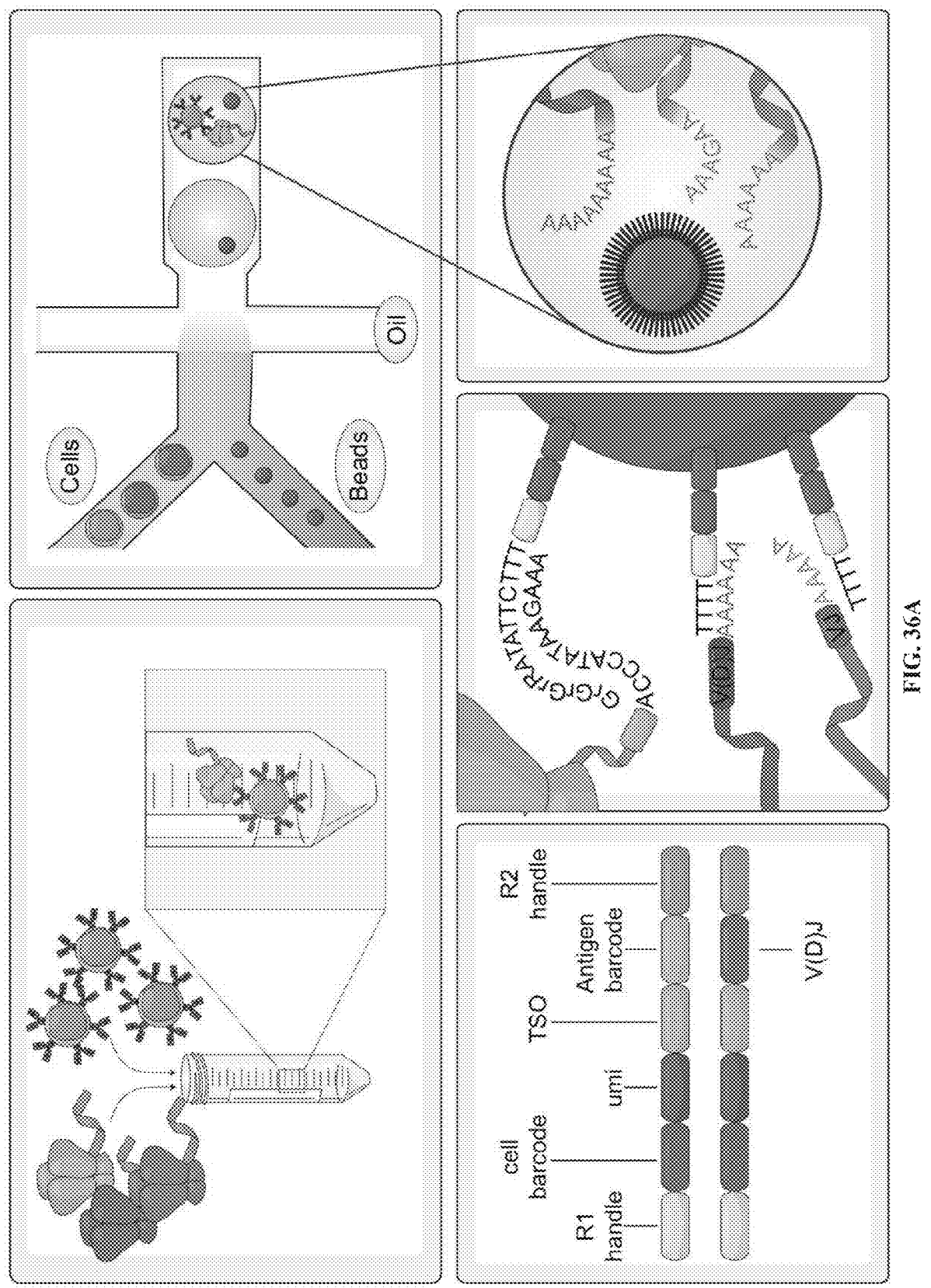
FIGS. 36A-36B shows Linking B cell Receptor sequence to Antigen Specificity by Sequencing (LIBRA-Seq).
Figure 36B:
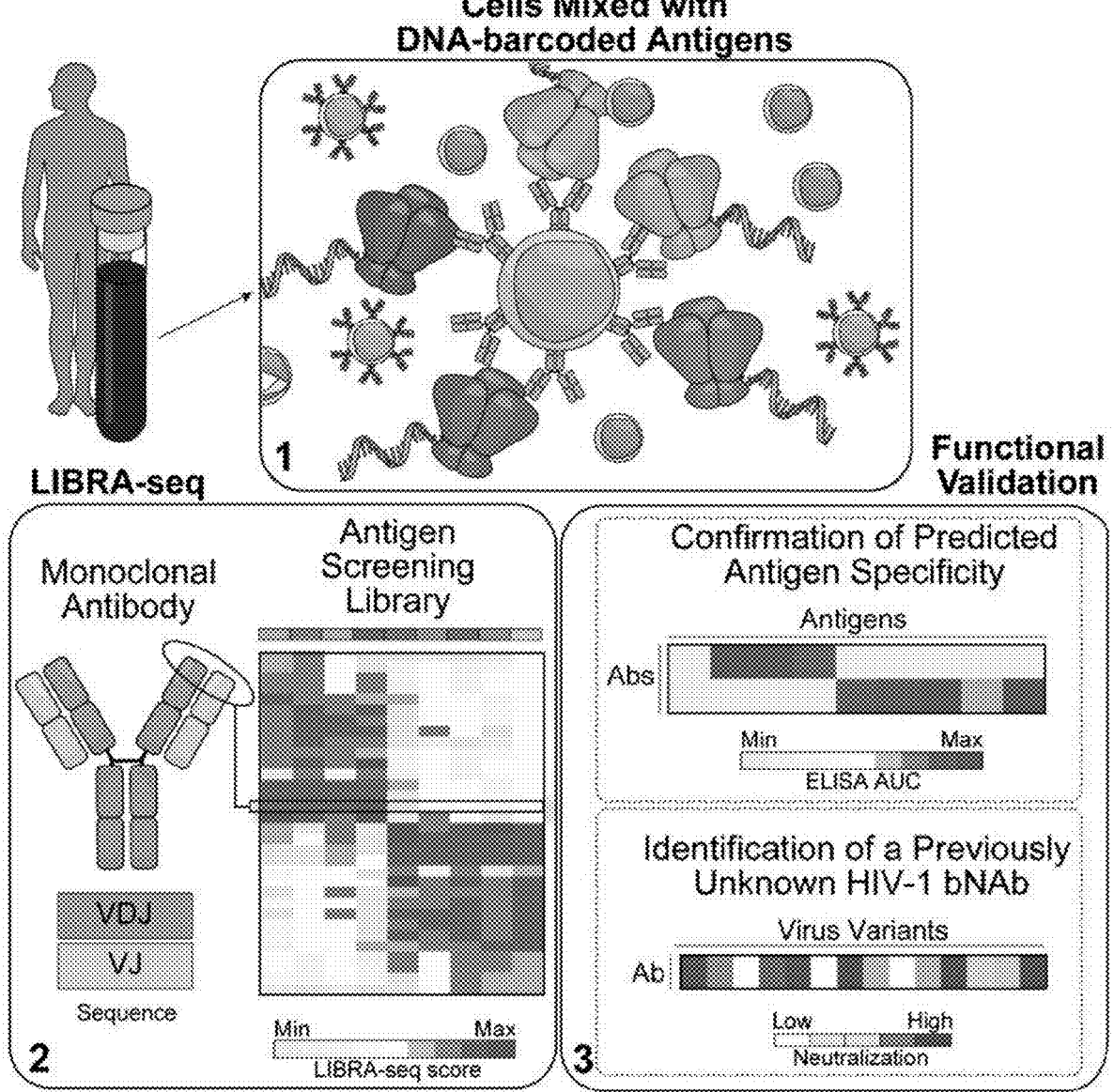
Figure 37:
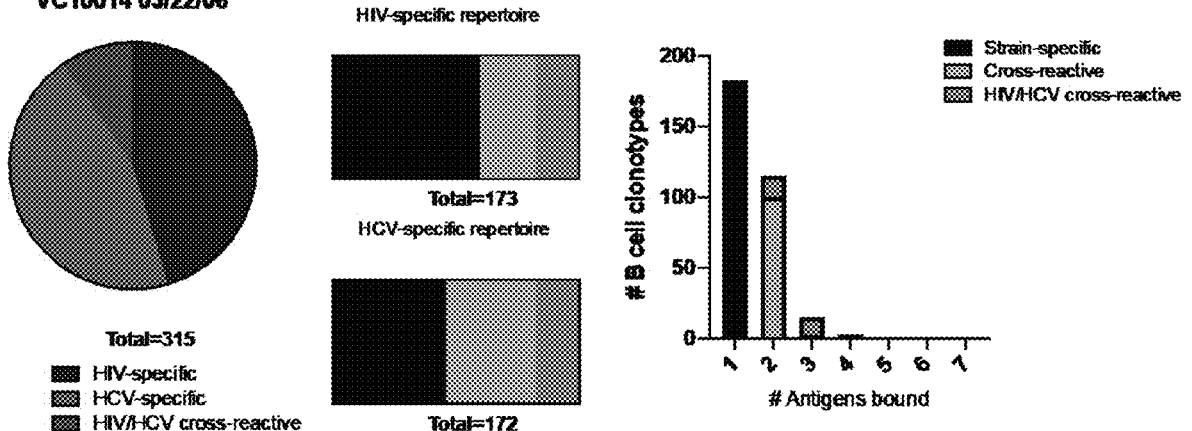
FIG. 37 shows that LIBRA-seq identifies virus-specific antibody specificities.
Figure 38:
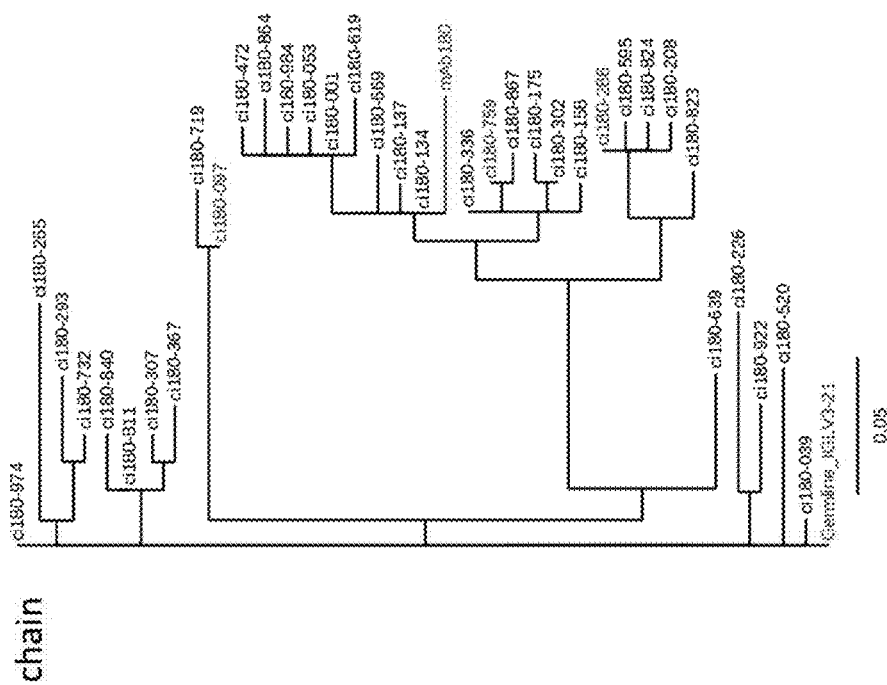
FIG. 38 shows mAb180 antibody development revealed by unpaired BCR sequencing.
Figure 38:
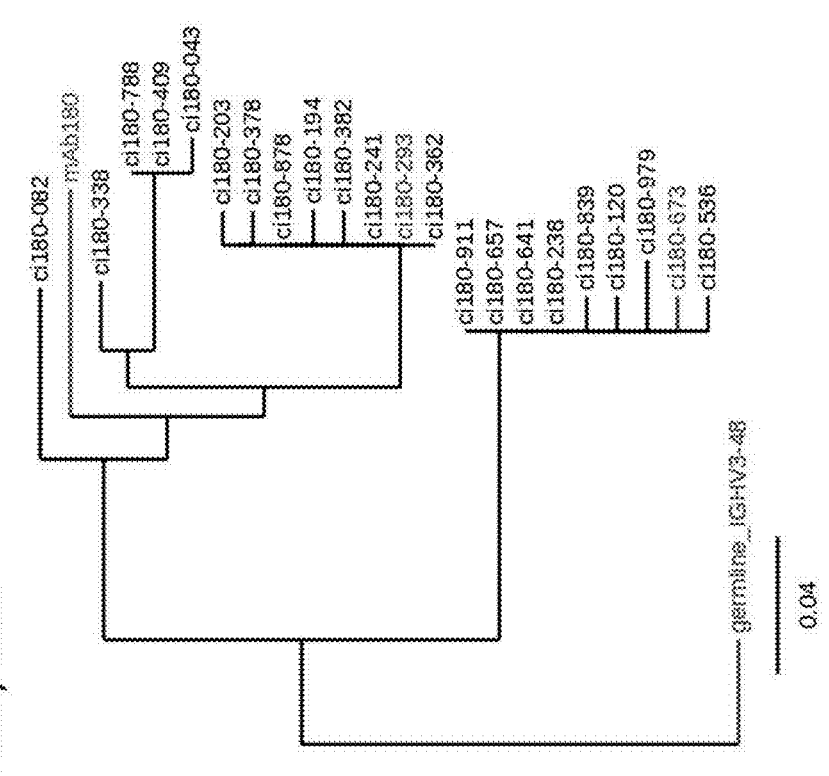
Figure 39:
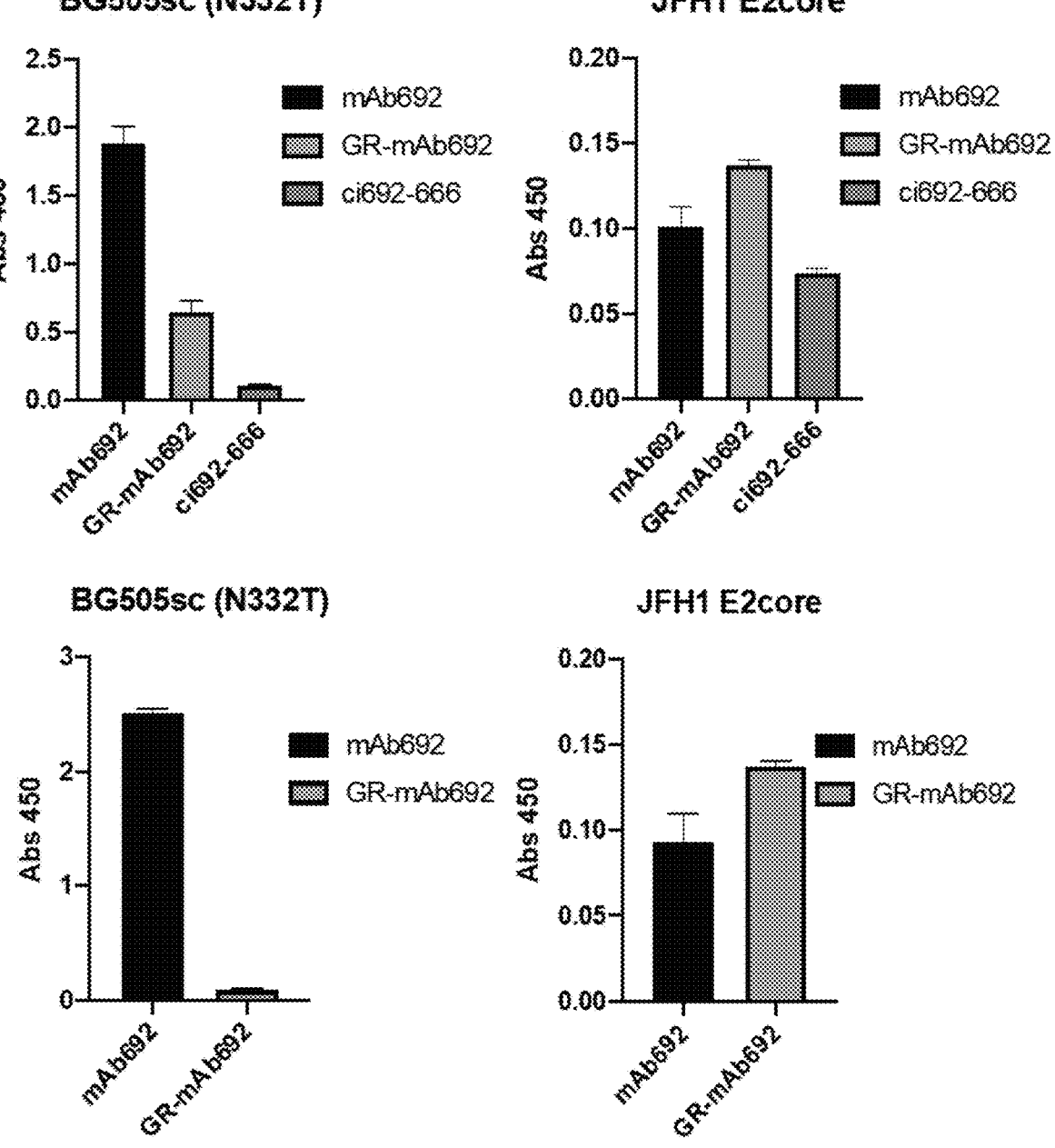
FIG. 39 depicts germline reverted mAb sequences showing inverted antigen specificities.
Figure 40:
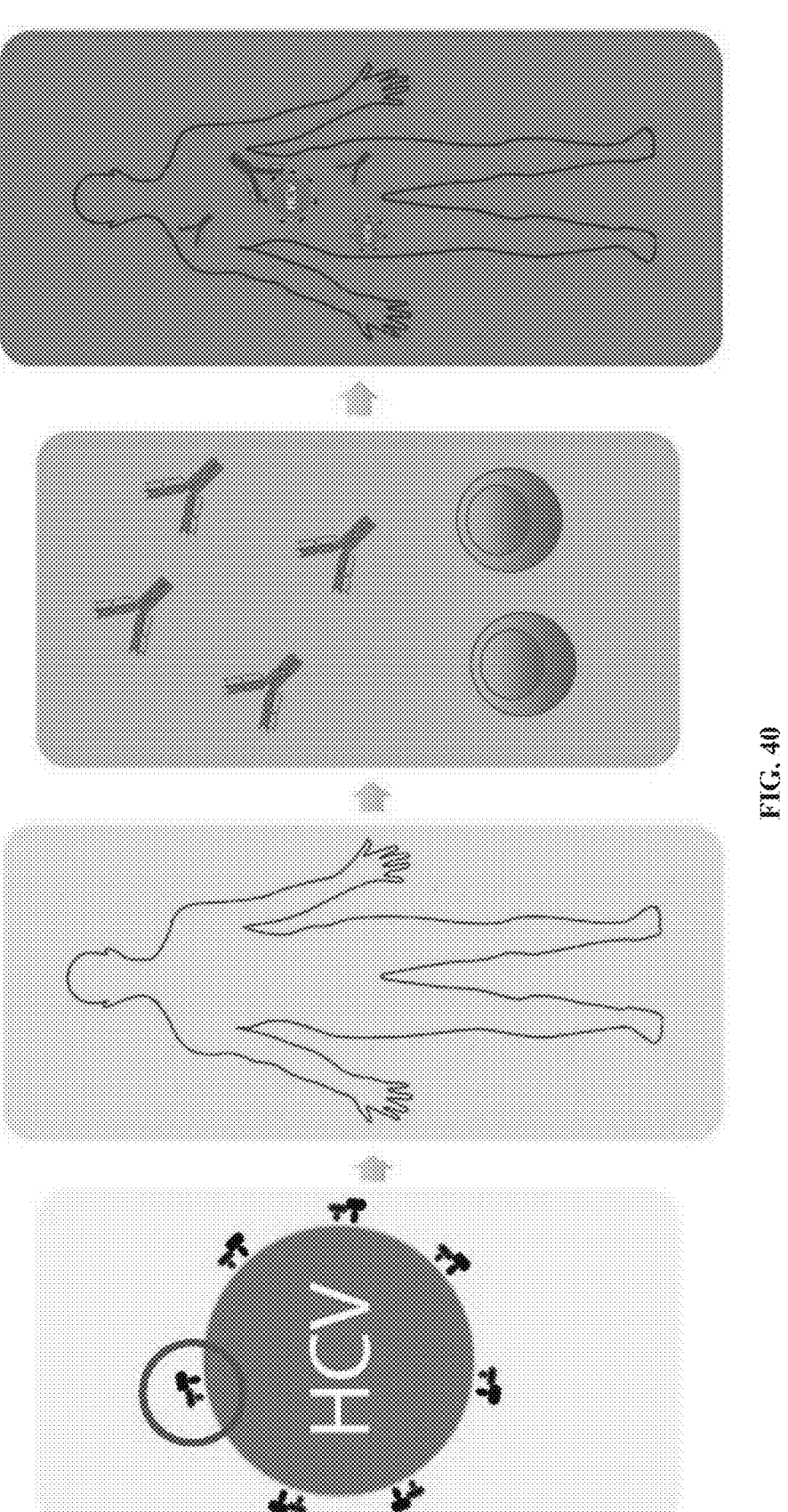
FIG. 40 shows immune responses during HCV infection. HCV the sole target of the neutralizing antibody response is the E1E2 glycoprotein heterodimer. The virus infects a person, and the person makes antibodies against the virus. These antibodies can then bind the virus and may lead to an initial suppression of viremia, but ultimately in 60-80% of the cases the immune system fails to clear the virus and it turns into chronic infection.
Figure 41:
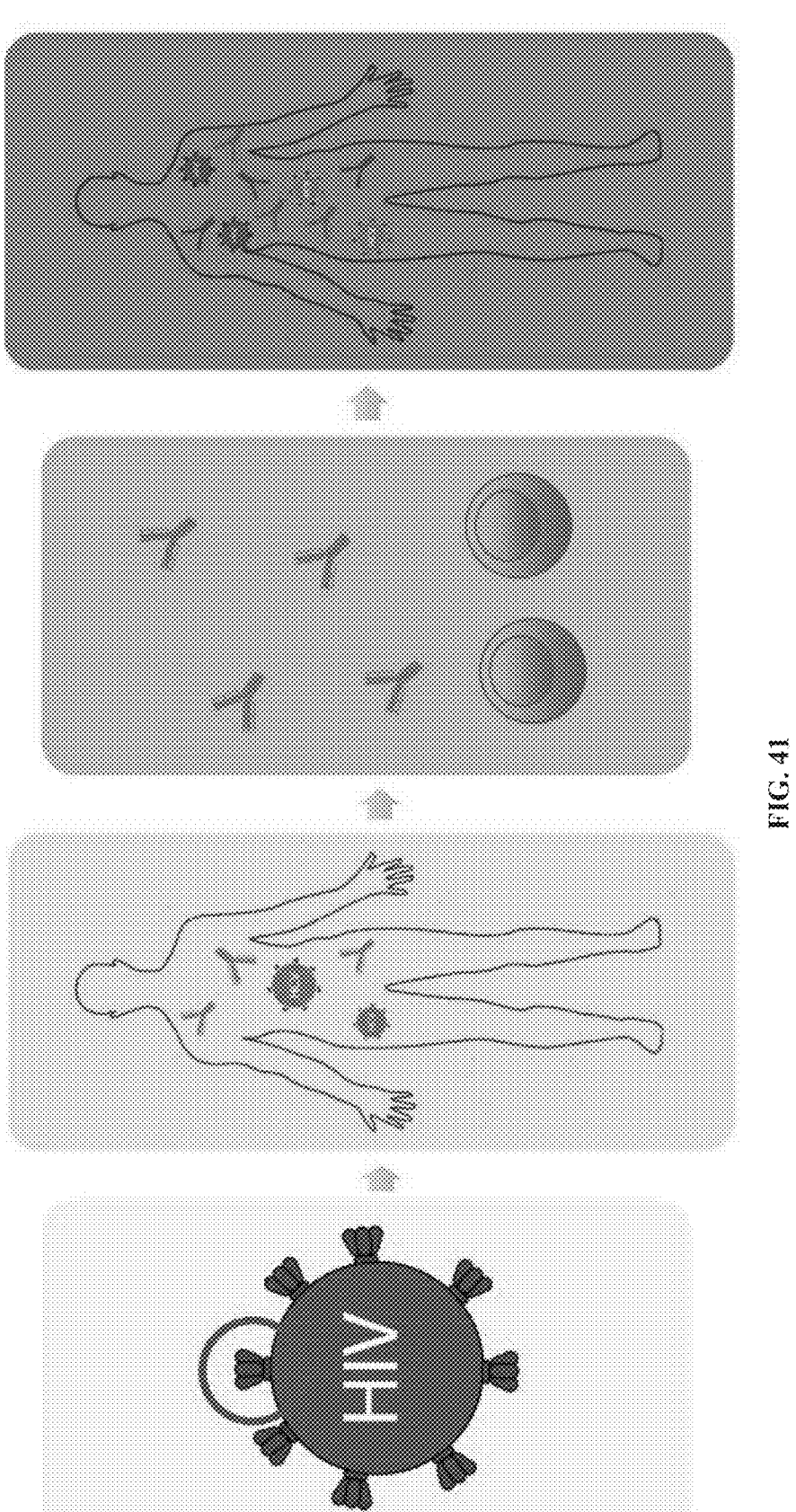
FIG. 41 shows immune responses during HCV/HIV co-infection. Target of the neutralizing antibody response during HIV infection is the envelope glycoprotein, Env.
Figures 42, 43:
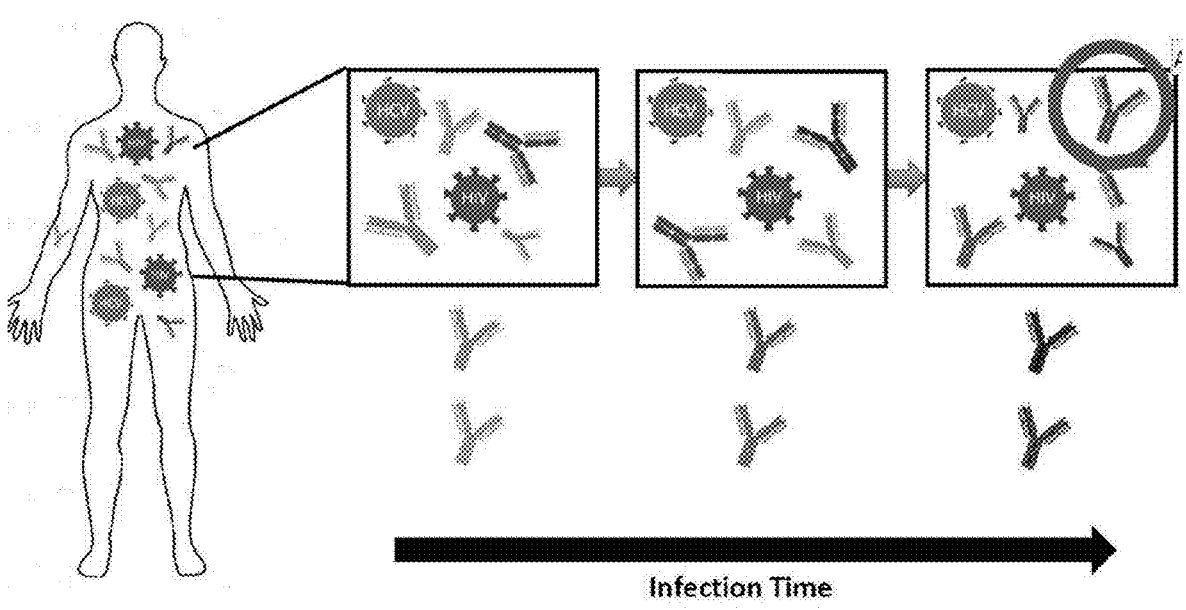
FIG. 42 shows antibody responses during chronic HIV/HCV co-infection. Over the course of chronic infection, the antibody response continues to develop, acquiring mutations and expanding. In this schematic, the darkening colors of the antibodies are meant to represent this development over time. The red antibodies recognizing HIV and the blue antibodies recognizing HCV. The "purple" antibodies (circled) are those can recognize both viruses.
FIG. 43 shows the information of the Vanderbilt HIV Cohort.
Figures 44, 45:
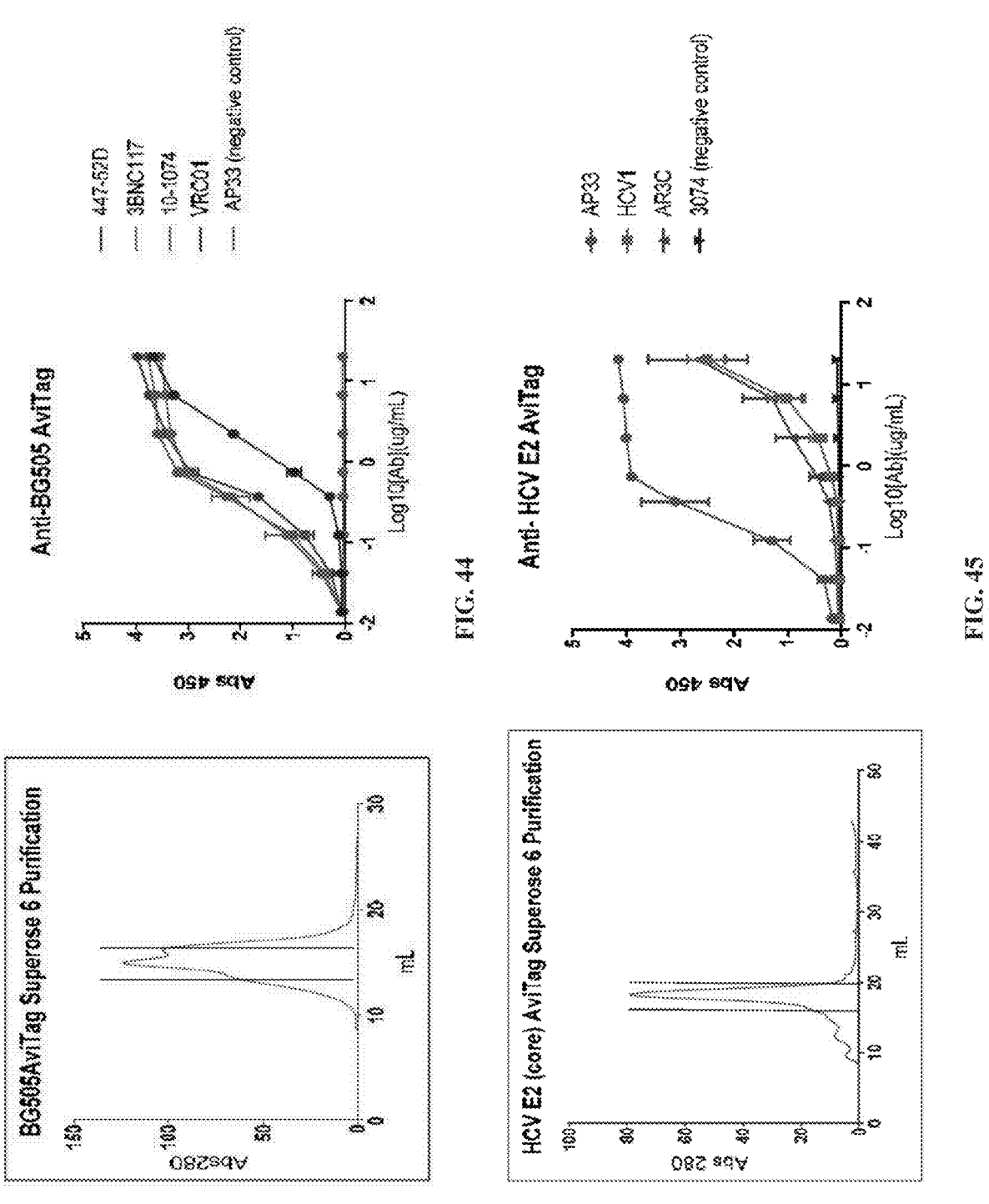
FIG. 44 shows the purification of HIV Env: BG505 SOSIP.664 AVITAG™. VRC01 binds cd4bs (Wu et al Science 2009); 10-1074 binds glycan patch; 3BNC117 binds CD4bs; PGT145 binds v1v2 quaternary trimer specific epitope 447-52D V3 directed antibody.
FIG. 45 shows the purification of HCV Env: E2 (core) AVITAG™
Figure 46:
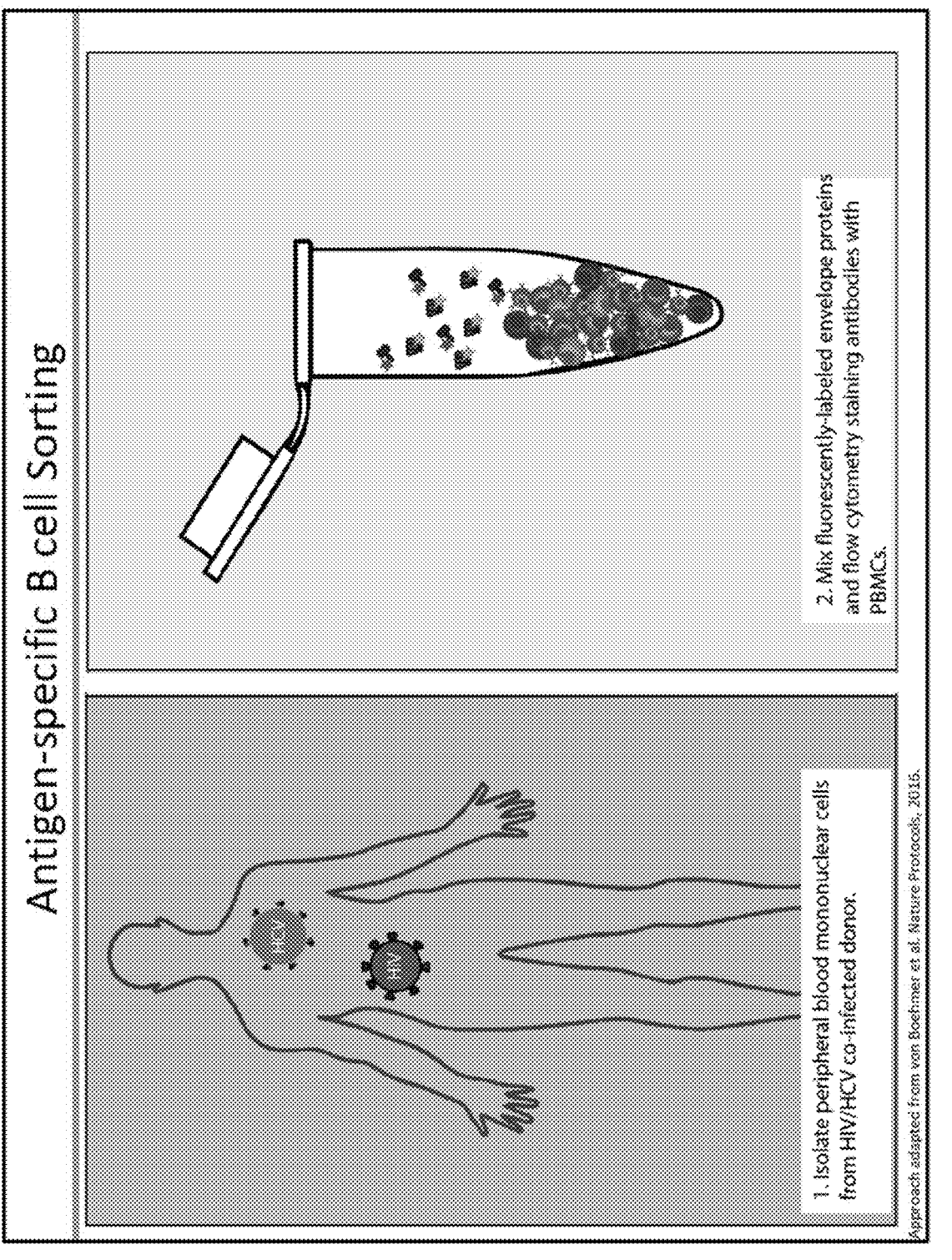
FIG. 46 shows antigen-specific B cell sorting. Peripheral blood mononuclear cells (PBMC) were isolated from HIV/HCV co-infected donors. Then the PBMCs were mixed with fluorescently-labeled proteins and flow cytometry staining antibodies.
Figure 47:
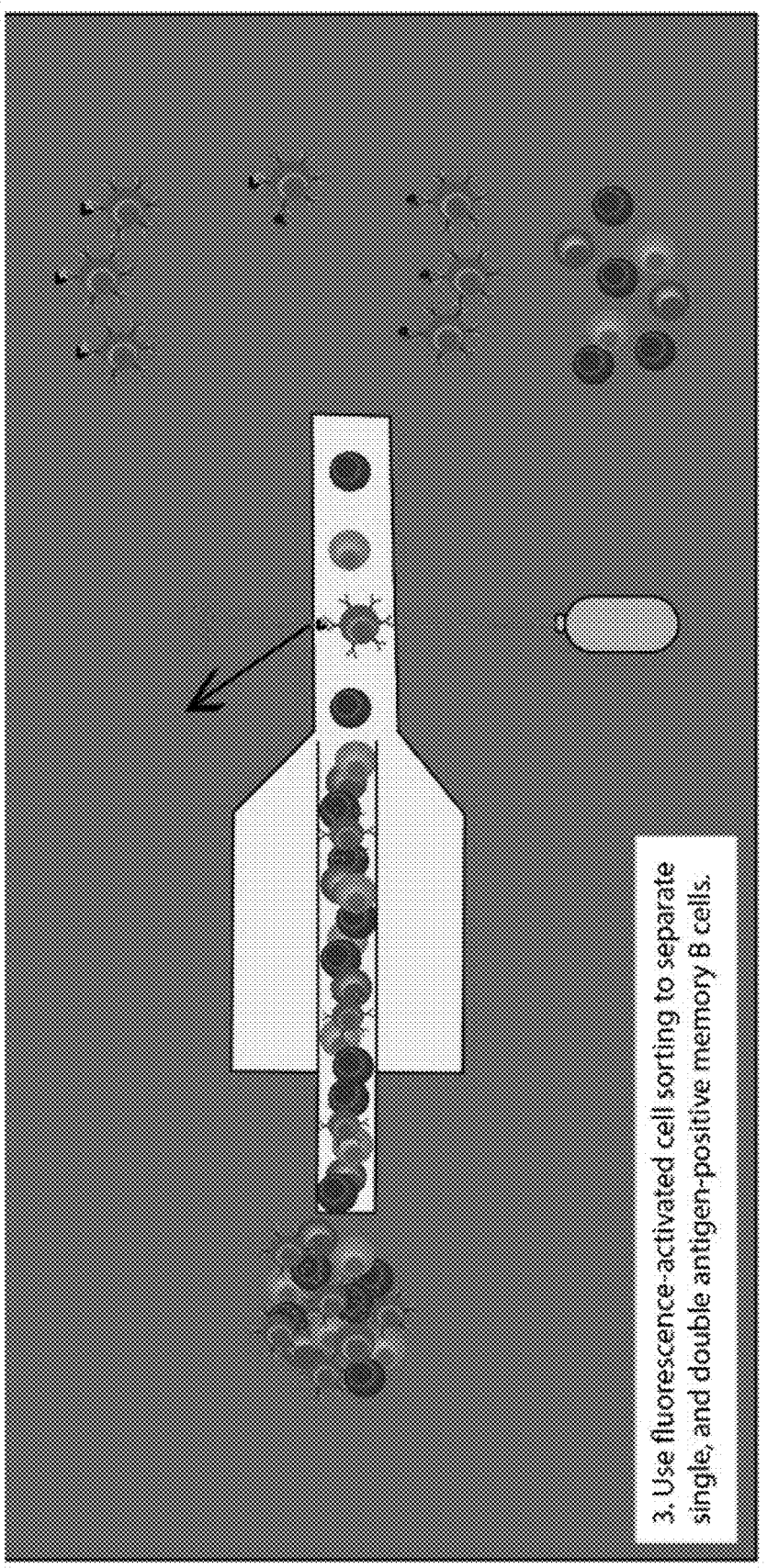
FIG. 47 shows antigen-specific B cell sorting.
Figure 48:
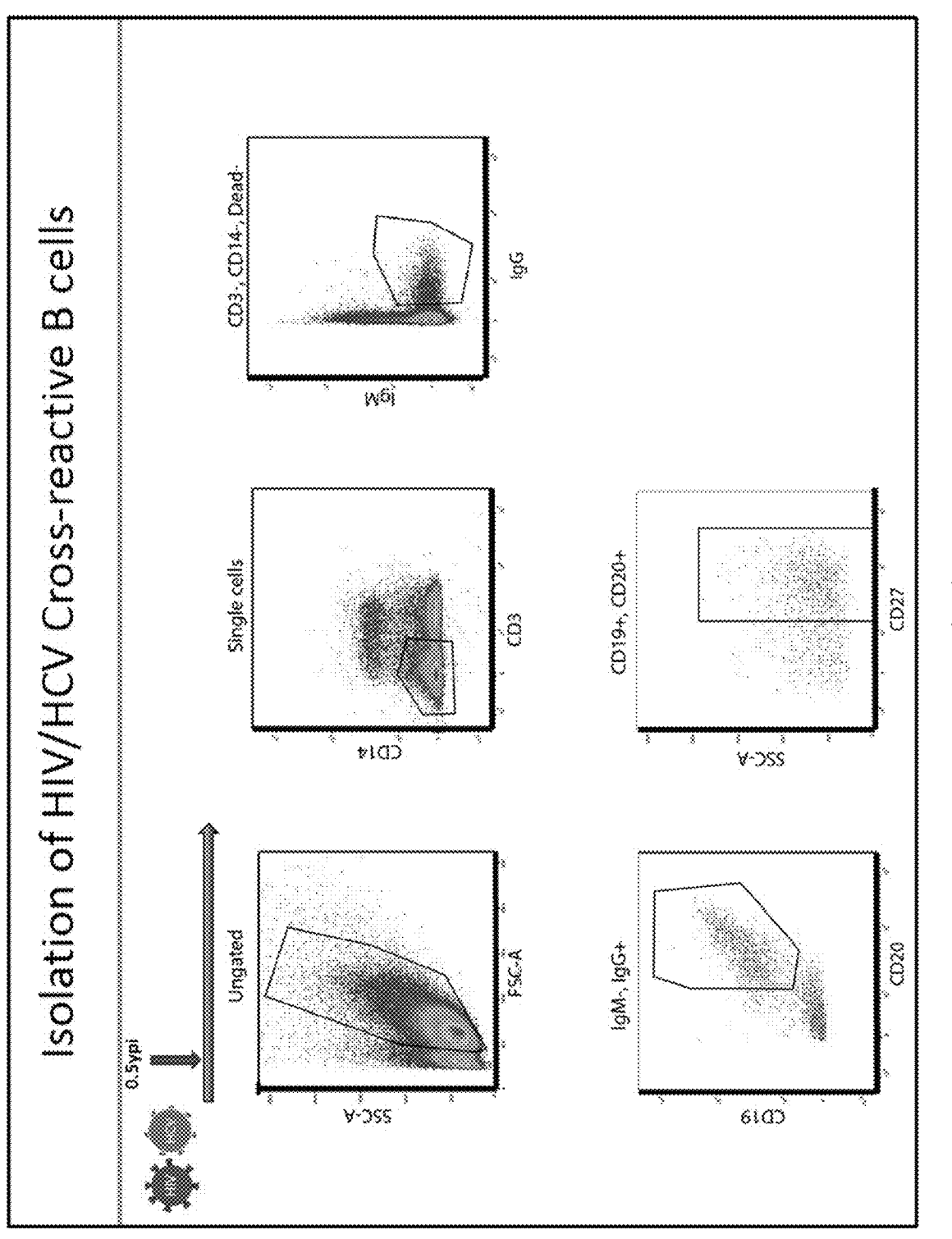
FIG. 48 shows isolation of HIV/HCV cross-reactive B cells.
Figure 48:
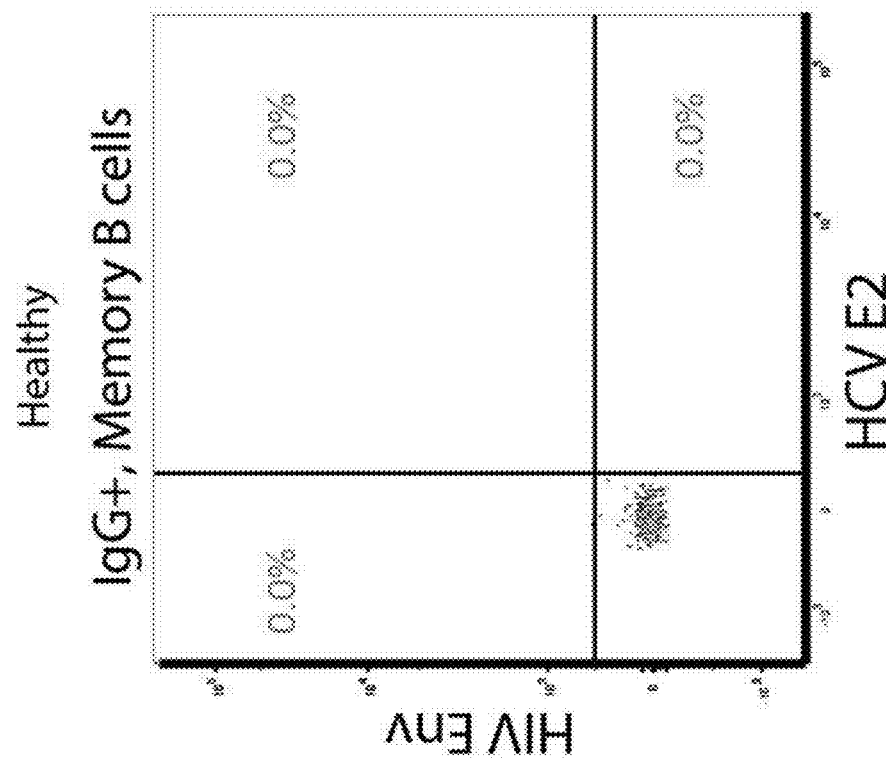
Figure 48:
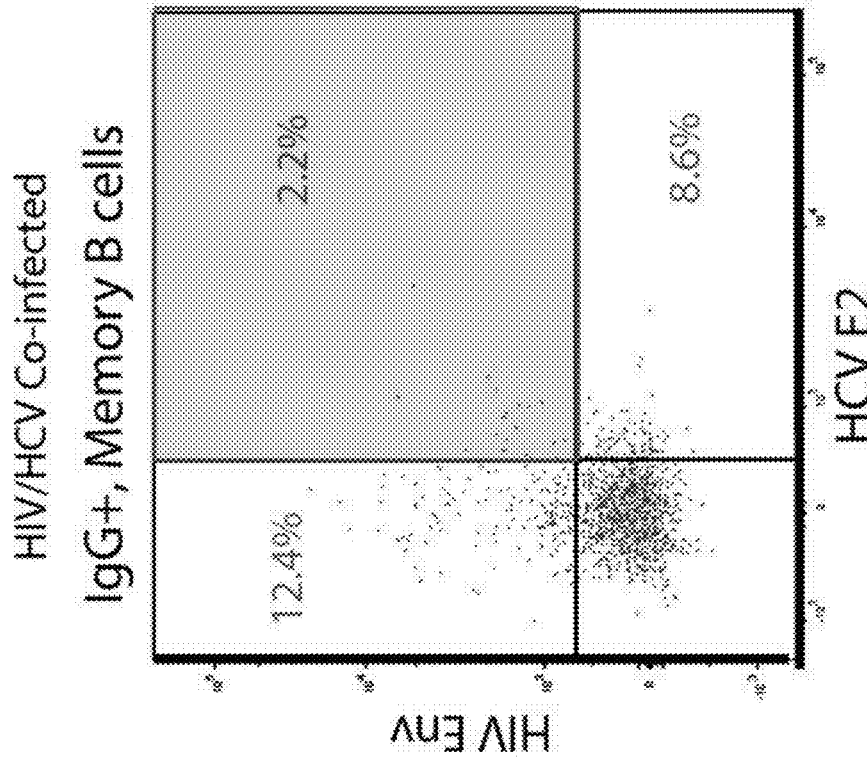
Figures 49A, 49B:
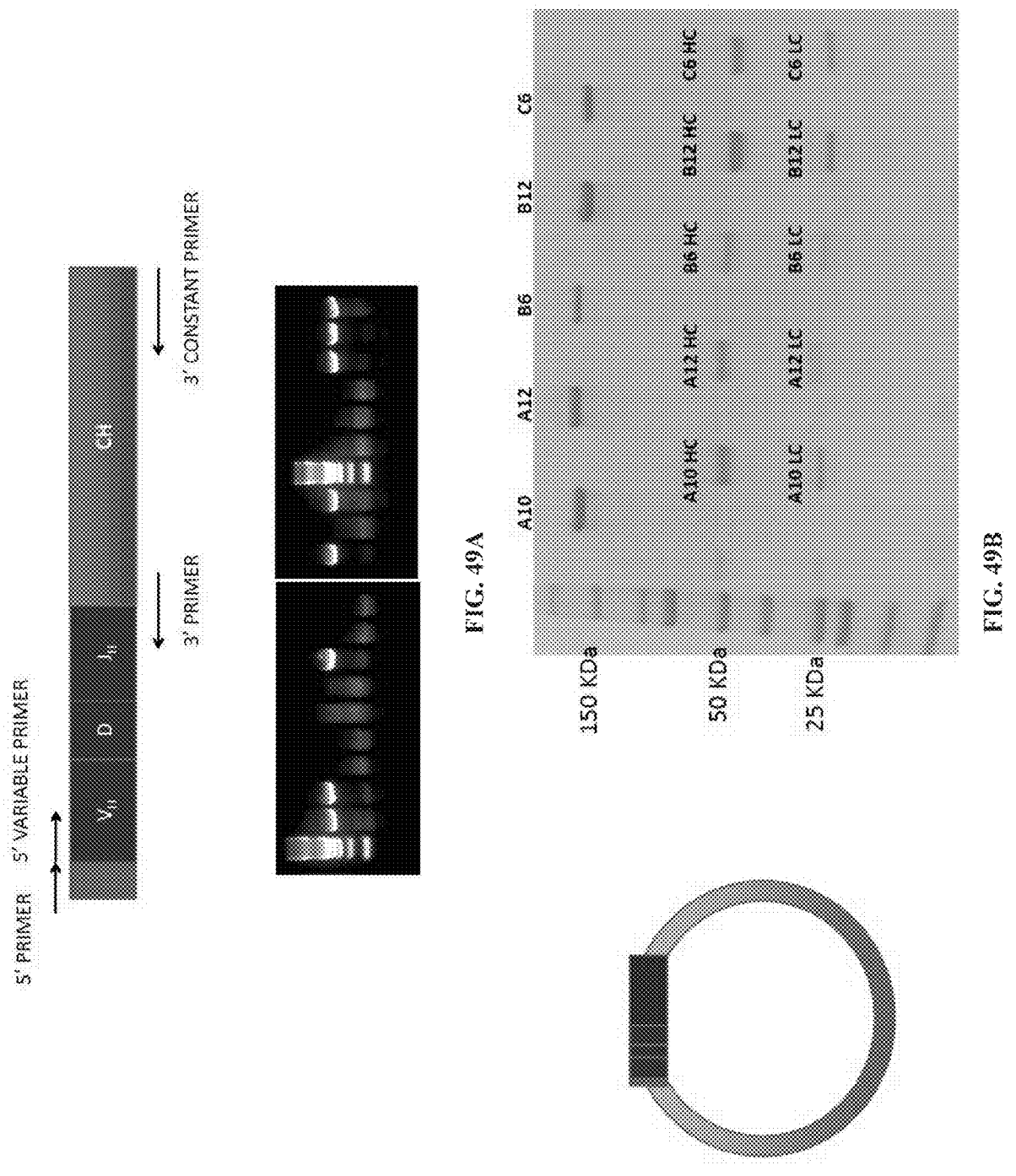
FIGS. 49A-49B show single B cell receptor PCR and protein expression.
Figure 50:
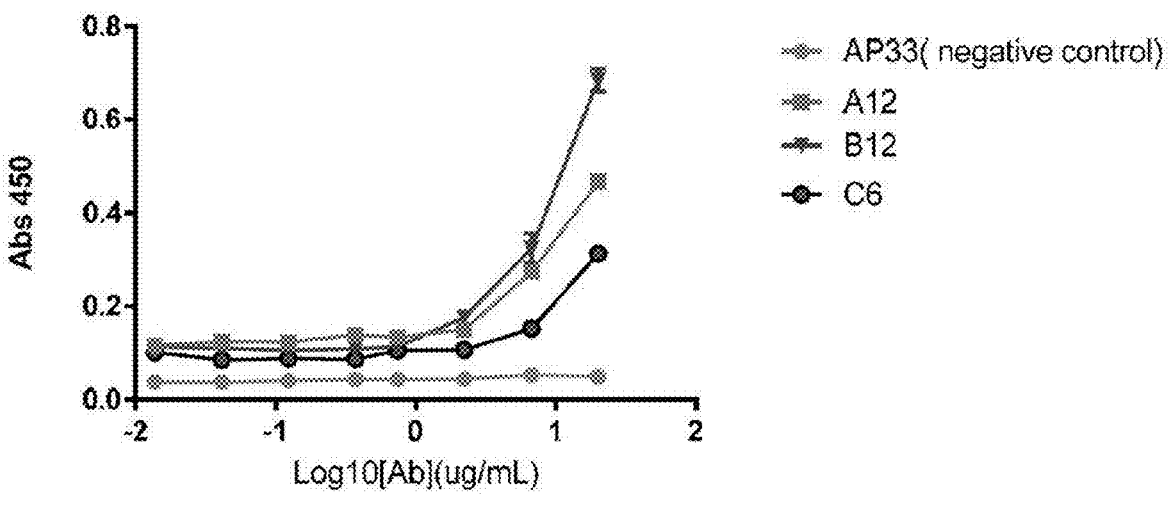
FIG. 50 shows HIV/HCV cross-reactive antibodies binding BG505 AVITAG™.
Figure 51:
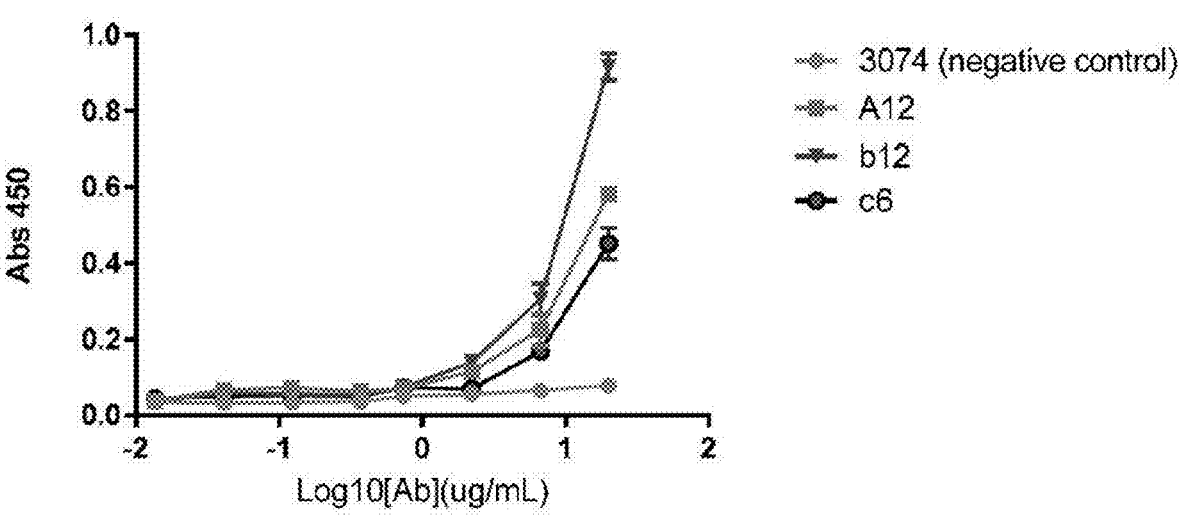
FIG. 51 shows HIV/HCV cross-reactive antibodies binding E2 (core) AVITAG™.
Figures 52, 53:
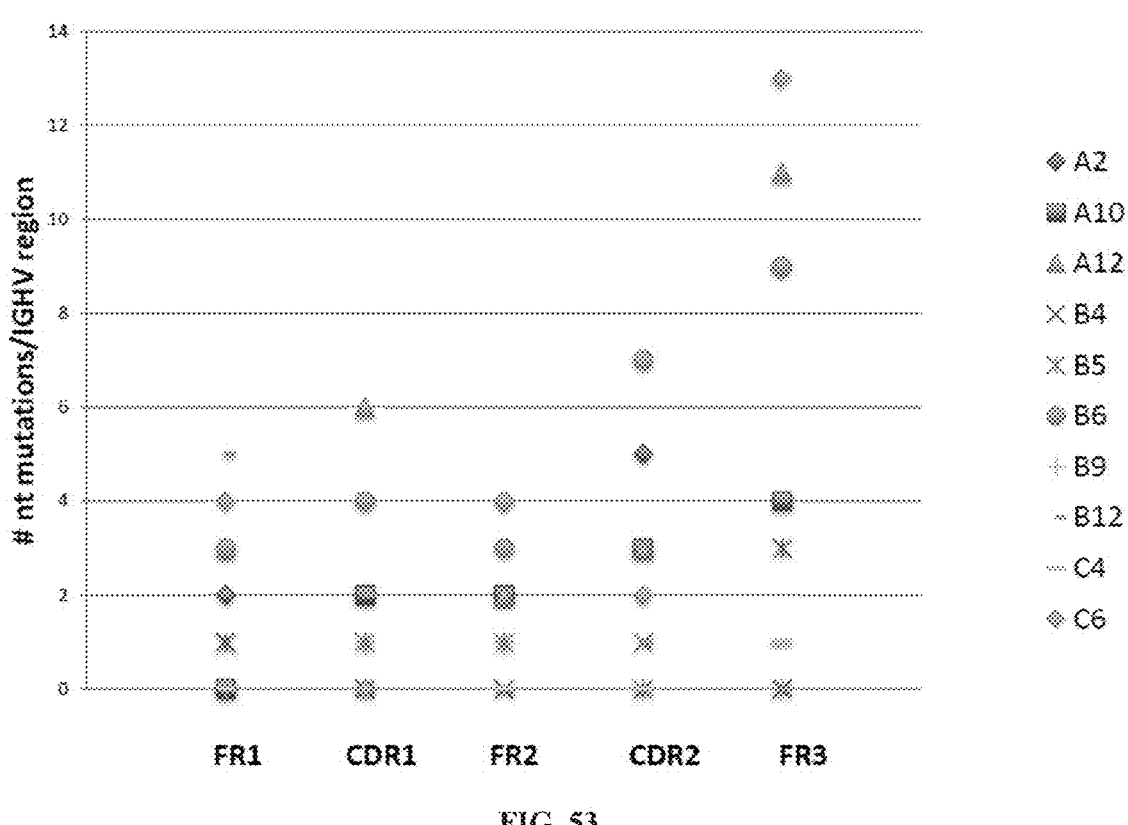
FIG. 52 shows isolated HIV/HCV cross-reactive antibodies derive from different germline genes. Sequences in FIG. 52: CAREQRDYXSGFDYW (SEQ ID NO: 13138); CARLRRDGSYHHGAPFYFDNW (SEQ ID NO: 13139); CARGGYQDSAGYADYW (SEQ ID NO: 13140); CARG-GRDLVRGLVMTDFFDEW (SEQ ID NO: 13141); CARLRWSSSWYYRFDYW (SEQ ID NO: 13142); CTTAFSMKYCSSTNCPRSDWYFDLW (SEQ ID NO: 13143).
FIG. 53 shows cross-reactive antibody sequences, HIV/HCV cross-reactive antibody VH mutations.
Figure 54:
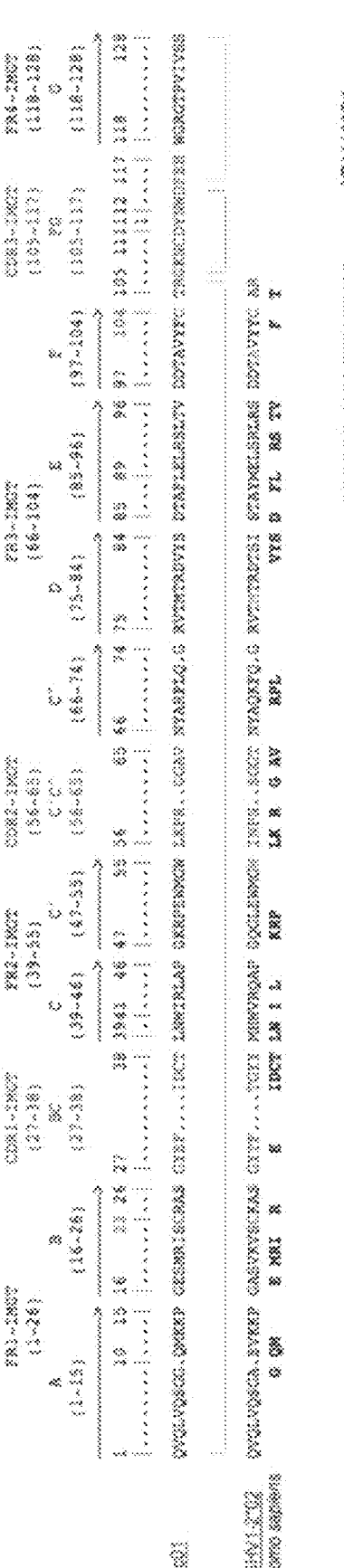
FIG. 54 shows B12 antibody sequence aligned to the reference IMGT database to identify which gene alleles are used. Sequences in FIG. 54.

In some embodiments, the CDRH3 sequence comprise a sequence shown in FIG. 28. In some embodiments, the CDRH3 sequence comprise a sequence shown in FIG. 30. In some embodiments, the CDRL3 sequence comprise a sequence shown in FIG. 28. In some embodiments, the CDRL3 sequence comprise a sequence shown in FIG. 30.

Methods

Disclosed herein are methods for preventing, treating, inhibiting, or reducing HIV and/or HCV infection.

In some aspects, disclosed herein is a method of producing a recombinant antibody comprising cultivating or maintaining the host cell of any preceding aspect under conditions to produce a recombinant antibody as described herein.

In some aspects, disclosed herein is a method of treating, preventing, reducing, and/or inhibiting HIV infection, HCV, infection, or HIV/HCV co-infection, comprising administering to a subject a therapeutically effective amount of a recombinant antibody, wherein the recombinant antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein CDRL3 comprises an amino acid sequence at least 60% identical to

```
                                    (SEQ ID NO: 13)
MQPLQLPDT, (SEQ ID NO: 25)
QQSYNVPT, (SEQ ID NO: 39)
HQSSSLPFT, (SEQ ID NO: 49)
QHFYSSPPT, (SEQ ID NO: 88)
CLYAGSYSWV,
or (SEQ ID NO: 101)
QVWDSSSEHVV;
``` and/or
CDRH3 comprises an amino acid sequence at least 60% identical to

```
                                    (SEQ ID NO: 104)
ARVAPPGVVNNKWFDI, (SEQ ID NO: 110)
ARSEKRVTMTRKIKGRWFGP, (SEQ ID NO: 1817)
CAAGLWSGDLSRPRYSDSW, (SEQ ID NO: 1818)
CAKGLTTESRLEFW, (SEQ ID NO: 1819)
CVSSWGPESPYYFDYW,
or (SEQ ID NO: 1820)
CAREYCTGGDCHFFLDYW.
```

In some aspects, disclosed herein is a method of treating, preventing, reducing, and/or inhibiting HIV infection, HCV, infection, or HIV/HCV co-infection, comprising administering to a subject a therapeutically effective amount of a recombinant antibody, wherein the recombinant antibody comprises a light chain variable region (VL) that comprises a light chain complementarity determining region (CDRL) 1, CDRL2, and CDRL3 or a heavy chain variable region (VH) that comprises a heavy chain complementarity determining region (CDRH) 1, CDRH2, and CDRH3, wherein CDRL3 comprises an amino acid sequence at least 60% identical to

```
                                    (SEQ ID NO: 13)
MQPLQLPDT, (SEQ ID NO: 25)
QQSYNVPT, (SEQ ID NO: 39)
HQSSSLPFT, (SEQ ID NO: 49)
QHFYSSPPT, (SEQ ID NO: 88)
CLYAGSYSWV,
or (SEQ ID NO: 101)
QVWDSSSEHVV;
``` and/or
CDRH3 comprises an amino acid sequence at least 60% identical to

```
                                    (SEQ ID NO: 104)
ARVAPPGVVNNKWFDI, (SEQ ID NO: 110)
ARSEKRVTMTRKIKGRWFGP, (SEQ ID NO: 1817)
CAAGLWSGDLSRPRYSDSW, (SEQ ID NO: 1818)
CAKGLTTESRLEFW, (SEQ ID NO: 1819)
CVSSWGPESPYYFDYW,
or (SEQ ID NO: 1820)
CAREYCTGGDCHFFLDYW.
```

In some embodiments, the CDRL3 comprises at least one amino acid substitution when compared to SEQ ID NO: 13, 25, 39, 49, 88, or 101.

In some embodiments, the at least one amino acid substitution is selected from the group consisting of
a) at position 1 when compared to SEQ ID NO: 13, wherein the substituting amino acid residue is K;
b) at position 3 when compared to SEQ ID NO: 13, wherein the substituting amino acid residue is selected from the group consisting of A, T, G, V, D, Y, and F;
c) at position 6 when compared to SEQ ID NO: 13, wherein the substituting amino acid residue is selected from the group consisting of H, S, T, P, I, V, P, R, and V;
d) at position 9 when compared to SEQ ID NO: 13, wherein the substituting amino acid residue is selected from the group consisting of Y, L, H, P, I, G, C, J, R, and Q;

e) at position 5 when compared to SEQ ID NO: 25, wherein the substituting amino acid residue is selected from the group consisting of T, P, Y, R, I, G, and S;

f) at position 6 when compared to SEQ ID NO: 25, wherein the substituting amino acid residue is selected from the group consisting of A, T, and P;

g) at position 7 when compared to SEQ ID NO: 25, wherein the substituting amino acid residue is selected from the group consisting of W, A, R, G and L;

h) at position 3 when compared to SEQ ID NO: 39, wherein the substituting amino acid residue is T;

i) at position 4 when compared to SEQ ID NO: 39, wherein the substituting amino acid residue is selected from the group consisting of R, G, T, Y, A, and K;

j) at position 6 when compared to SEQ ID NO: 39, wherein the substituting amino acid residue is F;

k) at position 7 when compared to SEQ ID NO: 39, wherein the substituting amino acid residue is selected from the group consisting of G, Q, L, and S.

l) at position 8 when compared to SEQ ID NO: 39, wherein the substituting amino acid residue is selected from the group consisting of G, Q, Y, W, H, and L;

m) at position 9 when compared to SEQ ID NO: 39, wherein the substituting amino acid residue is selected from the group consisting of A, P, and S.

n) at position 3 when compared to SEQ ID NO: 49, wherein the substituting amino acid residue is L;

o) at position 5 when compared to SEQ ID NO: 49, wherein the substituting amino acid residue is T;

p) at position 6 when compared to SEQ ID NO: 49, wherein the substituting amino acid residue is selected from the group consisting of N, D, and K;

q) at position 2 when compared to SEQ ID NO: 88, wherein the substituting amino acid residue is selected from the group consisting of S, P and T;

r) at position 6 when compared to SEQ ID NO: 88, wherein the substituting amino acid residue is R;

s) at position 8 when compared to SEQ ID NO: 88, wherein the substituting amino acid residue is selected from the group consisting of N, W, and T;

t) at position 9 when compared to SEQ ID NO: 88, wherein the substituting amino acid residue is A;

u) at position 2 when compared to SEQ ID NO: 101, wherein the substituting amino acid residue is selected from the group consisting of M, A, and L;

v) at position 3 when compared to SEQ ID NO: 101, wherein the substituting amino acid residue is C;

w) at position 4 when compared to SEQ ID NO: 101, wherein the substituting amino acid residue is Y;

x) at position 7 when compared to SEQ ID NO: 101, wherein the substituting amino acid residue is N; and y) at position 8 when compared to SEQ ID NO: 101, wherein the substituting amino acid residue is D.

In some embodiments, the CDRL3 comprises an amino acid sequence selected from the group consisting of SEQ ID NOs: 1-12, 14-24, 26-38, 40-48, 50-87, and 89-100. In some embodiments, the CDRL3 comprises an amino acid sequence selected from the group consisting of SEQ ID NOs: 1-12, 14-24, 26-38, 40-48, 50-51, and 89-100.

In some embodiments, the VL comprises an amino acid sequence selected from the group consisting of SEQ ID NOs: 119-1693.

In some embodiments, the CDRL3 comprises an amino acid sequence selected from SEQ ID NOs: 13, 25, 39, 49, 88, 101, and 1883-1888. In some embodiments, the CDRL1 comprises an amino acid sequence selected from SEQ ID NOs: 13120-13125. In some embodiments, the CDRL2 comprises an amino acid sequence selected from SEQ ID NOs: 13126-13131.

In some embodiments, the VL comprises an amino acid sequence selected from SEQ ID NOs: 119, 227, 242, 351, 1399, 1406, and 1899-1904.

In some embodiments, the CDRH3 comprises at least one amino acid substitution when compared to SEQ ID NO: 104, 110, 1817, 1818, 1819, or 1820. In some embodiments, the at least one amino acid substitution is selected from the group consisting of a) at position 3 when compared to SEQ ID NO: 104, wherein the substituting amino acid residue is G or I;

b) at position 4 when compared to SEQ ID NO: 104, wherein the substituting amino acid residue is S, T, or P;

c) at position 9 when compared to SEQ ID NO: 104, wherein the substituting amino acid residue is A;

d) at position 11 when compared to SEQ ID NO: 104, wherein the substituting amino acid residue is K or H;

e) at position 14 when compared to SEQ ID NO: 104, wherein the substituting amino acid residue is L;

f) at position 16 when compared to SEQ ID NO: 104, wherein the substituting amino acid residue is L or T;

g) at position 1 when compared to SEQ ID NO: 110, wherein the substituting amino acid residue is T or S;

h) at position 5 when compared to SEQ ID NO: 110, wherein the substituting amino acid residue is N or P;

i) at position 7 when compared to SEQ ID NO: 110, wherein the substituting amino acid residue is I, N, K, or L;

j) at position 9 when compared to SEQ ID NO: 110, wherein the substituting amino acid residue is L or T;

k) at position 10 when compared to SEQ ID NO: 110, wherein the substituting amino acid residue is A or V;

l) at position 11 when compared to SEQ ID NO: 110, wherein the substituting amino acid residue is L.

m) at position 17 when compared to SEQ ID NO: 110, wherein the substituting amino acid residue is S;

n) at position 19 when compared to SEQ ID NO: 110, wherein the substituting amino acid residue is D; and o) at position 20 when compared to SEQ ID NO: 110, wherein the substituting amino acid residue is S.

In some embodiments, the CDRH3 comprises an amino acid sequence selected from the group consisting of SEQ ID NOs: 102-103, 105-109, and 111-118.

In some embodiments, the VH comprises an amino acid sequence selected from the group consisting of SEQ ID NOs: 1694-1756.

In some embodiments, the CDRH3 comprises an amino acid sequence selected from the group consisting of SEQ ID NOs: 104, 110, and 1817-1822. In some embodiments, the CDRH1 comprises an amino acid sequence selected from SEQ ID NOs: 13102-13107. In some embodiments, the CDRH2 comprises an amino acid sequence selected from SEQ ID NOs: 13108-13113.

In some embodiments, the CDRH3 comprises an amino acid sequence selected from the group consisting of SEQ ID NOs: 13138-13143, 13148-13150, and 13153-13155.

In some embodiments, the CDRL3 comprises an amino acid sequence selected from the group consisting of SEQ ID NOs: 13151 and 13152.

In some embodiments, the recombinant antibody disclosed herein comprises an amino acid sequence selected from SEQ ID NOs: 13144, 13145, 13146, and 13147.

In some embodiments, the VH comprises an amino acid sequence selected from the group consisting of SEQ ID NOs: 1895-1898, 1694, and 1718.

In some embodiments, the recombinant antibody disclosed herein is selected from the group consisting of a) a recombinant antibody comprising the CDRL3 of SEQ ID NO: 88 or 1887 and the CDRH3 of SEQ ID NO: 104 or 1821;

b) a recombinant antibody comprising the CDRL3 of SEQ ID NO: 101 or 1888 and the CDRH3 of SEQ ID NO: 110 or 1822;

c) a recombinant antibody comprising the CDRL3 of SEQ ID NO: 13 or 1883 and the CDRH3 of SEQ ID NO: 1817;

d) a recombinant antibody comprising the CDRL3 of SEQ ID NO: 25 or 1884 and the CDRH3 of SEQ ID NO: 1818;

e) a recombinant antibody comprising the CDRL3 of SEQ ID NO: 39 or 1885 and the CDRH3 of SEQ ID NO: 1819; and f) a recombinant antibody comprising the CDRL3 of SEQ ID NO: 49 or 1886 and the CDRH3 of SEQ ID NO: 1820.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13102,
CDRH2 is SEQ ID NO: 13108,
CDRH3 is SEQ ID NO: 1817,
CDRL1 is SEQ ID NO: 13120,
CDRL2 is SEQ ID NO: 13126, and
CDRL3 is SEQ ID NO: 13 or 1883.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13103,
CDRH2 is SEQ ID NO: 13109,
CDRH3 is SEQ ID NO: 1818,
CDRL1 is SEQ ID NO: 13121,
CDRL2 is SEQ ID NO: 13127, and
CDRL3 is SEQ ID NO: 25 or 1884.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13104,
CDRH2 is SEQ ID NO: 13110,
CDRH3 is SEQ ID NO: 1819,
CDRL1 is SEQ ID NO: 13122,
CDRL2 is SEQ ID NO: 13128, and
CDRL3 is SEQ ID NO: 39 or 1885.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13105,
CDRH2 is SEQ ID NO: 13111,
CDRH3 is SEQ ID NO: 1820,
CDRL1 is SEQ ID NO: 13123,
CDRL2 is SEQ ID NO: 13129, and
CDRL3 is SEQ ID NO: 49 or 1886.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13106,
CDRH2 is SEQ ID NO: 13112,
CDRH3 is SEQ ID NO: 104 or 1821,
CDRL1 is SEQ ID NO: 13124,
CDRL2 is SEQ ID NO: 13130, and
CDRL3 is SEQ ID NO: 88 or 1887.

In some embodiments, the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is SEQ ID NO: 13107,
CDRH2 is SEQ ID NO: 13113,
CDRH3 is SEQ ID NO: 110 or 1822,
CDRL1 is SEQ ID NO: 13125,
CDRL2 is SEQ ID NO: 13131, and
CDRL3 is SEQ ID NO: 101 or 1888.

In some embodiments, the recombinant antibody binds to at least one HIV antigen and/or at least one HCV antigen.

In some aspects, disclosed herein is a method of producing a recombinant antibody comprising cultivating or maintaining the host cell of any preceding aspect under conditions to produce said recombinant antibody.

In some aspects, disclosed herein is a method of treating, preventing, reducing, and/or inhibiting HIV/HCV co-infection comprising administering to a subject a therapeutically effective amount of the recombinant antibody of any preceding aspect.

In some aspects, disclosed herein is a method of treating, preventing, reducing, and/or inhibiting HIV infection comprising administering to a subject a therapeutically effective amount of the recombinant antibody of any preceding aspect.

In some aspects, disclosed herein is a method of treating, preventing, reducing, and/or inhibiting HCV infection comprising administering to a subject a therapeutically effective amount of the recombinant antibody of any preceding aspect.

EXAMPLES

The following examples are set forth below to illustrate the antibodies, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. HIV/HCV Cross-Reactive Antibodies

Investigating the human antibody response to HIV and HCV has led to significant advances towards preventative therapeutics and vaccines against these highly mutable pathogens. Yet, despite the high prevalence of HIV/HCV co-infection, little is known about antibody responses in this context. Hence, the effect of chronic co-infection with HIV and HCV on the development of virus-specific humoral responses is investigated. The present disclosure shows that chronic HIV/HCV co-infection leads to the development of HIV and HCV cross-reactive antibodies and that these antibodies evolve from polyreactive precursors or from one virus-specific lineage that acquires additional specificity through hypermutation. Gaining such an understanding provides insights into the interplay between the pathogen-specific portions of the antibody repertoires in co-infected individuals, and also provides significant implications for how antibody-specific vaccine development can be adapted to fit the specific immunological requirements during chronic co-infection. Accordingly, the antibody repertoires of HIV/HCV co-infected individuals were investigated, for which there are samples available from multiple timepoints.

Antibody responses to HIV and HCV on their own have been studied extensively, revealing a potential for such antibodies as therapeutics and as targets for antibody-specific vaccine development. The analysis herein investigates the chronic infection timepoints at which both HIV-1 and HCV infections are already present. While a comparison to pre-infection timepoints for one or both infections, or timepoints after HCV clearance, can provide additional details about the evolution of antibody repertoires in co-infection, recent studies have shown that the diversity and potency of HCV-specific antibody repertoires rapidly decline after HCV clearance in co-infected individuals.

The co-infection samples analyzed herein have diverse timepoint ranges, from up to 3 to >20 years post HIV-1 infection, consistent with the chronic timepoints used for successfully identifying broadly neutralizing antibodies (bNAbs) in HIV-only infection. Further, chronic infection timepoints are associated with persistent antigen exposure, which allows antibodies to acquire high levels of somatic hypermutation, leading to improved neutralization breadth and potency. Evidence from HIV-only work has shown that these antibodies can be of immense use as therapeutic and preventative tools for passive immunization in humans, as well as for defining antibody-specific vaccine templates capable of eliciting robust protective antibody responses upon immunization. To that end, it was investigated how chronic HIV/HCV coinfection, and therefore chronic stimulation with both HIV and HCV antigens, affects the development of neutralizing antibodies.

The examples herein address the interplay between HIV-specific and HCV-specific antibody lineages within a donor, generating novel insights into various factors, such as: (a) suppression of antibody lineages against one virus vs. the other, and (b) new epitopes that are targeted in a co-infection setting but not observed as immunodominant in samples from existing studies of HIV-only and HCV-only infections. Understanding such factors that pose different requirements for developing an effective HCV vaccine for individuals already infected with HIV-1 compared to individuals not infected with HIV-1 is of high significance. The identification of HIV/HCV cross-reactive antibodies provide new bNAb therapeutics that can neutralize both viruses, which has utility in passive immunization settings for co-infected individuals, analogously to the clinical applications of bNAbs in the HIV-only setting. Additionally, mapping the epitopes of the HIV/HCV cross-reactive antibodies provides for the identification of new epitope-specific vaccines that can protect against both viruses by eliciting such HIV/HCV cross-reactive antibodies.

Figure 1:
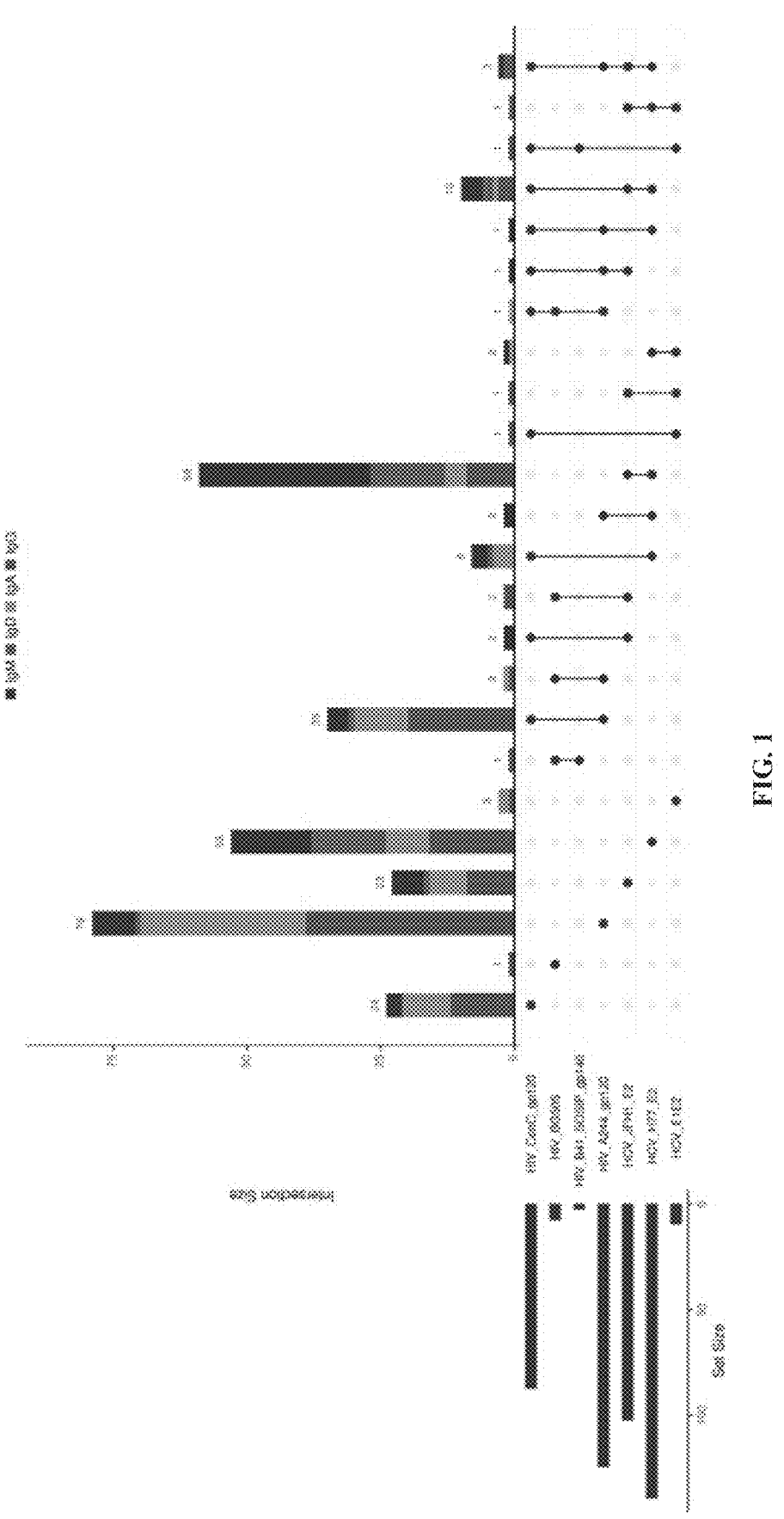
FIG. 1 shows that LIBRA-seq identifies spectrum of B cell specificity in HIV/HCV co-infection. Each sequenced cell is given a LIBRA-seq score for each antigen that defines its specificity. Shown here are the number of cells (intersection size) that were positive for a given specificity, shown underneath by shaded circles, colored by isotype frequency.
Figure 2:
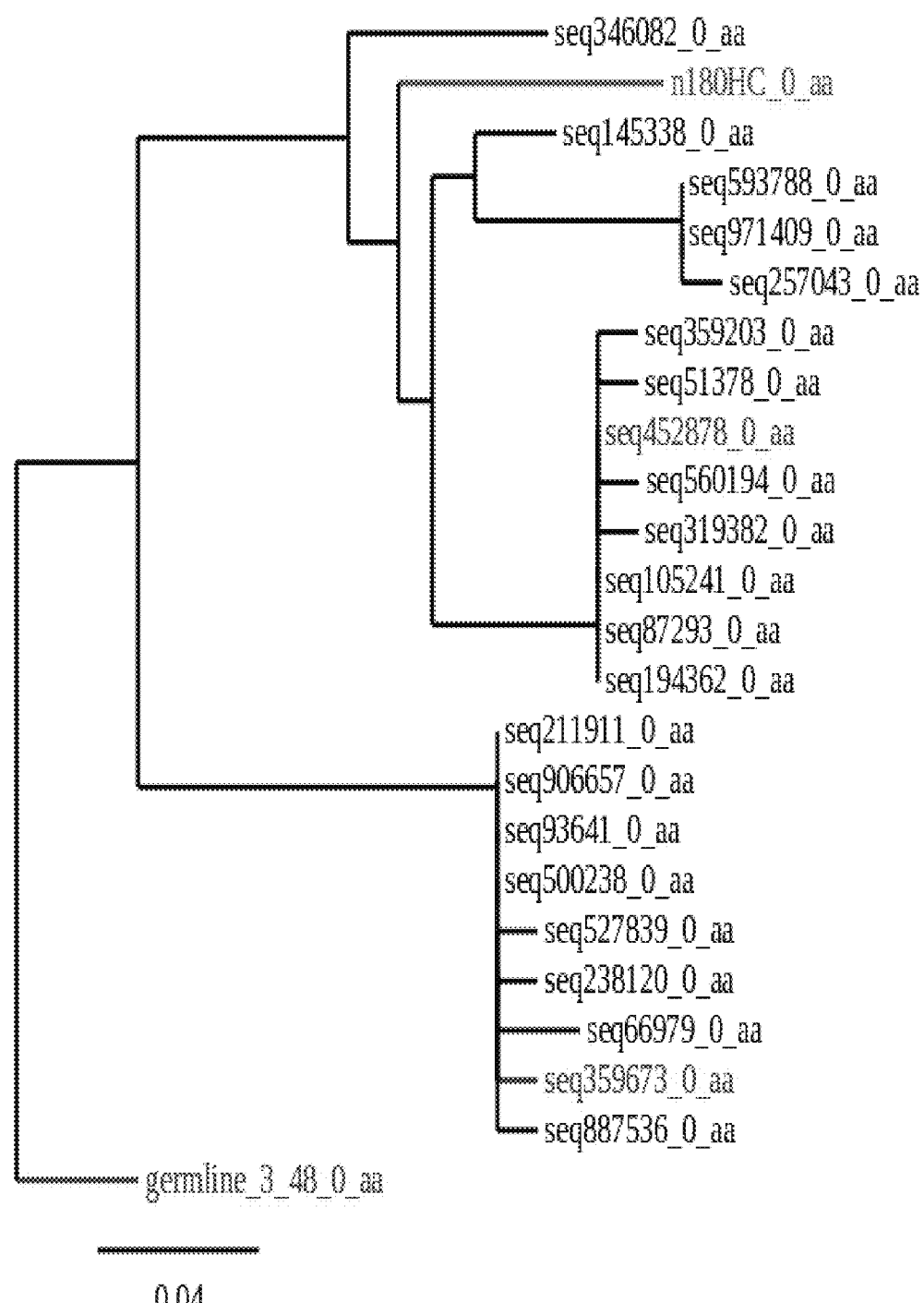
FIG. 2 shows phylogenetic analysis that identifies clonal relatives of HIV/HCV cross-reactive antibodies. Clonal relatives of HIV/HCV cross-reactive mAb180 were defined as sequences using the same V gene and sharing >70% CDRH3 identity. N180HC_0_aa denotes mAb180 isolated from 3.59ypi, all other sequences were identified 0.79ypi.
Figures 3, 4:
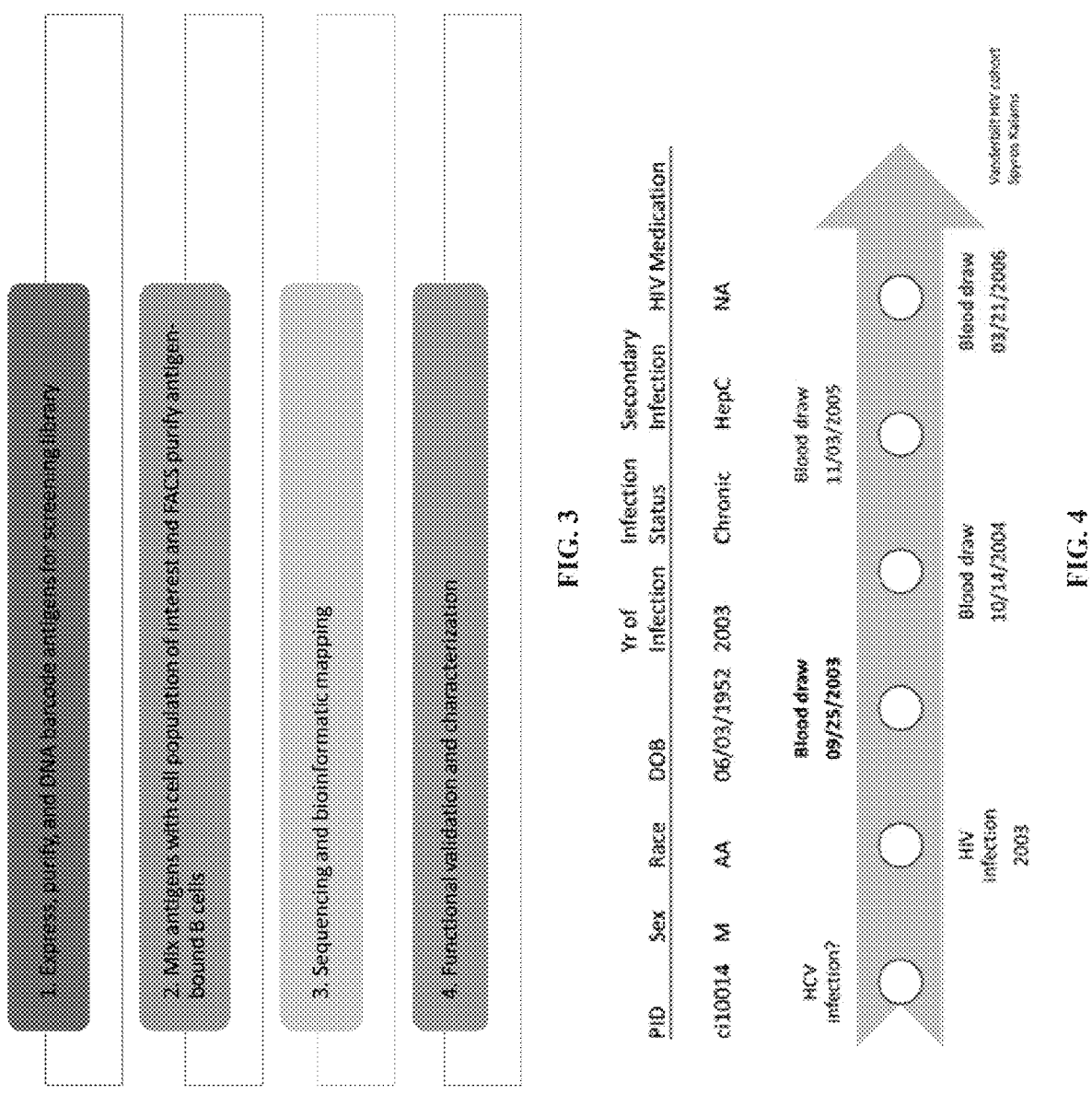
FIG. 3 shows an example workflow for LIBRA-seq experiments.
FIG. 4 shows that subsequent data was derived using a patient sample from a donor. Infection timepoints are shown. All LIBRA-seq data came from the Mar. 21, 2006 timepoint shown.
Figure 5:
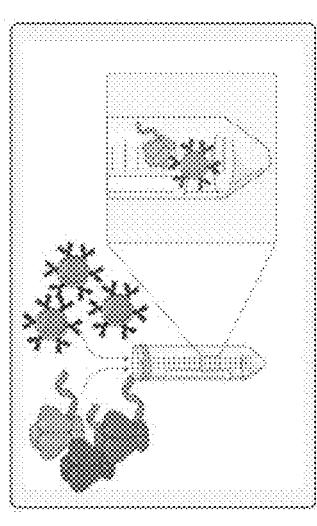
FIG. 5 shows experiment design. A diverse panel of HIV and HCV antigens were used to maximize the chance of pulling out HIV/HCV cross-reactive antibodies.
Figure 5:
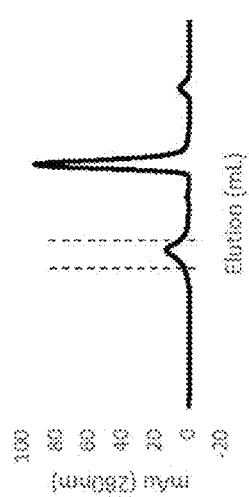
Figure 6:
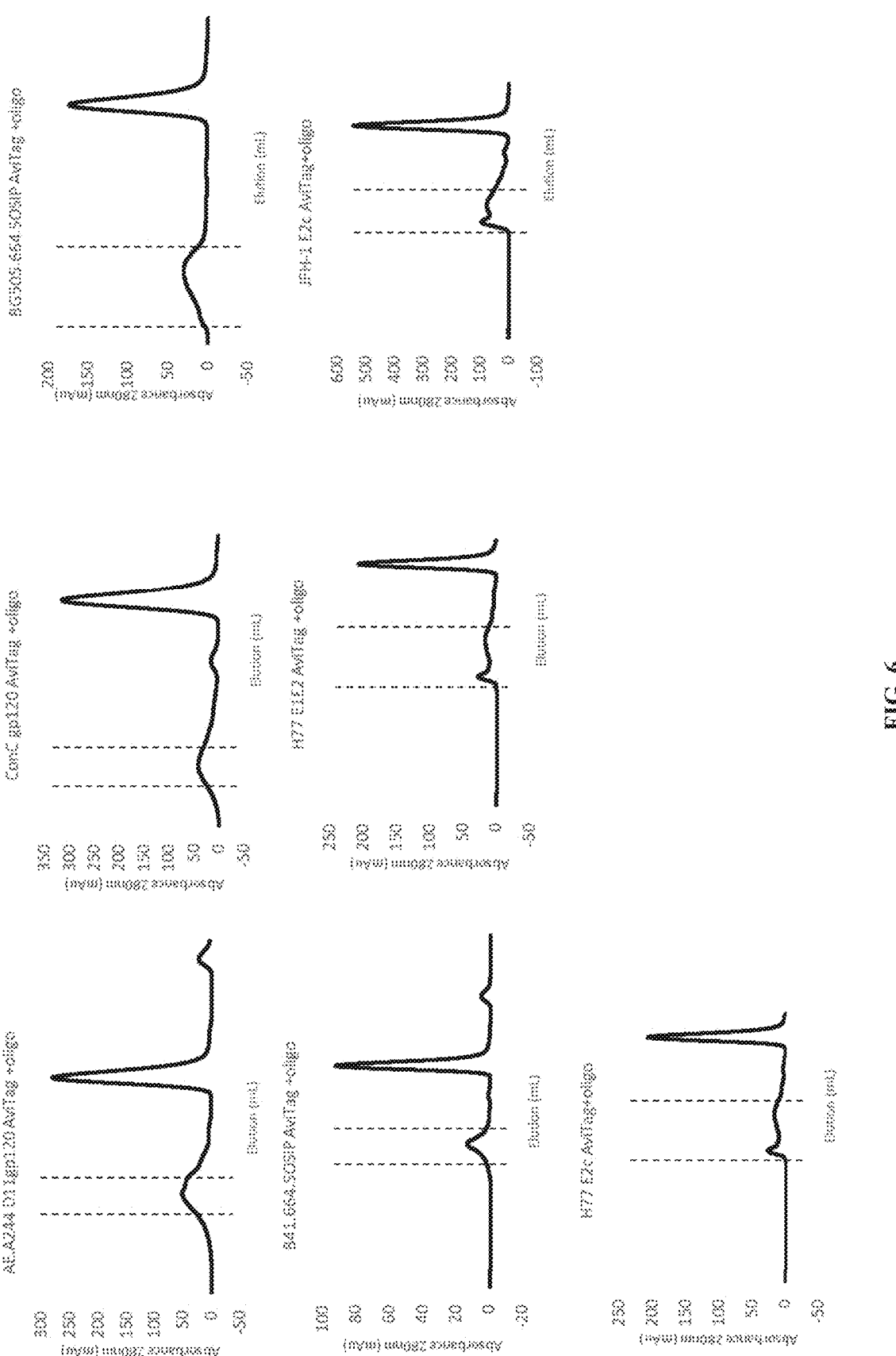
FIG. 6 shows LIBRA-seq works by tagging each antigen with its own unique oligonucleotide barcode. Only oligo-tagged antigens were purified by FPLC using a S200 SUPERDEX™ 10/300 GL column. Tagged antigens for sorting are denoted by dotted lines.
Figure 7:
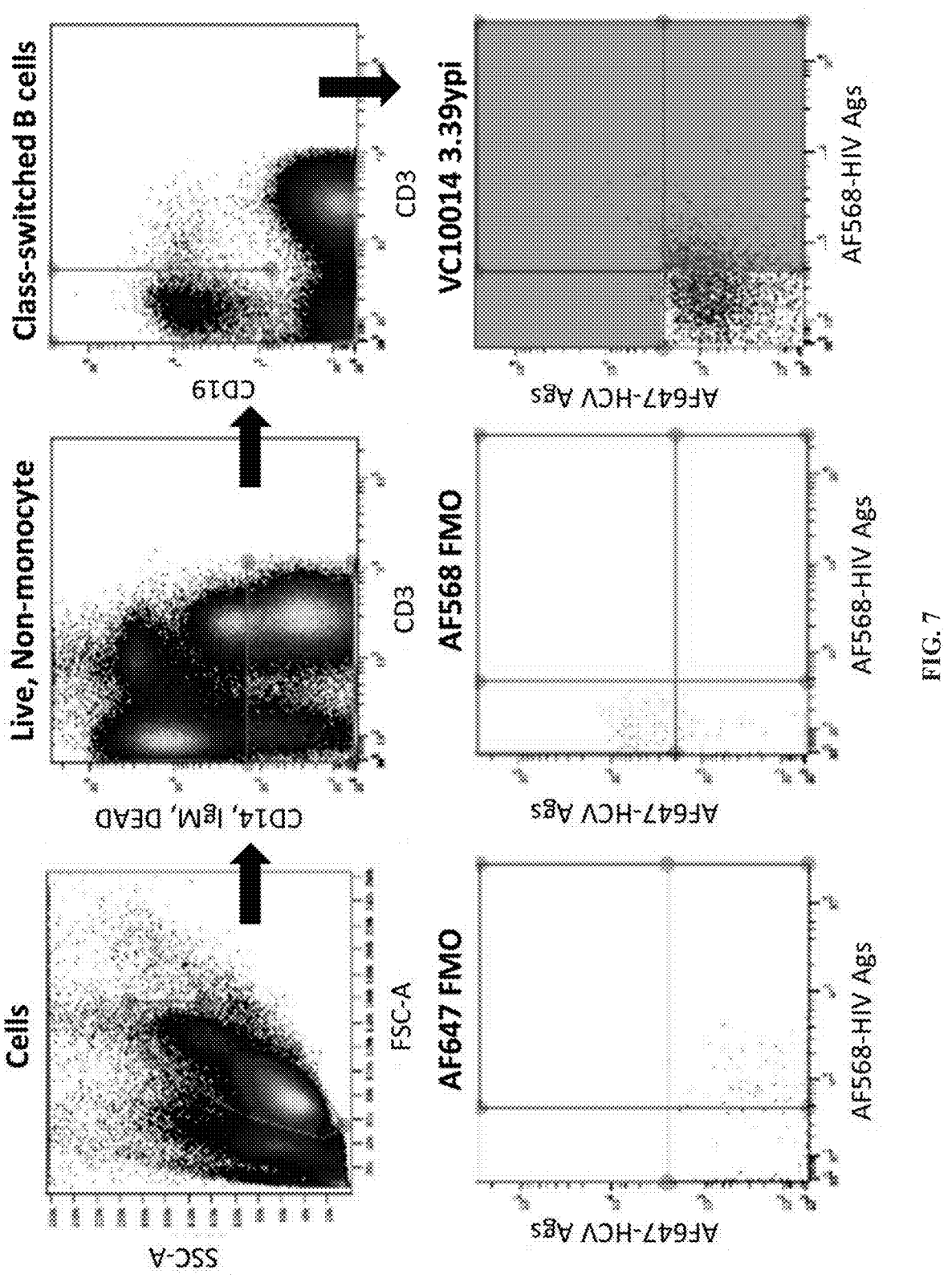
FIG. 7 shows Flow Sorting Strategy to Identify Antigen-specific B cells. B cells that have bound antigen were sorted out. B cells were separated from other cell populations using known markers. All cells that fall under the shaded squares were sorted for 10X sequencing.
Figure 8:
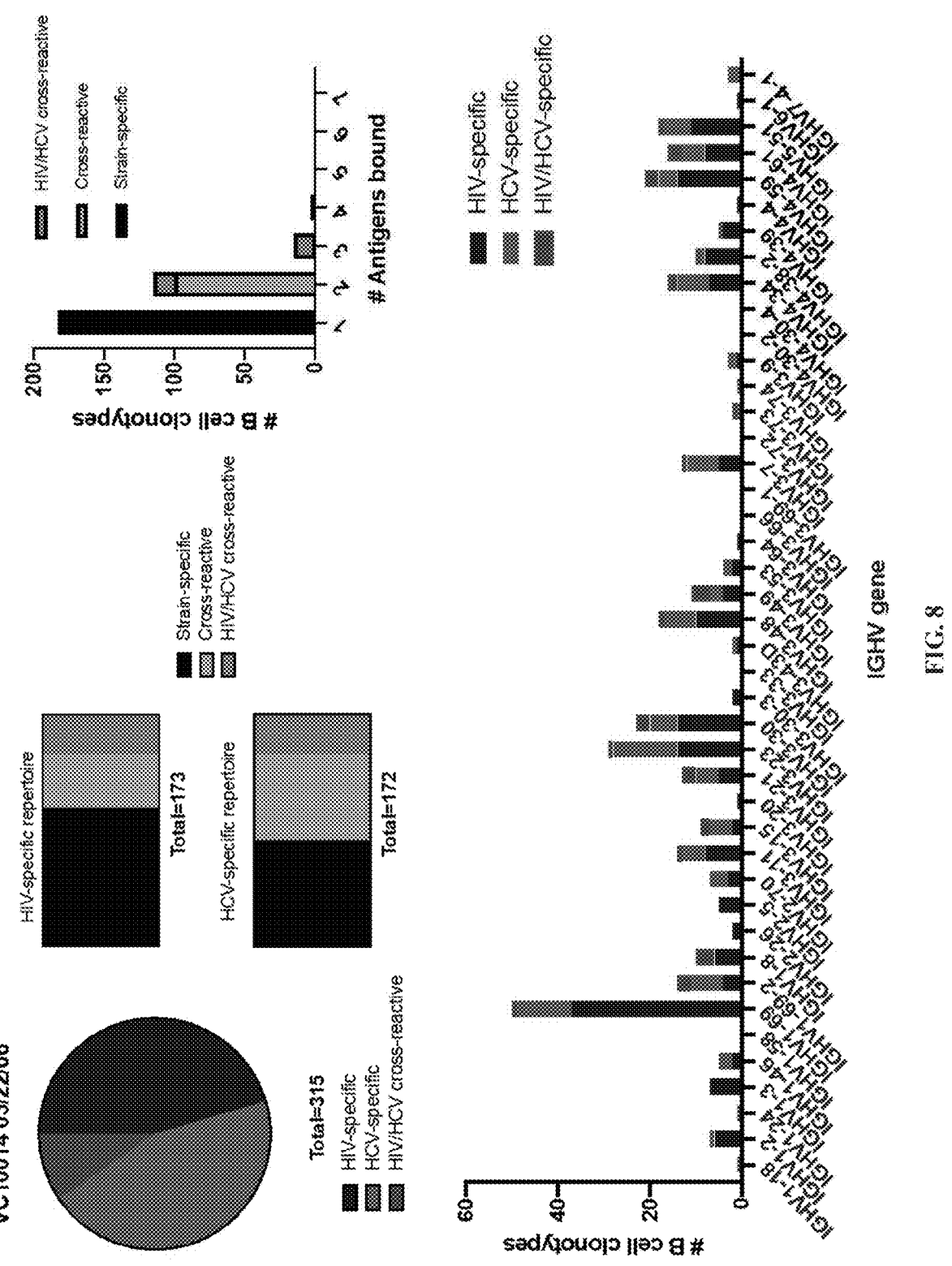
FIG. 8 shows that HIV/HCV cross-reactive antibodies make up ~9.5% of the data set.
Figure 8:
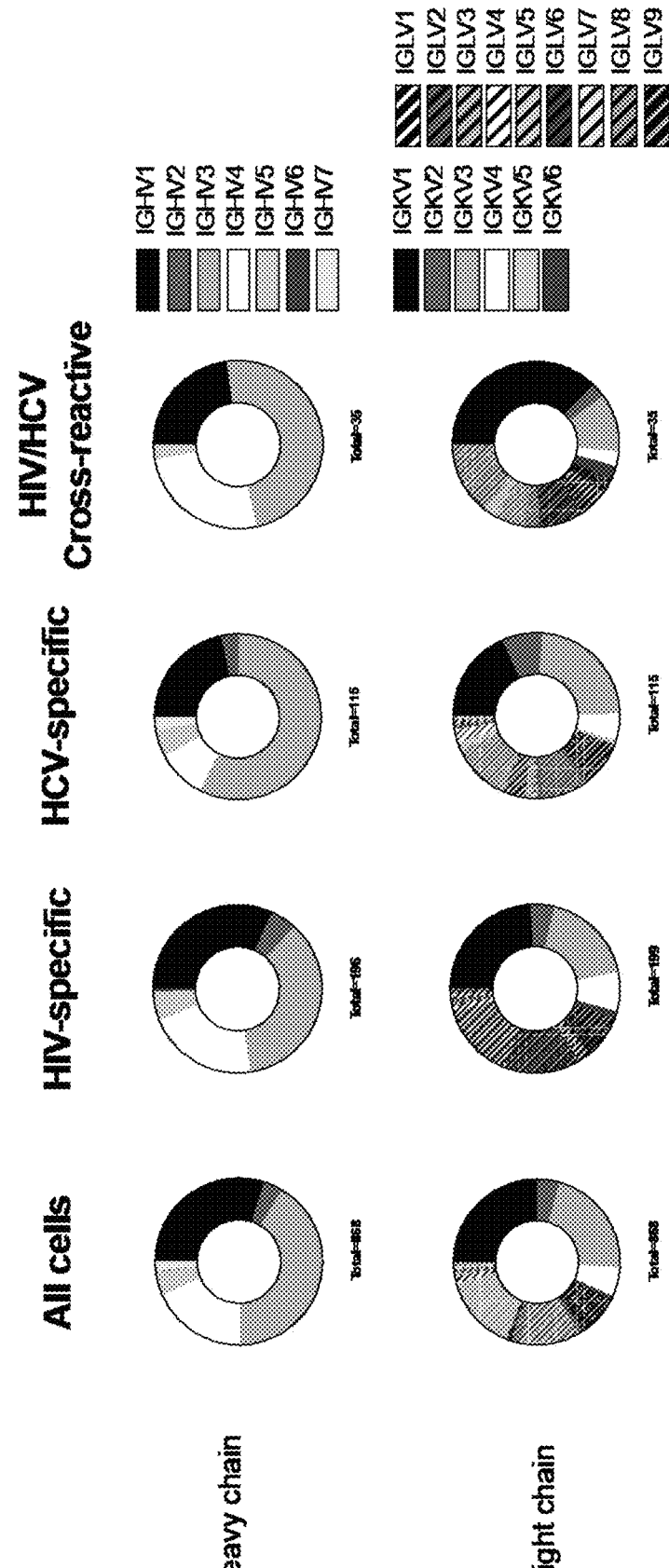
Figure 9:
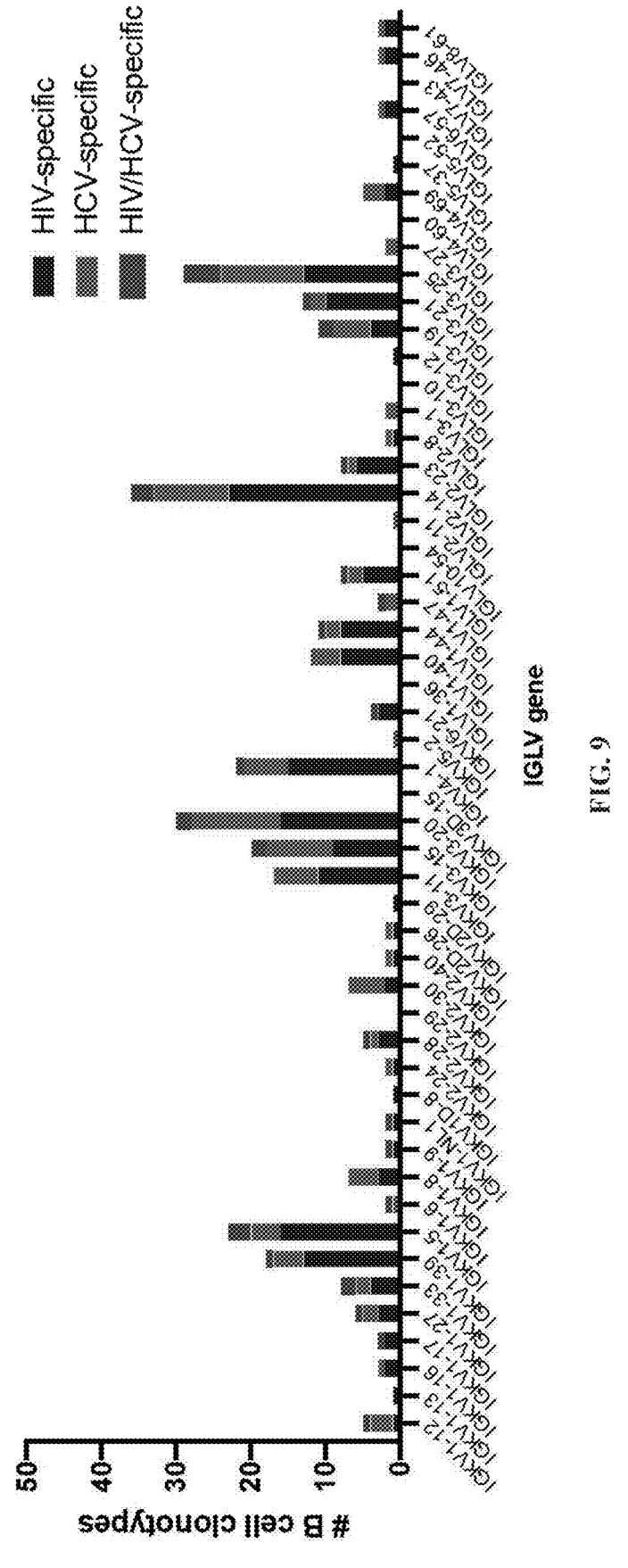
FIG. 9 shows that the LIBRA-seq data set uses diverse heavy and light chain variable genes.
Figure 10:
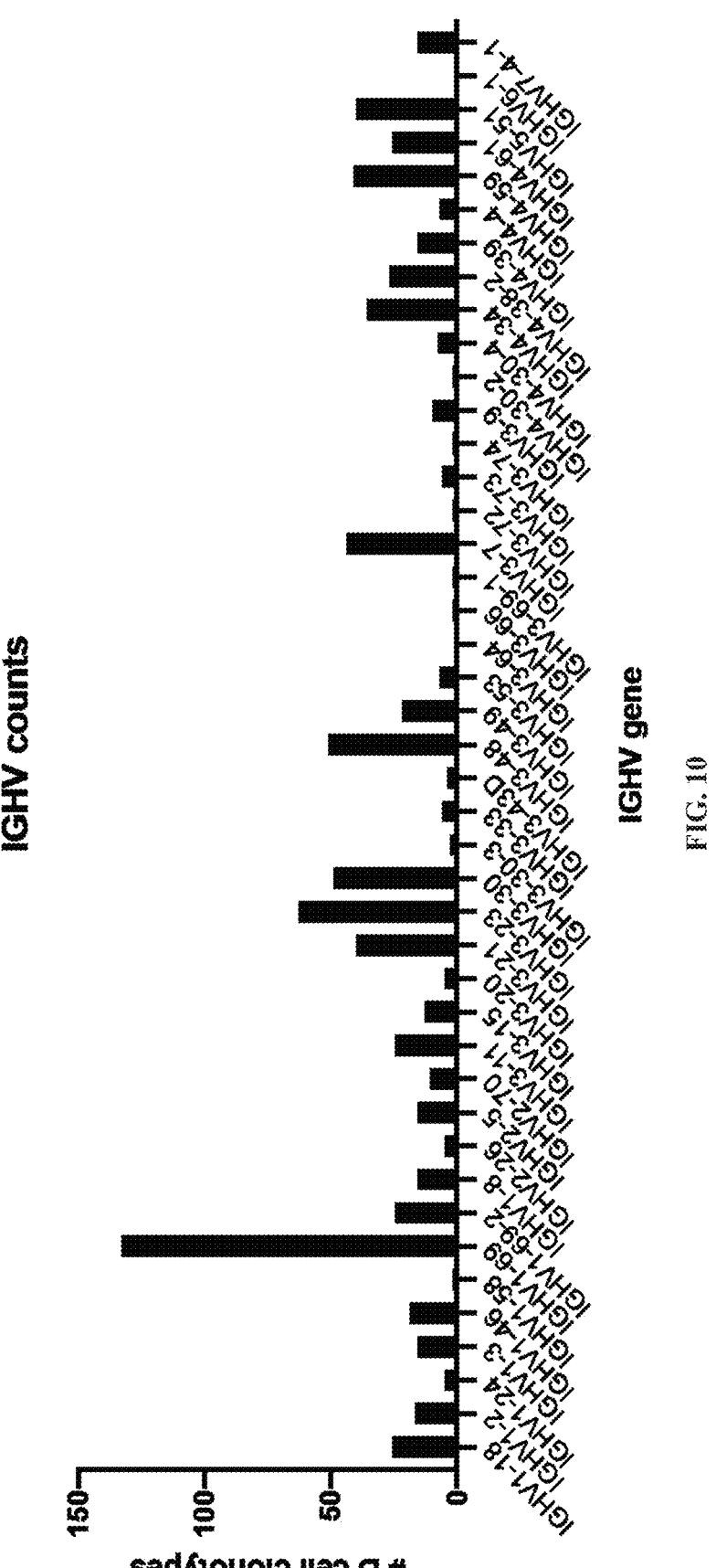
FIG. 10 shows that the LIBRA-seq data set uses diverse heavy chain variable genes (IGHV counts).
Figure 11:
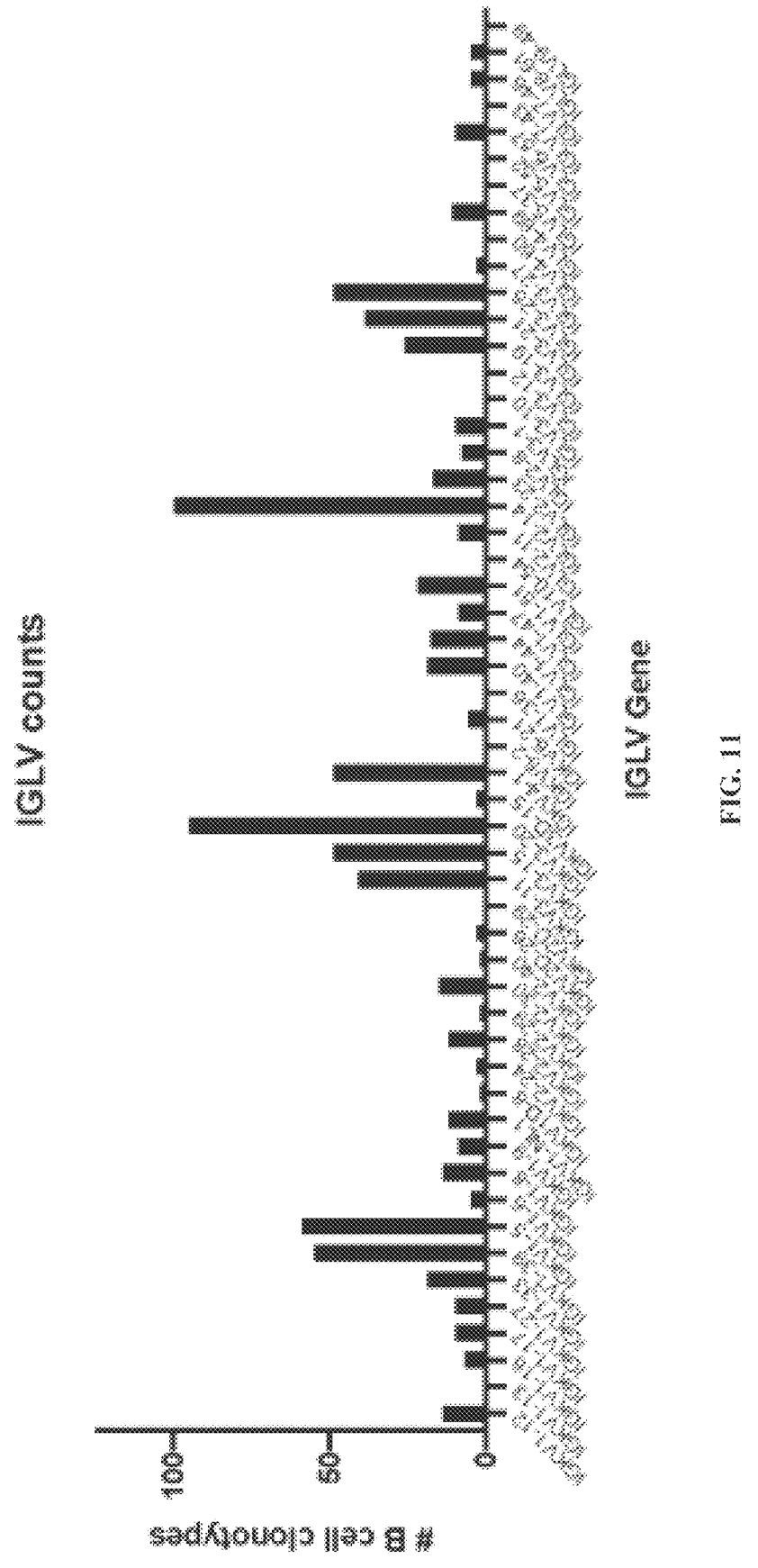
FIG. 11 shows that the LIBRA-seq data set uses diverse light chain variable genes (IGLV counts).
Figure 12:
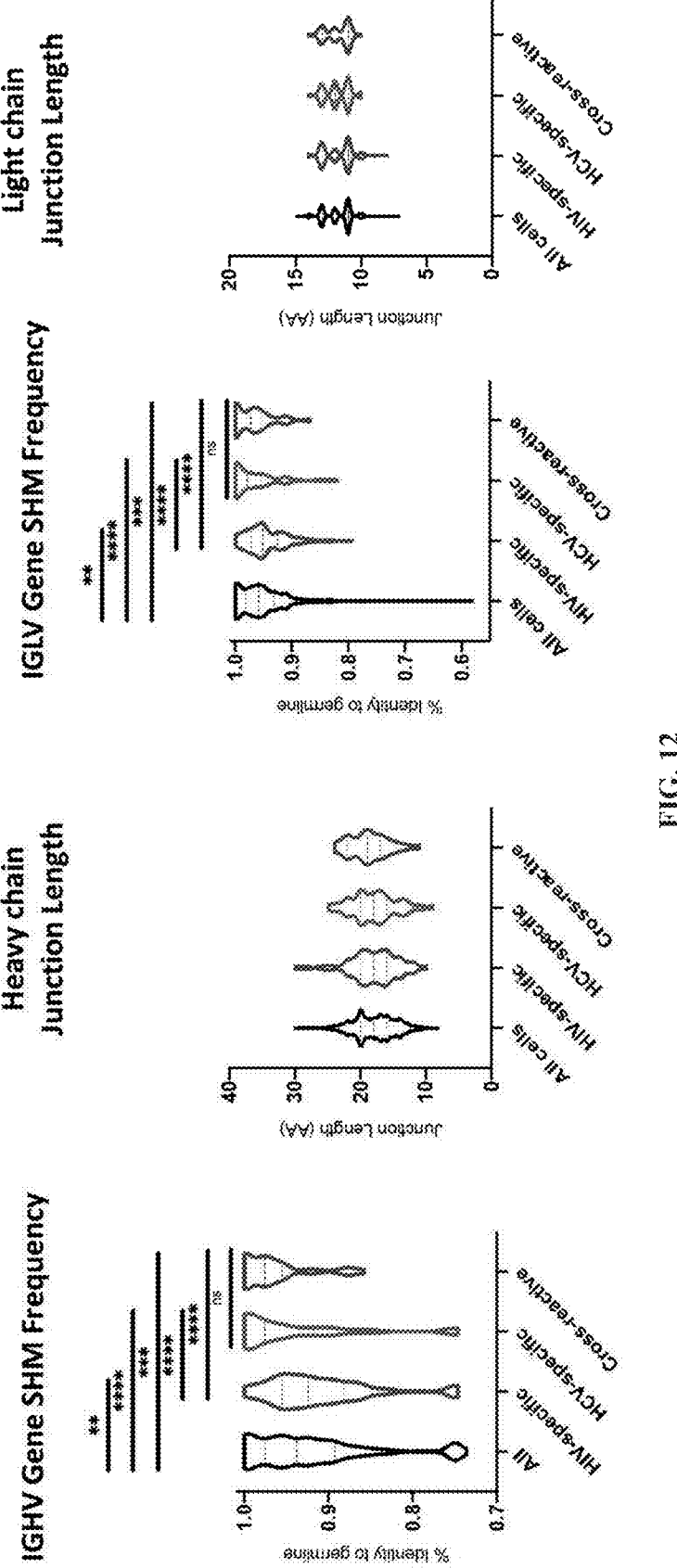
FIG. 12 shows that virus-specific antibodies have varying levels of somatic mutation.
Figure 13:
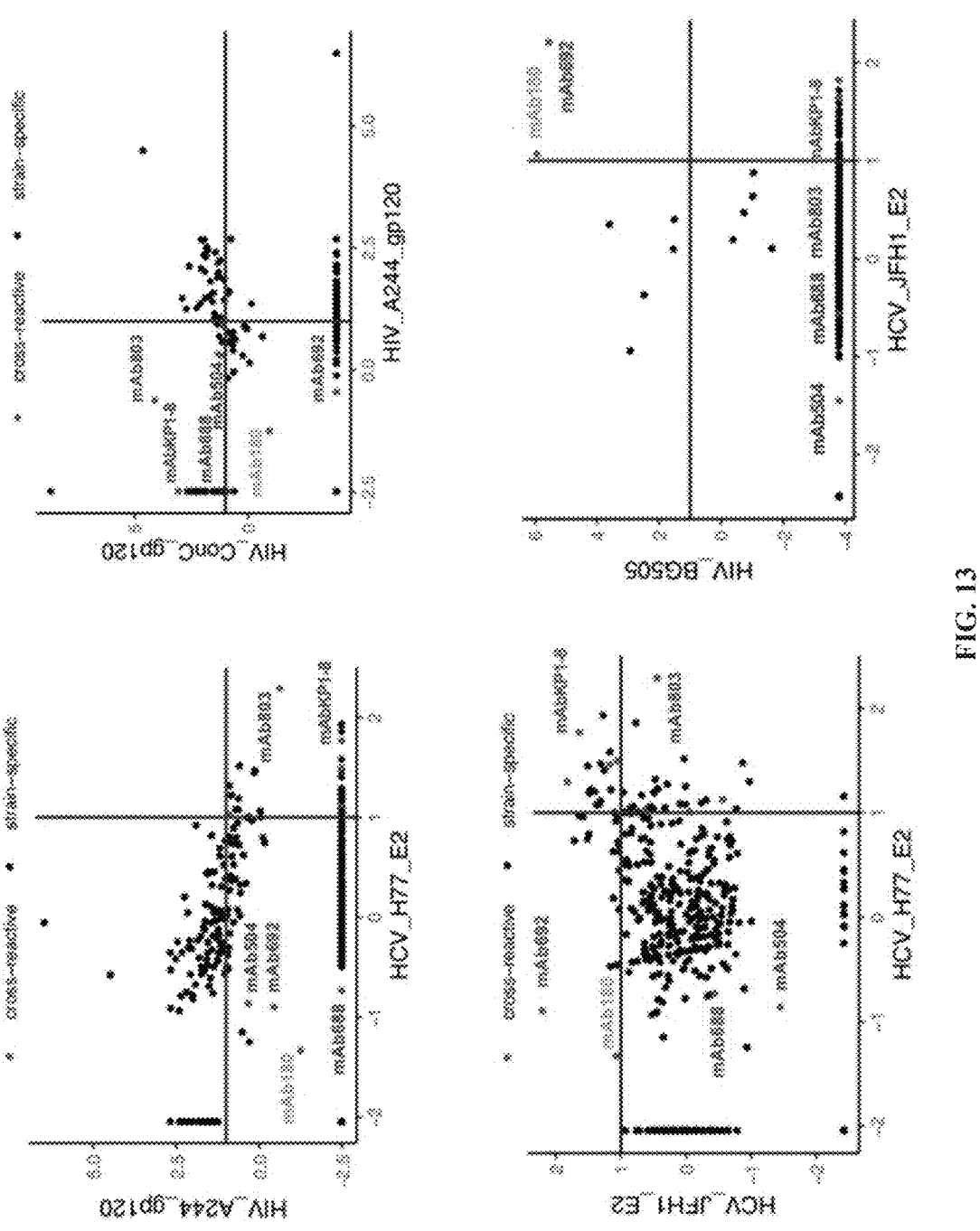
FIG. 13 shows HIV/HCV mAbs identified by high LIBRA-seq scores to HIV and HCV antigens. Each dot represents a single cell having the LIBRA-seq scores for the antigens shown on the x and y axes. HIV/HCV+ cells can be identified in quadrant I when plotting the LIBRA-seq scores for an HCV_and HIV_antigen shown by labeled dots.
Figure 13:
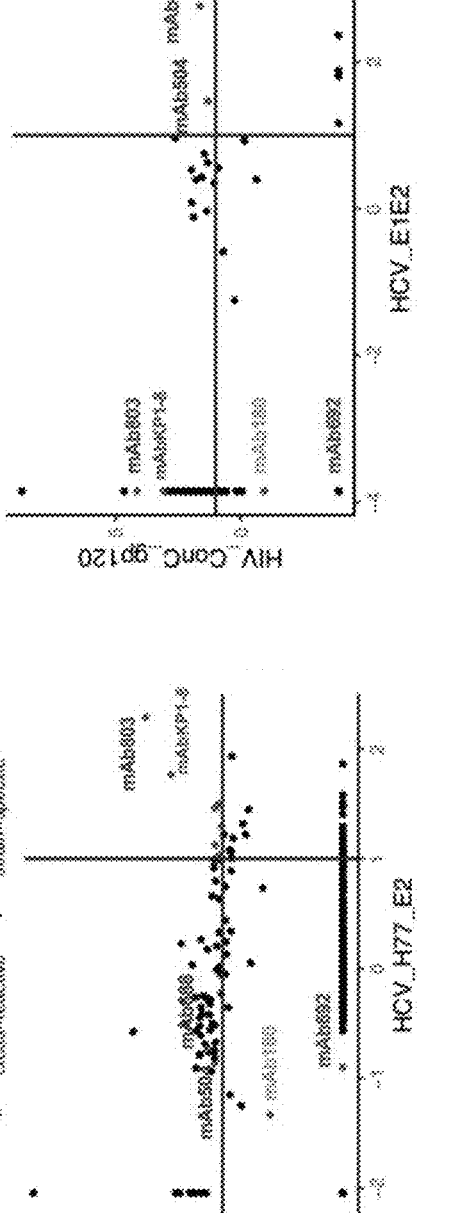
Figure 14:
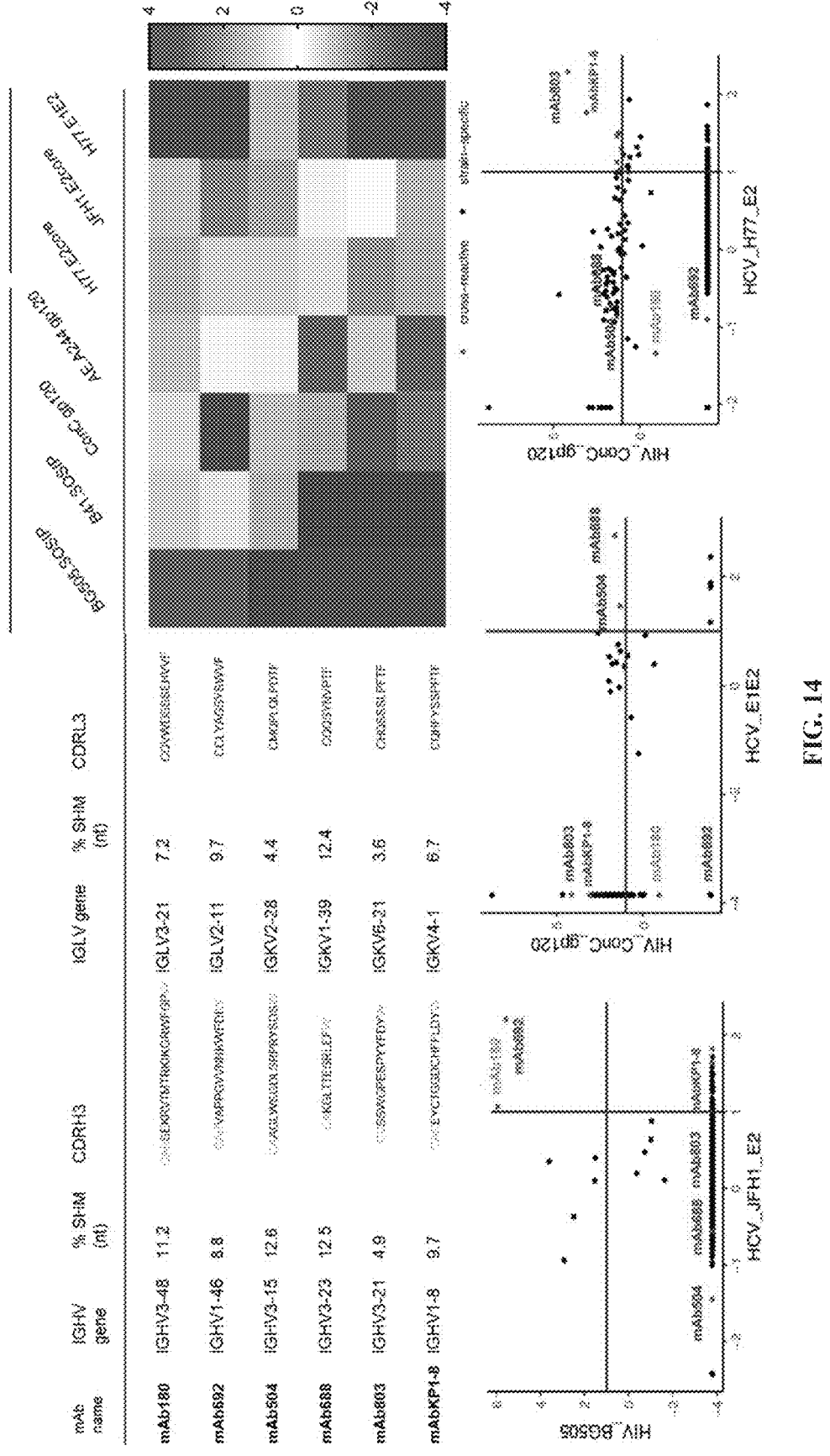
FIG. 14 shows genetic characteristics and LIBRA-seq scores for identified HIV/HCV mAbs (top). The LIBRA-seq scores for shown antigens are plotted against each other to identify HIV antigen and HCV antigen high cells (bottom). Sequences in FIG. 14: CARSEKRVTMTRKIKGRWFGPW (SEQ ID NO: 1822); CARVAPPGVVNNKWFDIW (SEQ ID NO: 1821); CAAGLWSGDLSRPRYSDSW (SEQ ID NO: 1817); CAKGLTTESRLEFW (SEQ ID NO: 1818); CVSSWGPESPYYFDYW (SEQ ID NO: 1819); CAREYC-TGGDCHFFLDYW (SEQ ID NO: 1820); CQVWDSSSEHVVF (SEQ ID NO: 1888); CCLYAGSYS-WVF (SEQ ID NO: 1887); CMQPLQLPDTF (SEQ ID NO: 1883); CQQSYNVPTF (SEQ ID NO: 1884); CHQSSSLPFTF (SEQ ID NO: 1885); CQHFYSSPPTF (SEQ ID NO: 1886).
Figure 15:
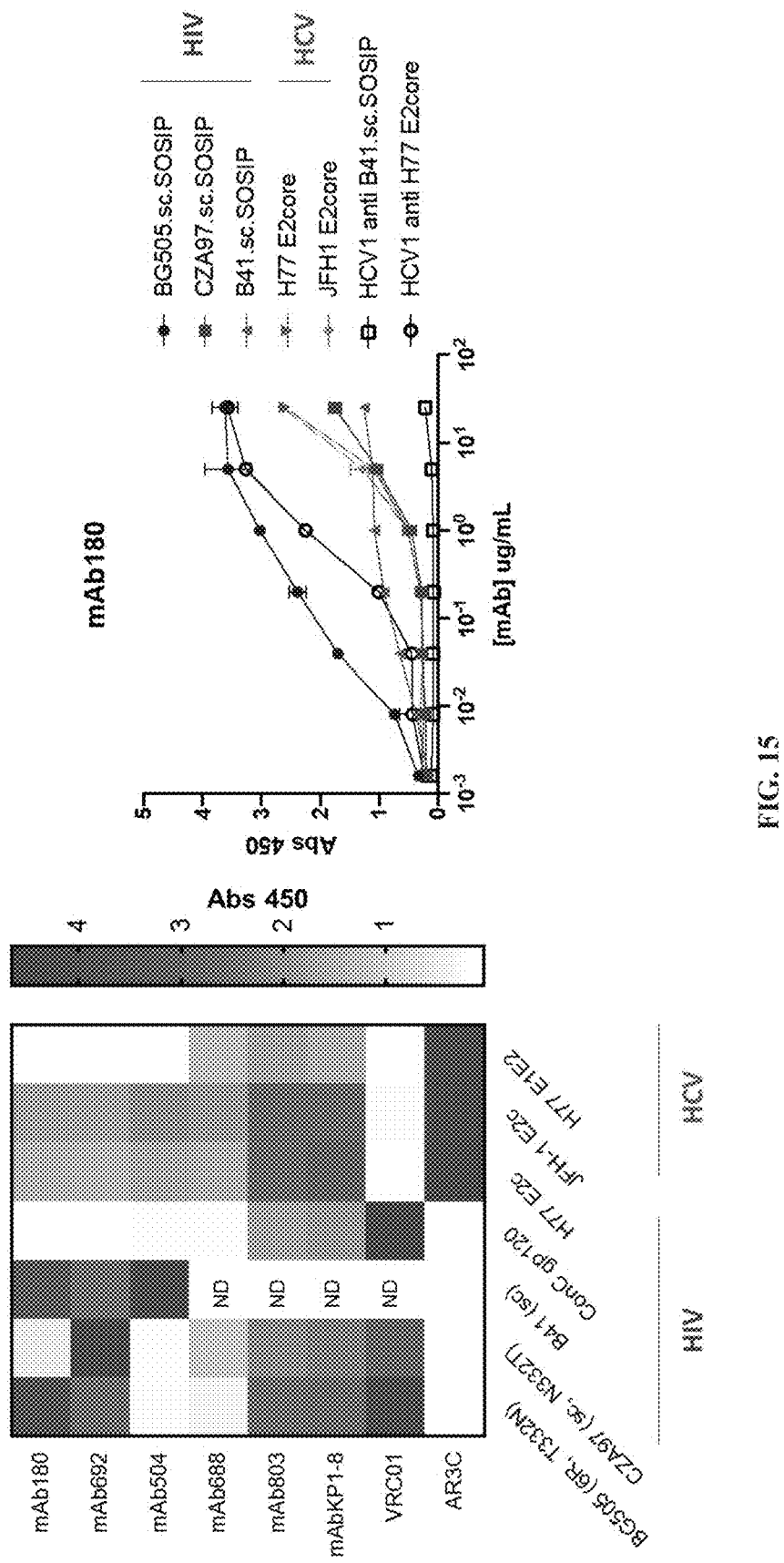
FIG. 15 shows recombinant expression confirms HIV/HCV cross-reactive binding.
Figure 16:
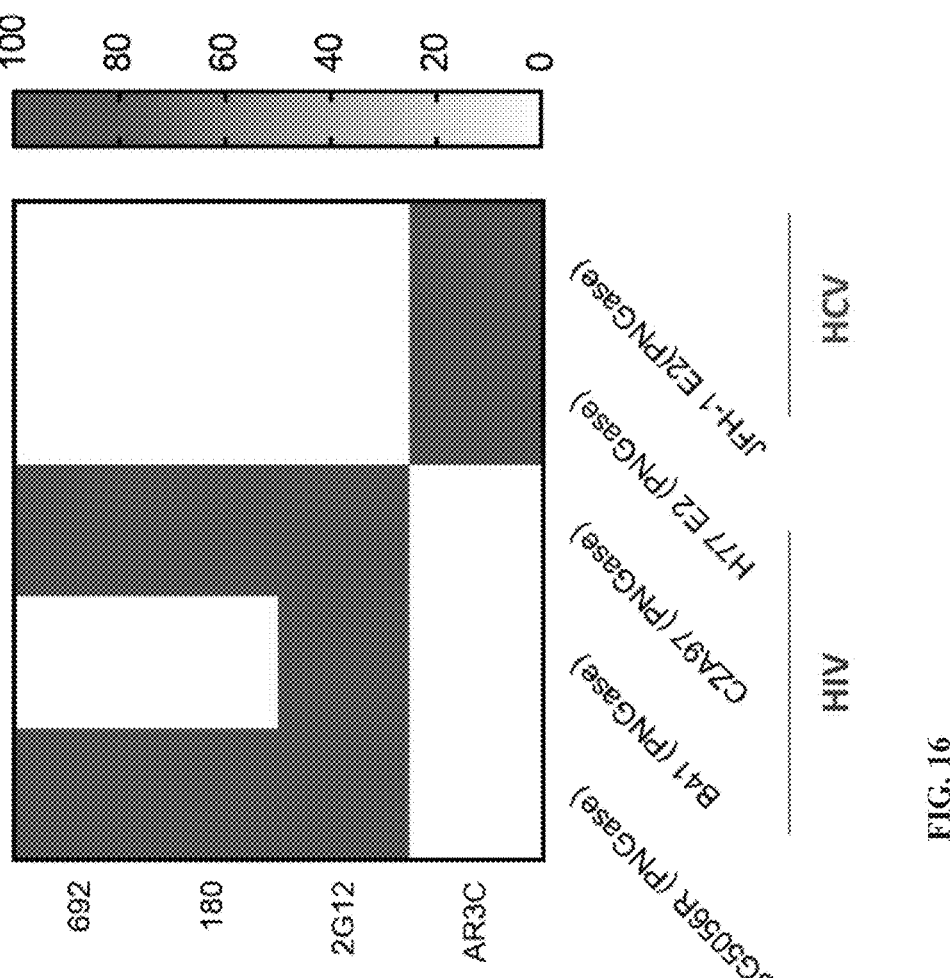
FIG. 16 depicts that HIV/HCV mAbs show strain-specific glycan dependence.
Figure 16:
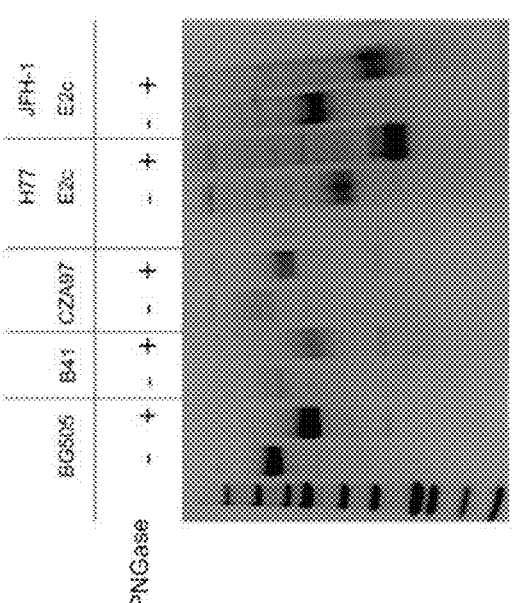
Figure 17:
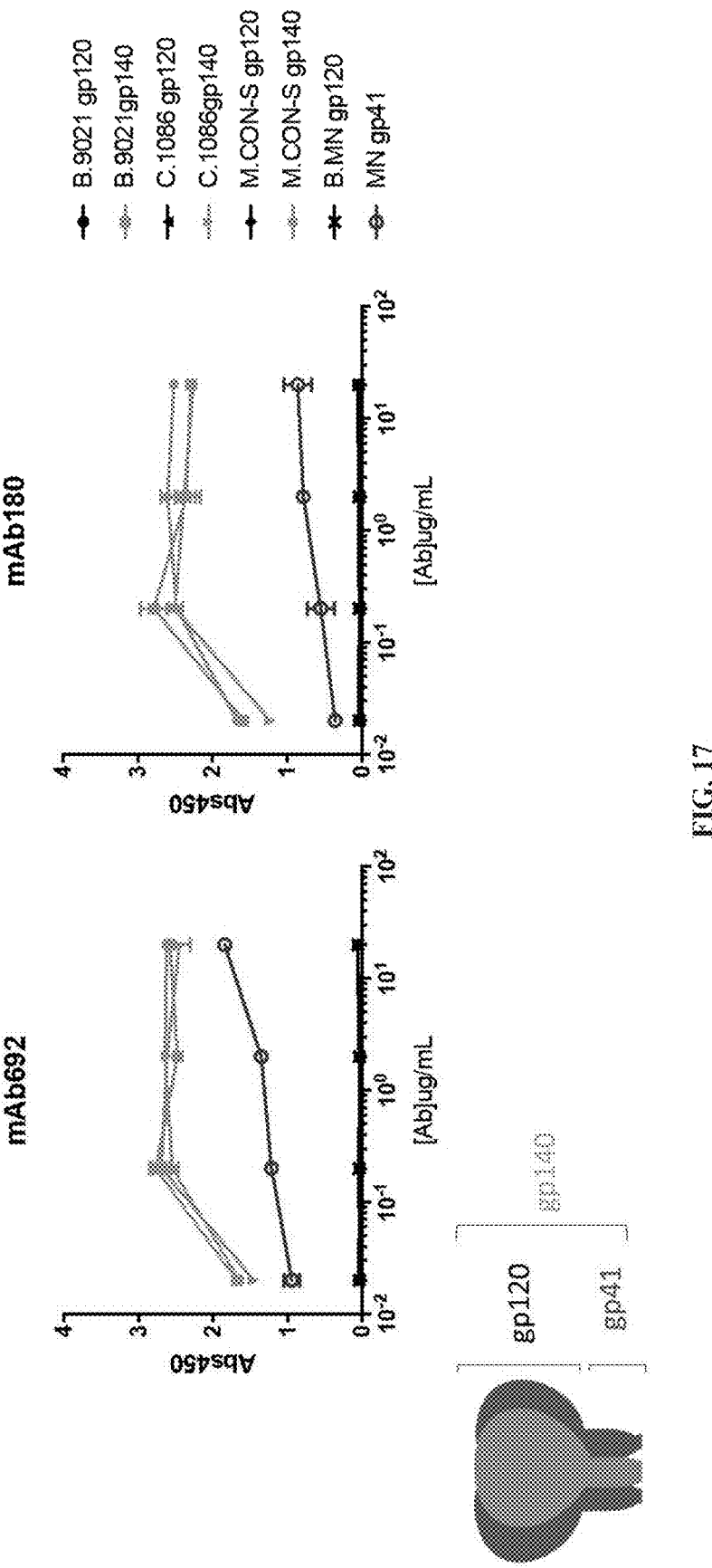
FIG. 17 shows that selected HIV/HCV cross-reactive mAbs are gp41-directed.
Figure 18:
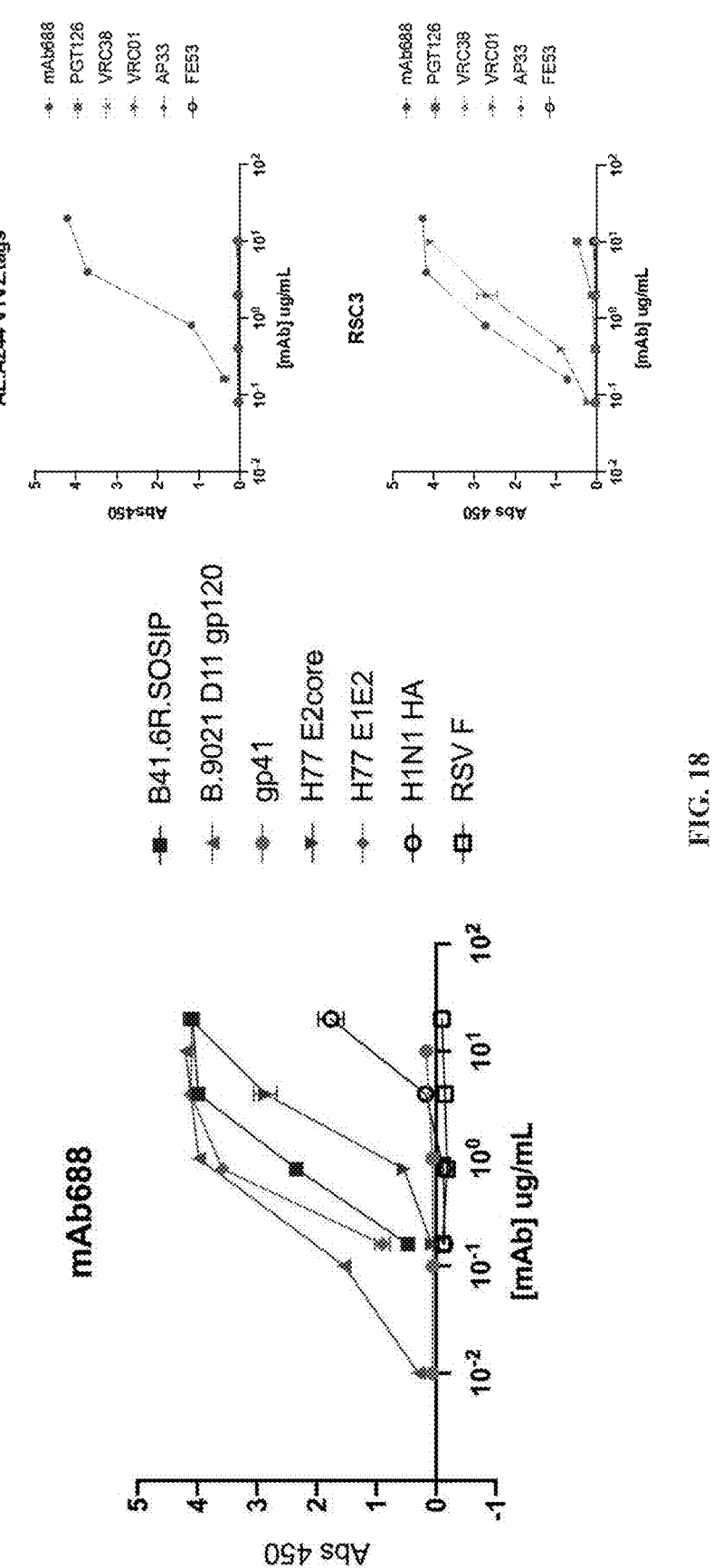
FIG. 18 shows that identified HIV/HCV cross-reactive antibodies can recognize multiple epitopes on HIV.
Figure 19:
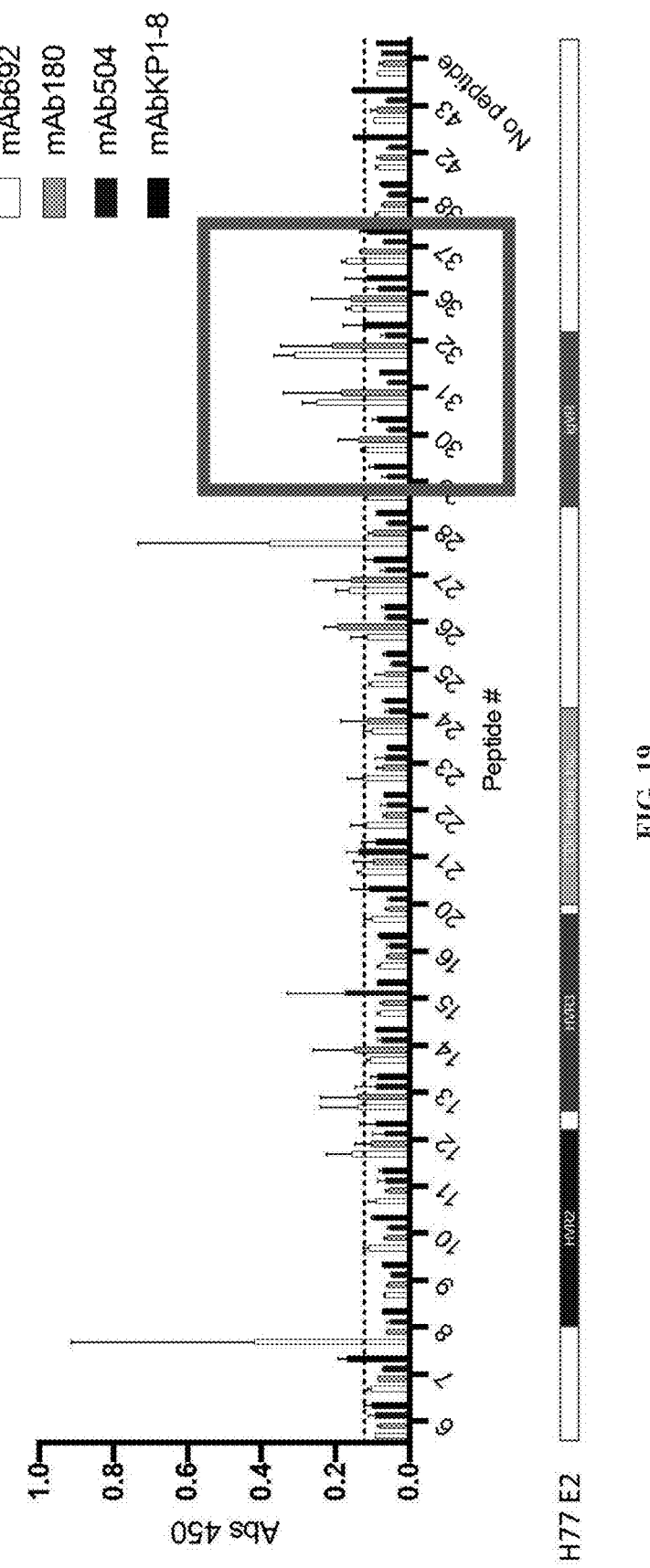
FIG. 19 shows that HIV/HCV cross-reactive mAbs recognize Antigenic Region 4.
Figure 20:
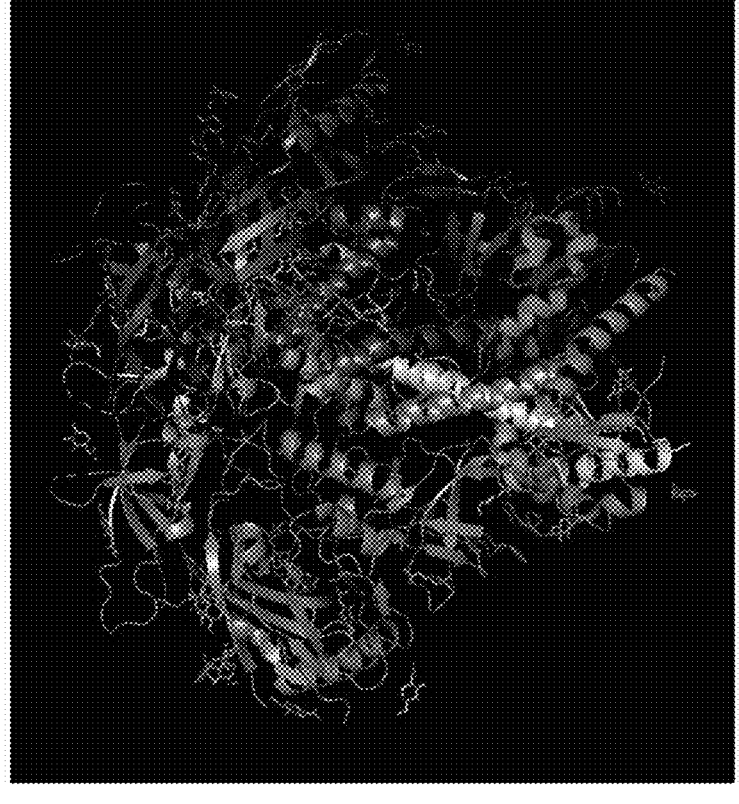
FIG. 20 shows predicted cross-reactive epitopes.
Figure 20:
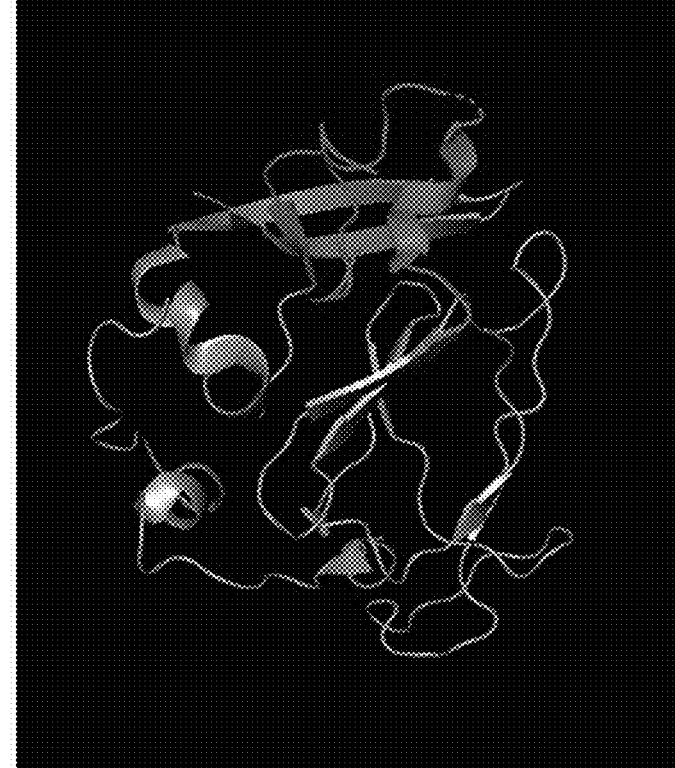
Figure 21:
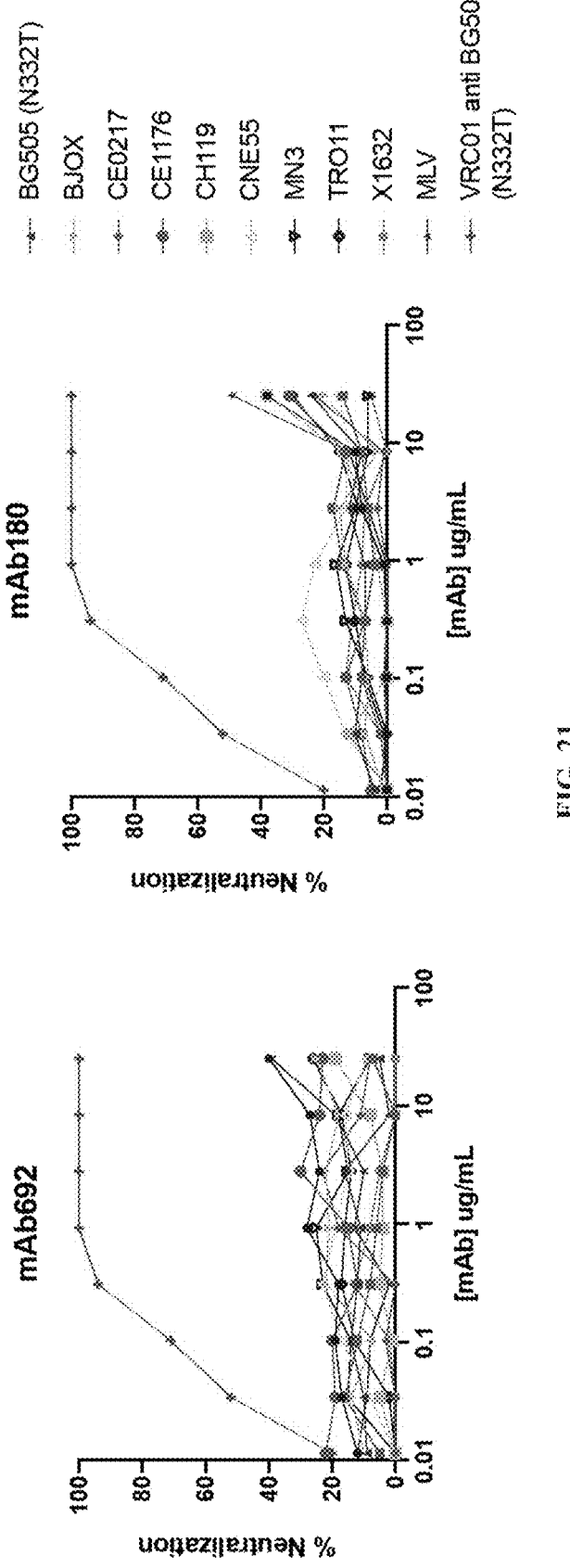
FIG. 21 shows that HIV/HCV cross-reactive mAbs are HIV non-neutralizing.
Figure 22:
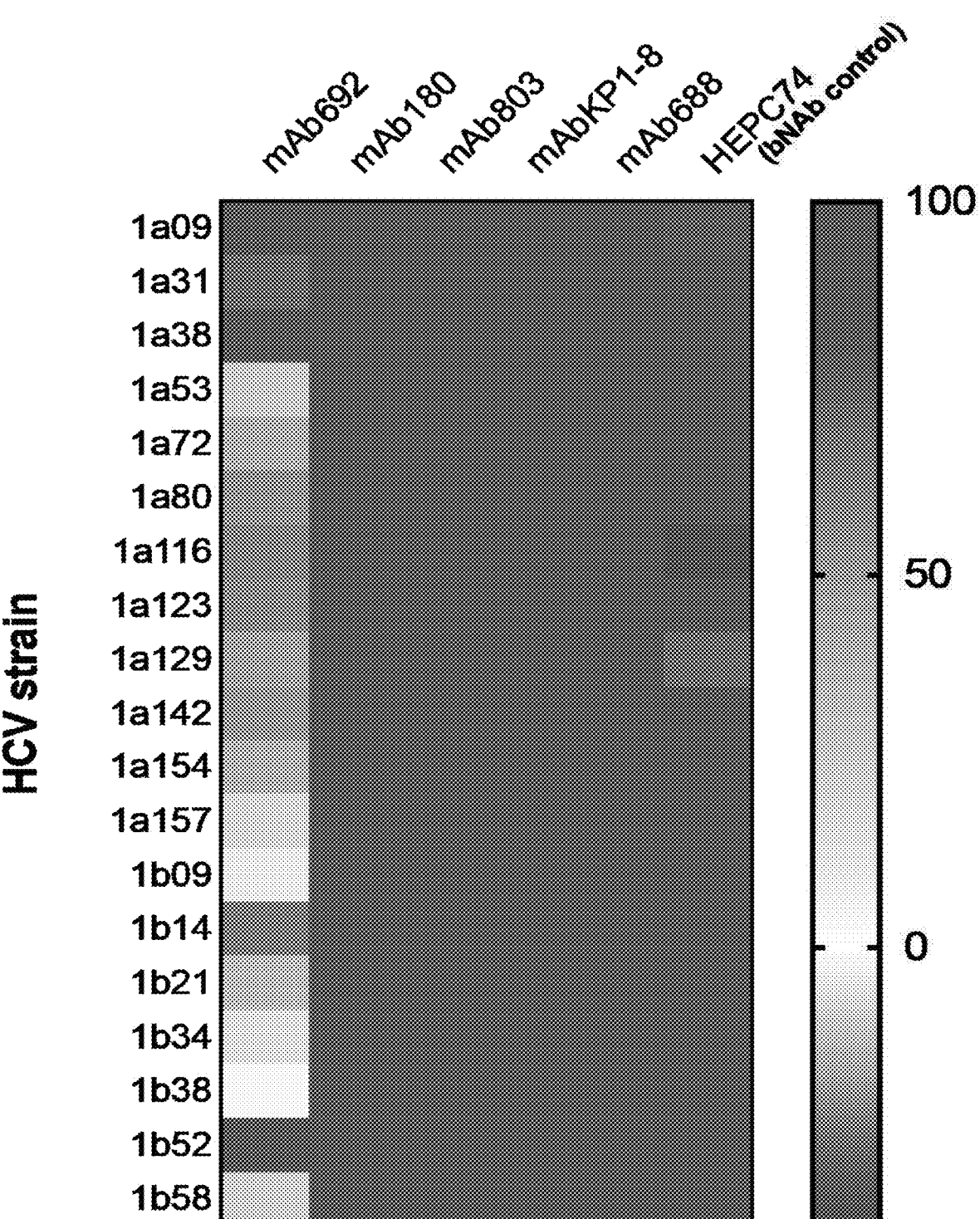
FIG. 22 shows that HIV/HCV cross-reactive mAbs show extraordinary neutralization breadth. HIV/HCV cross-reactive mAbs show superior neutralization breadth to HEPC74, previously the broadest neutralizing HCV antibody. The antibody was tested at 100 μg/ml.
Figure 23:
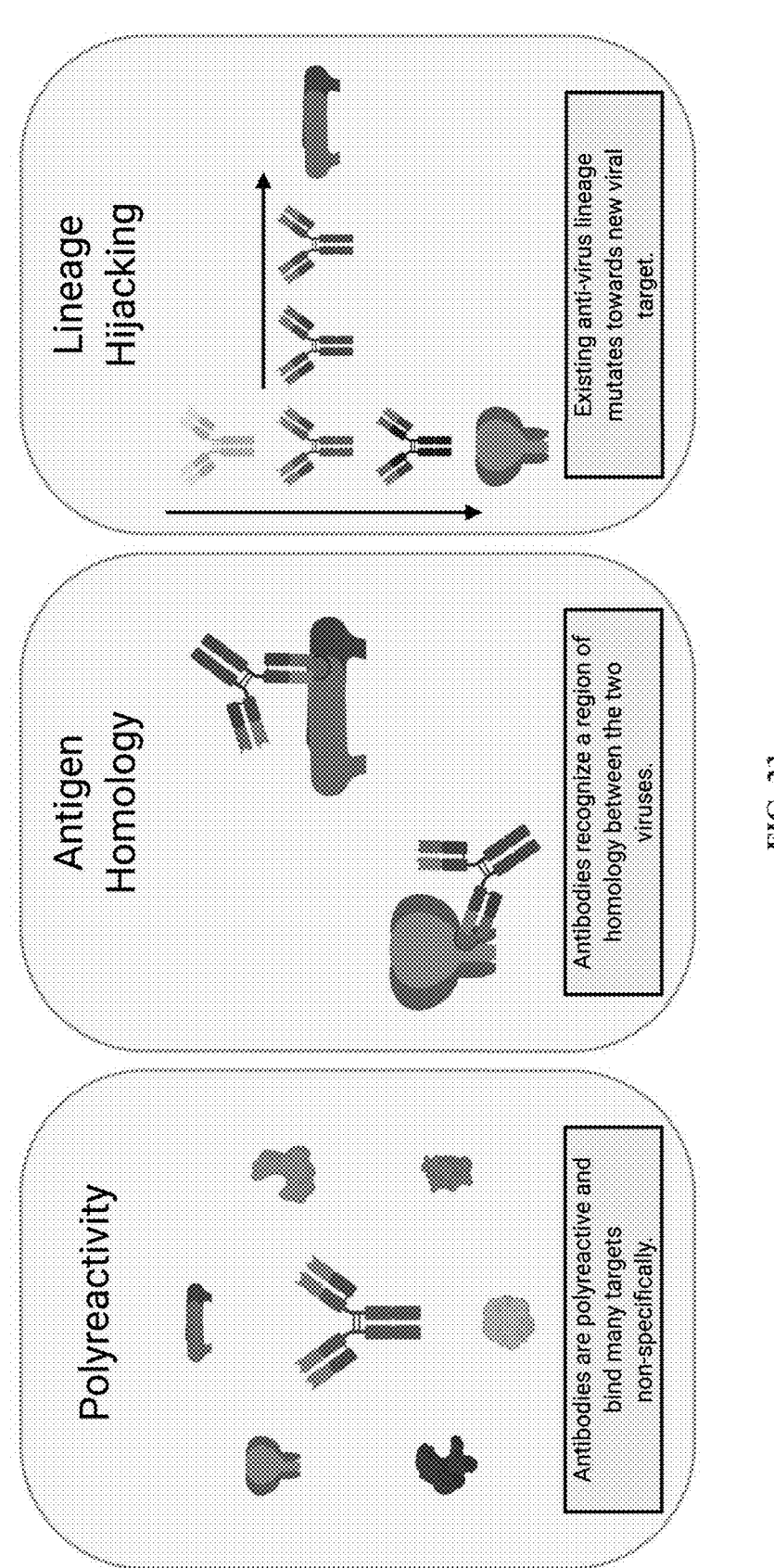
FIG. 23 shows how cross-reactivities can arise in HIV/HCV coinfection through polyreactivity, antigen homology, or lineage hijacking.
Figure 24A:
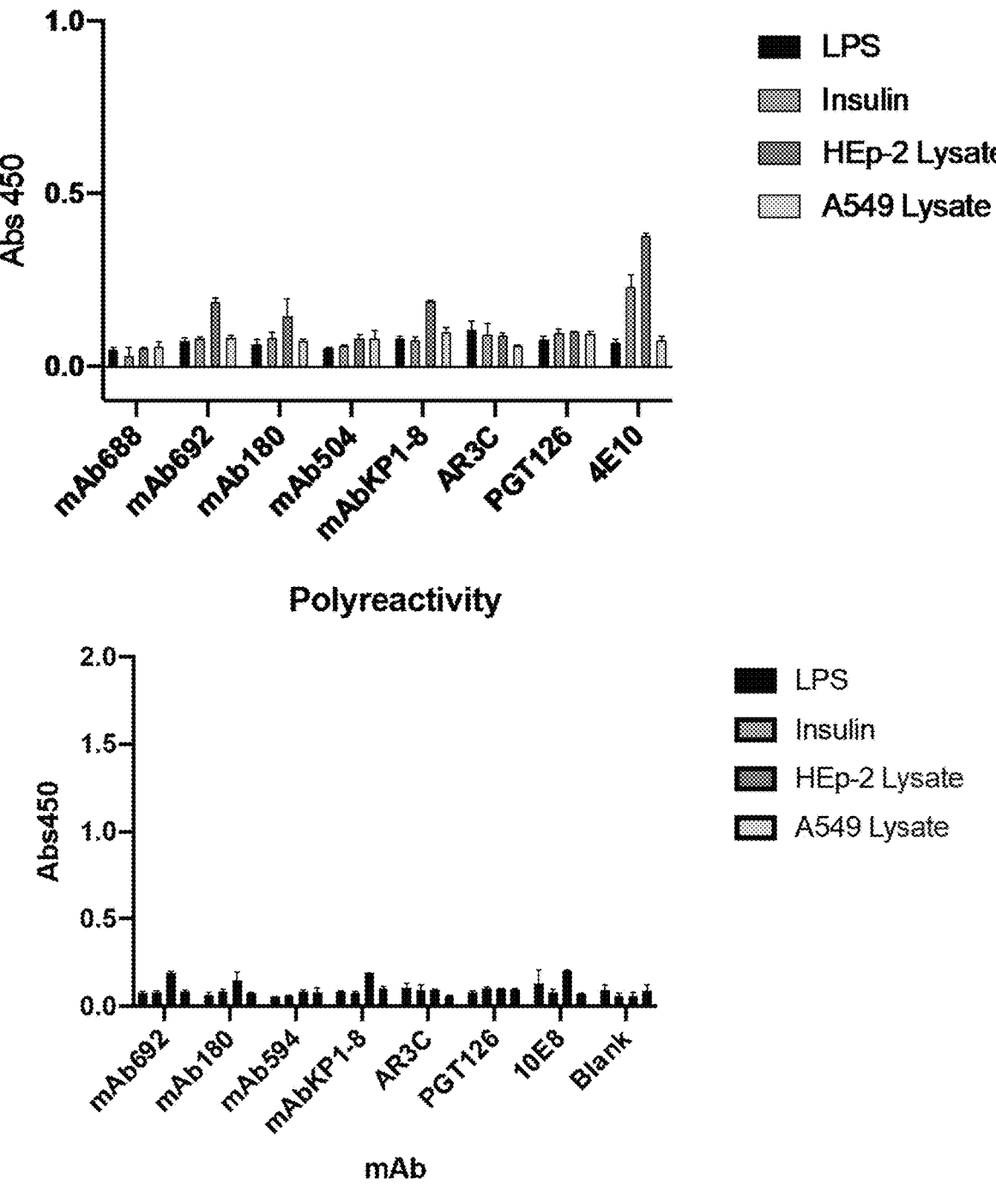
FIGS. 24A-24D depict that HIV/HCV cross-reactive mAbs show minimal polyreactivity.
Figure 24B:
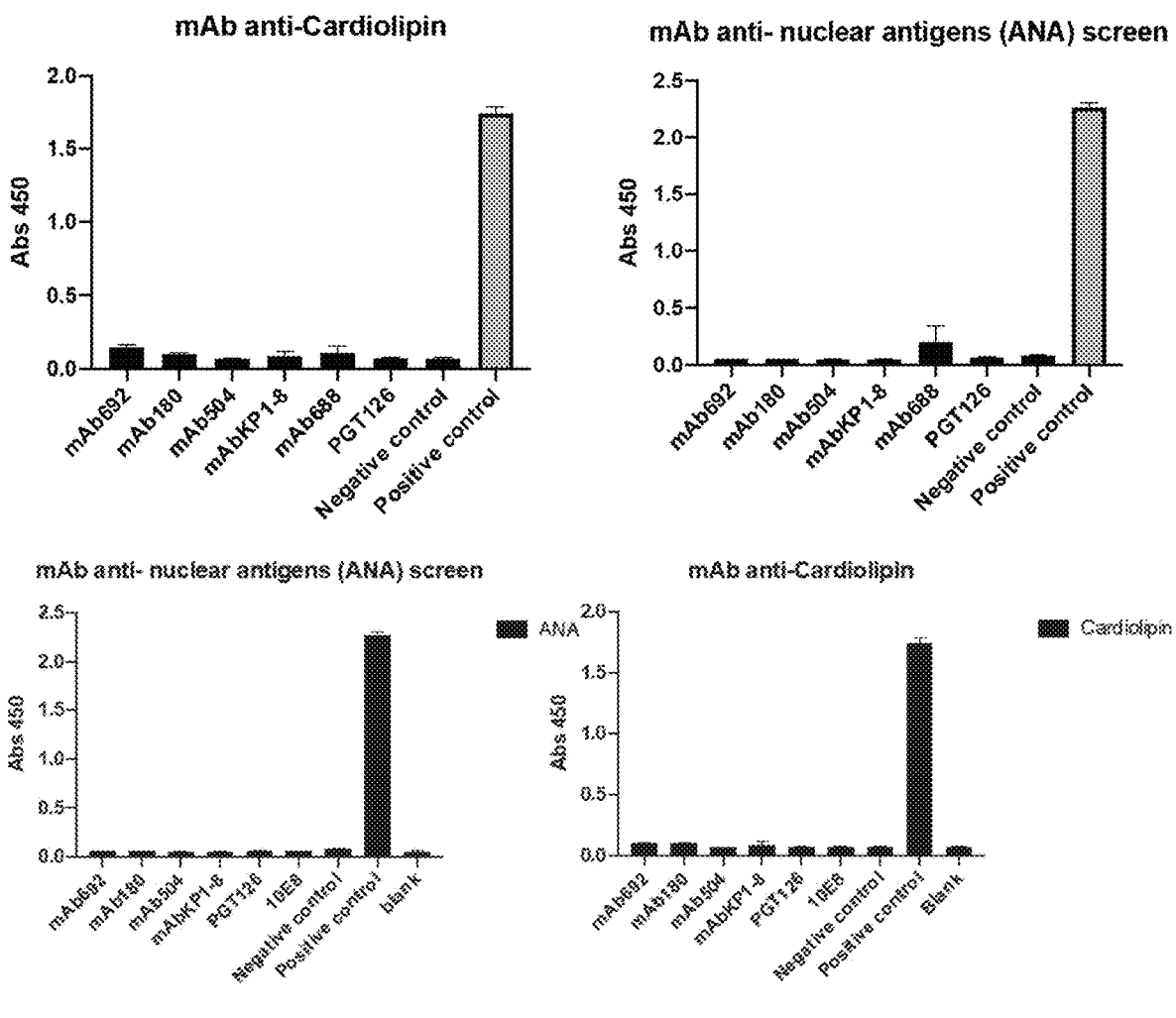
Figure 24C:
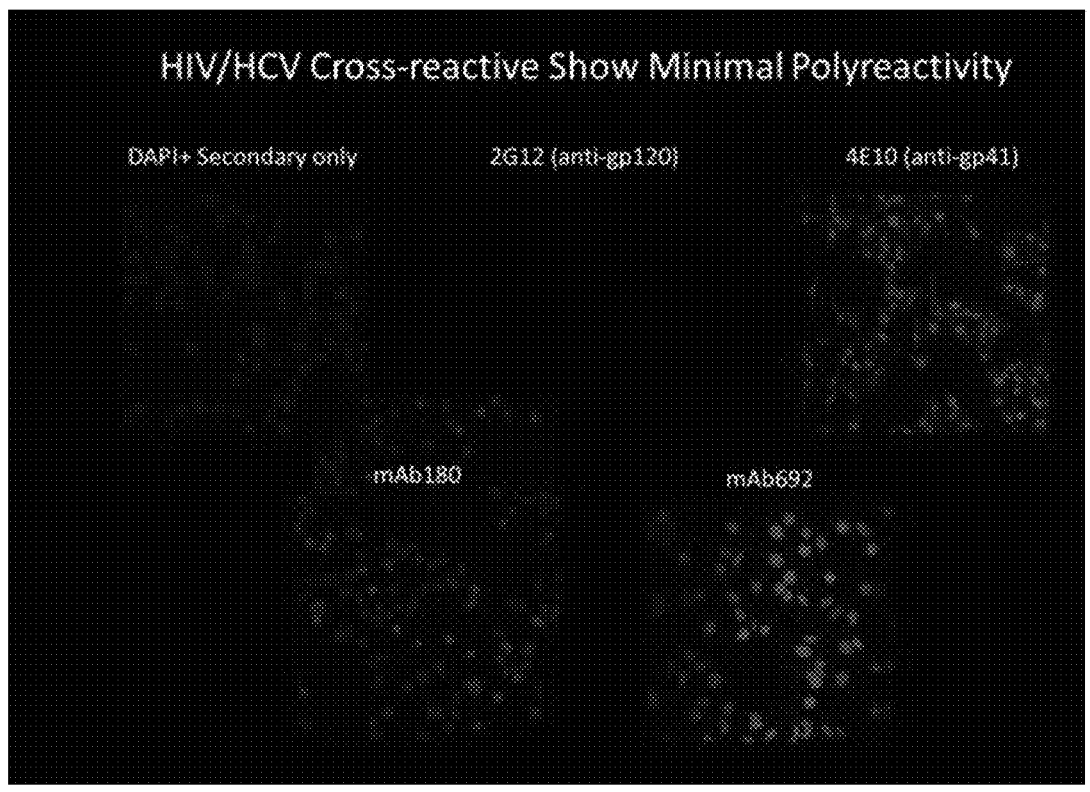
Figure 24D:
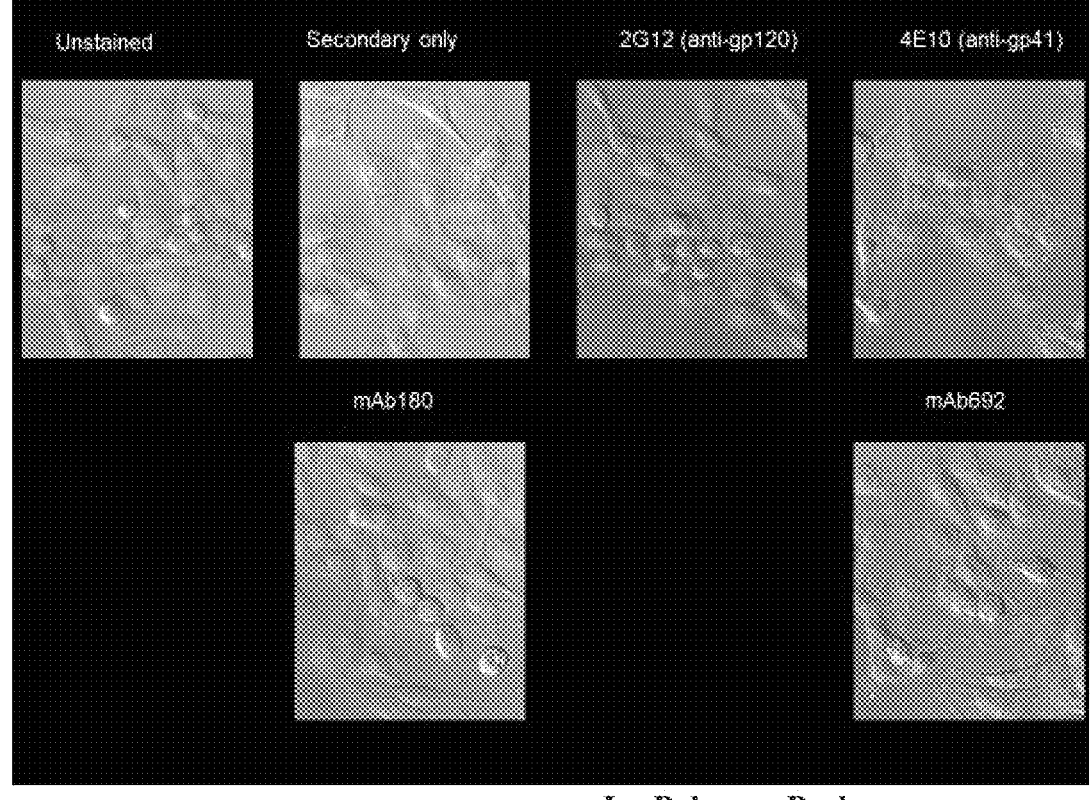
Figures 25, 26:
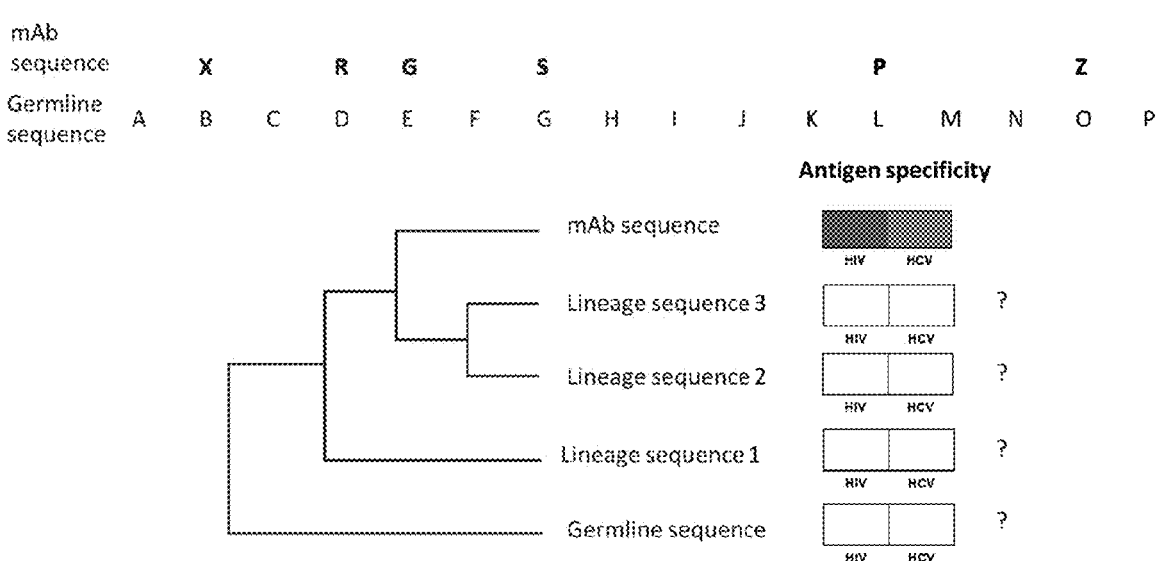
FIG. 25 shows tracing mutations and antigen specificity.
FIG. 26 shows that subsequent data was derived using a patient sample from a donor. Infection timepoints are shown. All antibody relative sequence data (not LIBRA-seq sequences) came from the Sep. 25, 2003 timepoint shown.

Samples were used from PTID: VC10014 (Vanderbilt cohort) taken 0.79 years post HIV infection (ypi) and 3.59ypi to isolate cross-reactive antibodies and begin characterizing their development using LIBRA-seq and unpaired deep sequencing (see approach). For LIBRA-seq a diverse panel of 4 HIV envelope glycoprotein antigens were used, each from a different viral clade (Clade A BG505 gp140 SOSIP, Clade B B41 gp140 SOSIP, Clade C ConC gp120 and recombinant circulating clade AE A244 gp120), and 3 HCV envelope antigens (Genotype 1a H77 E2 and E1E2, genotype 2a JFH-1 E2). Each antigen was labeled with a unique 15 nucleotide barcode and used to identify multiple, class-switched HIV/HCV cross-reactive B cells from the 3.39 ypi timepoint (FIG. 1). Expression of identified B cell receptors as recombinant antibodies confirmed their cross-reactivity against both HIV and HCV antigens. To trace the early development of identified HIV/HCV cross-reactive antibodies, PBMCs from 0.79ypi were sequenced and their maturations were inferred using phylogenetic analyses (FIG. 2). Taken together, these data demonstrate the identification of rare, HIV/HCV cross-reactive antibodies from a chronically co-infected cohort donor.

Example 2. Identifying Antibodies Recognizing HIV/HCV Co-Infection

A variety of techniques are utilized, including antigen-specific B-cell sorting, next-generation sequencing of antibody repertoires, and monoclonal antibody (mAb) functional validation assays.

The first step is performing antigen-specific B-cell sorting for two timepoints for each individual, which leads to the identification of antibodies that are reactive with each antigen. This step results in paired heavy/light chain sequences for antigen-specific antibodies against HIV and/or HCV. The next step is performing "deep" sequencing of the antibody repertoires for each timepoint, which allows the tracing of the lineage evolution for the antibodies identified in the antigen-specific sort (step 1). This step results in non-paired heavy and light chain sequences, but at a substantially greater sequencing depth than what is obtained in step 1. Clonal relative antibody sequences are expressed as recombinant antibodies to assess the effect of acquired somatic mutations over the course of chronic HIV/HCV co-infection on antigen specificity.

Example 3. Identifying Antigen-Specific Antibodies Using LIBRA-Seq in Co-Infected Individuals Samples are analyzed using a technology termed LIBRA-seq. This technology leverages DNA-barcoded antigens and a combination of antigen-specific B-cell sorting and single cell sequencing. After sequencing, antigen-specificity can be assigned to each single cell, along with B cell receptor sequence information, by mapping frequency of each antigen barcode. Further discussion of materials and methods for LIBRA-seq and for identifying paired heavy-light chain BCR sequences can also be found in WO2020033164, which is herein incorporated by reference in its entirety. For additional materials and methods, see WO2019/143884, which is herein incorporated by reference in its entirety.

Selection of antigen probes for sorting. The antigens that are used are forms of the Env glycoprotein from HIV-1 and the E1E2 glycoprotein from HCV, which have been identified as targets for neutralizing antibodies. A cocktail of antigen variants are used for each of HIV Env and HCV E1E2. The Env variants include trimeric gp140 stabilized in the closed prefusion conformation, and non-stabilized gp140, gp120, as well as MPER peptide; these constructs are in at least two different strain backgrounds (clade-A BG505 and clade-B B41). The HCV variants include E2 core as well as E1E2 heterodimer, from at least three strains (H77 [genotype 1a], J1 [genotype 2a], and HIC-109 [genotype 3a]). For HIV, all antigen variants are labeled with the same single color; similarly, all HCV antigen variants are labeled with the same single color (that is different from the HIV antigen color). About ten HIV and ten HCV antigens are used for sorting. The goal of including multiple different variants (a cocktail of antigens) for each pathogen is to capture a wider range of antigen-specific antibodies, in order to increase the amount of information obtained for the antigen-specific antibody repertoires. Using multiple antigen variants from multiple strains from each of the two pathogens also increases the chances of identifying antibodies with cross-reactivity between the two pathogens.

Antigen production. Recombinant soluble avi-tagged antigens are expressed in 293F or EXPI293™ mammalian cells using polyethylenimine (PEI) transfection reagent, and incubation for 5-7 days. Protein antigens are purified over an affinity column of agarose bound *Galanthus nivalis* lectin (Vector Laboratories cat no. AL-1243-5) at 4° C. Concentrated proteins are run on a SUPERDEX™ 200 Increase 10/300 GL or SUPEROSE™ 6 Increase 10/300 GL sizing column on an AKTA™ FPLC system. Fractions corresponding to correctly folded antigen are analyzed by SDS-PAGE, and antigenicity by ELISA is characterized with known mAbs specific for that antigen. Purified antigen proteins are biotinylated using BirA biotin ligase and conjugated to streptavidin-APC or streptavidin-PE for use in flow cytometry. Unique oligonucleotide barcodes are directly conjugated to each antigen using the SOLULINK® Protein-Oligonucleotide Conjugation Kit (TriLink cat no. S-9011) according to manufacturer's instructions. Antigen concentrations are estimated by BCA assay.

Antigen-specific B-cell sorting. PBMCs from the co-infected donors are stained with a panel of positive and negative cell markers to identify memory B cells, and with fluorescent antigen to identify virus-specific B cells. B cells are gated as CD3-CD14-IgM-IgG+CD19+ and antigen+. Both single virus and double virus-specific cells are sorted into complete RPMI for subsequent single cell sequencing.

Antibody sequence determination. Cells are bulk sorted for loading onto the CHROMIUM™ microfluidics device (10X Genomics) and processed using the B-cell VDJ solution according to manufacturer's instructions for a target capture of 10,000 B cells per ⅛ 10X cassette. Positive control cell lines (such as the VRC01 Ramon B cell line) can be spiked in to meet the 10X-recommended cell counts and to also provide an idea of efficacy and recovery. Briefly, B-cell populations of interest are sorted into complete RPMI (RPMI 1640+10% FBS) at a concentration of 300 cells/µL. Immediately after sorting, cells are pelleted for 5 minutes at 300×g using an ACCUSPIN™ Micro17 table-top centrifuge. The pellet is re-suspended in complete RPMI to 800-1200 cells/µL at a viability >90%. For library preparation, cells are partitioned into oil emulsions using a microfluidic circuit, enforcing one cell per reaction mixture. Upon lysis, NGS oligo adaptor sequences present on the oil emulsions capture messenger RNA from each cell. Following PCR amplification, V (D) J genes are further enhanced by targeted enrichment. The resulting cDNA is purified, and BCR and antigen barcode libraries are separated based on amplicon size. Resulting libraries are sequenced using the NOVASEQ 6000™ instrument, each donor sample run through the 10X technology is prepped separately and placed on separate lanes of a flow cell. Output fastq files are processed using Cell Ranger (10X Genomics) to assemble, quantify, and annotate paired V (D) J transcript sequences and antigen barcode counts on a cell-by-cell basis using 10X CHROMIUM™ cellular barcodes.

LIBRA-seq score determination. To define antigen-specificity, each cell is assigned a LIBRA-seq score for each antigen. This score is calculated by counting the number of antigen barcodes for each cell and calculating the centered-log ratio (CLR). Because the scale of counts for each antigen can differ, due to differential oligo loading during oligo-antigen conjugation, the CLR counts are rescaled using the StandardScaler method in scikit learn. This transformed and scaled number is defined as the LIBRA-seq score, which can then be used to compare antigen specificity across cell samples.

Example 4. Investigation of Antibodies from HIV/HCV Co-Infected Donors Using Non-Paired-Chain Antibody Sequencing The antigen-specific antibody sequence determination described above can result in sequence information for up to tens of thousands of B cells. As these are the first reported antibodies able to recognize diverse unrelated viruses, it is also important to understand how these complex specificities develop. To accomplish this, bulk non-paired heavy and light chain sequencing is performed for at least two timepoints for both donors (with no antigen-specific sorting), which results in millions of sequences per sample. Then, by matching clonal relatives from both the paired and non-paired sequencing datasets from multiple timepoints, the evolution of antigen-specific antibody lineages can be tracked at a substantially greater resolution.

PBMC samples are prepared for ILLUMINA™ sequencing using the ILLUMINA™ NEXTERA™ library preparation protocol. Whole cellular RNA is extracted using the RNEASY® kit (Qiagen), and reverse transcribed into cDNA using 5' RACE. The library is then amplified by several rounds of PCR, to include unique molecular identifiers (UMIs) and sequenced on an ILLUMINA™ HISEQ™ instrument, resulting in ~150 million reads/library. Library preparation is performed essentially as in Turchaninova, M. A. et al., 2016. Output FASTQ files from ILLUMINA™ sequencer are preprocessed using pRESTO. The PhyML is used to build and trace antibody lineages from the next-generation sequencing data.

Example 5. Development of Antibodies from HIV/HCV Co-Infected Donors mAbs are selected for further characterization to confirm their antigen specificity and function. The antibodies are characterized in various assays, including antigen binding, virus neutralization, and epitope mapping. These assessments provide insights into the functional role of the identified antigen-specific antibodies. Clonal relatives of these mAbs are selected for experimental validation to test the effect of acquired mutations in both the heavy and light chain sequences on antigen-specificity. For each donor, up to 5 HIV/HCV cross-reactive antibody lineages are selected, with up to three antibody representatives from each lineage for characterization. mAbs are characterized in various functional assays. These assays show the antigen specificity of the target antibodies, and also provide insights into how antibody affinity maturation contributes to acquired anti-pathogen functions.

mAb production. Selected antibody sequences are cloned custom expression vectors containing the heavy chain, kappa chain, or lambda chain signal sequence and constant region (Twist Bioscience). EXPI293™ cells are co-transfected with plasmids expressing matched pairs of heavy and light chain genes. Recombinant antibodies are purified on a protein A affinity column. Finally, antibodies are purified using a SUPERDEX™ 200 Increase 10/300 GL or SUPEROSE™ 6 Increase 10/300 GL sizing column on an AKTA™ FPLC system.

Binding assays. Standard ELISA techniques are used to measure binding of each isolated mAb to a representative panel of envelope proteins from various clades and genotypes. 2 µg/mL of each envelope glycoprotein construct is plated overnight on NUNC™ Immuno plates followed by blocking, and incubation with threefold serial dilutions of primary antibody starting at 20 µg/mL. Binding is detected by HRP-conjugated anti-human IgG secondary. Data are reported as absorbance at 450 nm.

The identification of HIV/HCV cross-reactive antibodies represents the identification of the first antibodies that cross-react with genetically unrelated viruses. Several mechanisms can explain antibody cross-reactivity between unrelated antigens. For examples, these cross-reactive antibodies can recognize epitopes of low-level structural similarity on the HIV and HCV envelope antigens (with low affinity for either antigen); or distinct antibody paratopes can utilize differential modes of binding to recognize each of the antigens. Furthermore, pre-existing memory B cells specific for a given antigen (e.g., HCV E2) can re-enter the developing antibody response against a new pathogen (e.g., HIV), a phenomenon that has been observed in other disease settings (e.g., malaria). A cross-reactive antibody lineage that was discovered at an early timepoint can evolve separate branches that gain increased specificity for one, and decreased specificity for the other, antigen.

Example 6. Diversion or Double-Edged Sword: Antibody Cross-Reactivity in HIV/HCV Co-Infection Investigating the human antibody response to HIV and HCV has led to significant advances towards preventative therapeutics and vaccines against these highly mutable pathogens. Yet, despite the high prevalence of HIV/HCV co-infection, little is known about antibody responses in this context. To address this deficit, the effect of chronic co-infection with HIV and HCV on the development of virus-specific humoral responses were investigated. To investigate this, LIBRA-seq (Linking B cell Receptor to Antigen specificity by Sequencing) was used, which is a technology recently developed that uses DNA-barcoded antigens to map B cell specificity through single-cell next-generation sequencing. Class-switched B cells that recognize viral envelope glycoproteins (HIV Env gp160, HCV E1E2) from a chronic HIV/HCV co-infected donor ~3.59 years post HIV infection (ypi) were investigated and multiple unique HIV/HCV cross-reactive B cells were identified. Their specificity was mapped as to a non-neutralizing on HIV gp41 and a neutralizing epitope on HCV E2 corresponding to antigenic region 5 (AR5) by PDB structural alignment, competition ELISA, overlapping peptide ELISA, and in vitro neutralization assay. Importantly, isolated cross-reactive antibodies show extraordinary HCV neutralization breadth, neutralizing 19/19 viruses tested (surpassing the broadest antibody previously tested in this panel, HEPC74, which neutralized 17/19 viruses). Deep sequencing from the same donor (0.79ypi) revealed multiple relatives of the cross-reactive antibodies, and their characterization by recombinant expression revealed that these HIV/HCV cross-reactive antibodies develop from a low-polyreactive, HCV-specific lineage that is hijacked after HIV infection, and subsequent somatic hypermutation leads to increased affinity for HIV. This study is the first to directly demonstrates that antibody lineages raised against one pathogen can enter the immune response against a different, genetically unrelated pathogen. Finally, the extraordinary anti-HCV capacity of identified antibodies indicate their use as therapeutics.

Example 7. Antibodies Recognizing HIV and HCV

Given the identification of potent virus-neutralizing antibodies against both HIV and HCV, antibodies present an attractive target for development of new therapeutic and prophylactic tools in the context of HIV/HCV co-infection. Very little is known, however, about antibodies in HIV/HCV co-infection. To address this question, disclosed herein is characterization of the antibody repertoires of two HIV/HCV co-infected individuals, for which there are samples from multiple timepoints (Table 1). This enables the identification of HIV-specific, HCV-specific, and HIV/HCV cross-reactive antibodies, and to follow their lineage development over time. These studies generate data related to antibody responses in HIV/HCV co-infection and use for therapeutic and vaccine utilization.

TABLE 1

| HIV/HCV co-infected donors in this study. | | | |
| --- | --- | --- | --- |
| Donor ID | Sex | # timepoints | ypi (HIV) |
| 10014 | M | 5 | ~0.5-3 |
| 10032 | F | 5 | 2-5 | ypi, years post-HIV infection.

The identified HIV/HCV cross-reactive antibodies are the first set of antibodies that can specifically cross-react with unrelated viral antigens. This is in contrast with two other settings: (a) antibodies that cross-react with antigens from related viruses (e.g., a cross-reactive antibody against RSV and hMPV), and (b) polyspecific antibodies that non-specifically react with many different antigens.

Antigen-specific B-cell sorting, next-generation sequencing of antibody repertoires, and monoclonal antibody functional validation assays are used to characterize these antibodies. For both donors, 5 timepoints are analyzed, ranging from ~0.5-3 and 2-5 years post-HIV infection, respectively. In both cases, both HIV and HCV infections are present at all five timepoints, which enables one to study the evolution of the antibody response during chronic co-infection. This work identifies and characterizes HIV-specific, HCV-specific, and HIV/HCV cross-reactive antibodies, and defines the evolution of the related antibody lineages over time.

The investigation comprises two steps. Step 1: Perform antigen-specific B-cell sorting for the first and last timepoints for each individual, which leads to the identification of antibodies that are reactive with each antigen. This step results in paired heavy/light chain sequences for antigen-specific antibodies against HIV and/or HCV. Step 2: Perform "deep" sequencing of the antibody repertoires for each timepoint, which allows the tracing of the lineage evolution for the antibodies identified in the antigen-specific sort (step 1). This step results in non-paired heavy and light chain sequences, but at a substantially greater sequencing depth than what is obtained in step 1. Matching non-paired (step 2) with paired (step 1) antibody sequences is done to obtain a detailed analysis of antibody lineage evolution.

Example 8. Identifying Antigen-Specific Antibodies in Co-Infected Individuals For each of the two co-infected donors in this example, samples from the first and last timepoints are analyzed for antigen-specific B cells by using a combination of antigen-specific B-cell sorting and sequencing techniques, resulting in paired heavy/light chain antibody sequence information.

Antigen-specific B-cell sorting. PBMCs from the co-infected donors are stained with a panel of positive and negative cell markers to identify memory B cells and stained with fluorescent antigen to identify virus-specific B cells. Positive B cells are gated as CD3-CD14-IgM-IgG+CD20+CD19+CD27+ and antigen+. The three populations that are analyzed further are: positive for either HIV antigens or for HCV antigens (single-positives), and positive for both (double-positives).

Selection of antigen probes for sorting. The antigens that are used are forms of the Env glycoprotein from HIV-1 and the E1E2 glycoprotein from HCV, which have been identified as targets for neutralizing antibodies. A cocktail of antigen variants are used for each of HIV Env and HCV E1E2. The Env variants include trimeric gp140 stabilized in the closed prefusion conformation, and non-stabilized gp140, gp120, as well as MPER peptide; these constructs are in at least two different strain backgrounds (clade-A BG505 and clade-B B41). The HCV variants include E2 core as well as E1E2 heterodimer, from at least three strains (H77 [genotype 1a], J1 [genotype 2a], and HIC-109 [genotype 3a]). For HIV, all antigen variants are labeled with the same single color; similarly, all HCV antigen variants are labeled with the same single color (that is different from the HIV antigen color). About ten HIV and ten HCV antigens are used for sorting. The goal of including multiple different variants (a cocktail of antigens) for each pathogen is to capture a wider range of antigen-specific antibodies, in order to increase the amount of information obtained for the antigen-specific antibody repertoires. Using multiple antigen variants from multiple strains from each of the two pathogens also increases the chances of identifying antibodies with cross-reactivity between the two pathogens. This is contrasted to other efforts in HIV antibody isolation, which have predominantly focused on identifying broadly neutralizing antibodies (bNAbs), which specifically aim to use stabilized trimers and avoid other antigen forms (such as non-stabilized gp140 or gp120) as antigen-specific probes. Since the assessments herein are not only limited to bNAbs, but rather to capture many different types of antigen-specific antibodies (irrespective of neutralization breadth), a cocktail of antigens is used. Using multiple antigen variants per pathogen also increases the number of antibodies with cross-reactivity.

Antibody sequence determination. 1) For the single-positives, cells are bulk sorted for loading onto the CHRO-MIUM™ microfluidics device (10X Genomics) and processed using the B-cell VDJ solution according to manufacturer's instructions for a target capture of 10,000 B cells per ⅛ 10X cassette. Positive control cell lines (such as the VRC01 Ramon B cell line) can be spiked in to meet the 10X-recommended cell counts and to also provide an idea of efficacy and recovery. Briefly, B-cell populations of interest are sorted into complete RPMI (RPMI 1640+10% FBS) at a concentration of 300 cells/μL. Immediately after sorting, cells are pelleted for 5 minutes at 300×g using an ACCUS- PIN™ Micro17 table-top centrifuge. The pellet is re-suspended in complete RPMI to 800-1200 cells/μL at a viability >90%. For library preparation, cells are partitioned into oil emulsions using a microfluidic circuit, enforcing one cell per reaction mixture. Upon lysis, NGS oligo adaptor sequences present on the oil emulsions capture messenger RNA from each cell. Following PCR amplification, V (D) J genes are further enhanced by targeted enrichment. The resulting cDNA is purified, and BCR and antigen barcode libraries are separated based on amplicon size. Resulting libraries are sequenced using the NOVASEQ 6000™ instrument, each donor sample run through the 10X technology is prepped separately and placed on separate lanes of a flow cell. Output fastq files are processed using Cell Ranger (10X Genomics) to assemble, quantify, and annotate paired V (D) J transcript sequences and antigen barcode counts on a cell-by-cell basis using 10X CHROMIUM™ cellular barcodes. 2) For the double positives, the cells are single-cell sorted in PCR plates containing lysis buffer, and the B-cell receptors (BCR) are amplified out of each cell, and cloned into a mammalian expression vector for recombinant production in 293F cells. BCR sequences are amplified out of single cells using a nested PCR approach, first using primers corresponding to the leader sequence and constant domains, and then with a primer mix for all VH and VL genes and reverse junction primers. In both cases, this process results in paired heavy/light chain sequence information for a set of antigen-specific antibodies (either single- or double-positive).

Step 2 of the non-paired-chain antibody sequencing is the same as that described in Example 3.

A six-months post-infection timepoint from donor 10014 (Table 1) was analyzed. For the antigen-specific B-cell sorting, the following antigens were used: (i) the "BG505 SOSIP" gp140 construct that is stabilized in the closed prefusion conformation of Env; and (ii) The "E2 core" protein, a truncated version of E2 that has been successfully crystallized, and that is known to bind a number of neutralizing antibodies isolated from HCV-infected donors. PBMCs from donor 10014 and separately from a non-infected control were stained with a panel of markers to identify memory B cells, and then stained with fluorescently labeled antigens (as described above) (FIGS. 62A and 62B). While B cells from the non-infected control did not bind the two antigens (FIG. 62A), a number of B cells that were single-positive for either antigen or double-positive for both antigens were identified (FIG. 62B).

Example 9. Monoclonal Antibody Production and Characterization

Monoclonal antibodies are further characterized for their antigen specificity and function. The antibodies are characterized in various assays, including antigen binding, virus neutralization, and epitope mapping.

For each donor, two lineages are selected each from the two single-positive (HIV or HCV) and the double-positive (HIV/HCV) populations, with up to three antibody representatives from each lineage.

Monoclonal antibody production. Selected antibody sequences are cloned into the expression vectors pFUSEss-CHIg-hG1 (heavy), pFUSE2ss-CLIg-hK (kappa light), and pFUSE2ss-CLIg-hL2 (lambda light). 293F cells are co-transfected with plasmids expressing matched pairs of heavy and light chain genes. Recombinant antibodies are purified on a protein A affinity column.

Binding assays. Standard ELISA techniques are used to measure binding of each isolated mAb to a representative panel of envelope proteins from various clades and geno-
types. 2 µg/mL of each envelope glycoprotein construct is
plated overnight on NUNC™ Immuno plates followed by
blocking, and incubation with threefold serial dilutions of
primary antibody starting at 20 µg/mL. Binding is detected
by HRP-conjugated anti-human IgG secondary. Data are
reported as absorbance at 450 nm.

Neutralization assays. To measure neutralization func-
tions of these monoclonal antibodies, the TZM-bl and the
HCVpp assays are used for HIV and HCV respectively,
which are standard in the field. Briefly, viral pseudoparticles
bearing envelope proteins are produced from diverse strains
and these viruses are incubated with serial dilutions of each
antibody. Antibody-pseudovirus mixtures are added to deficiency virus (HIV) envelope protein. B cells were iso-
lated from a co-infected individual using a flow cytometry
assay that measures the binding of B cells to the virus
envelope proteins. B cells that were able to bind both virus
envelope proteins were sorted into 96 well plates, lysed, and
reverse transcribed into cDNA. The B cell receptor
sequences were amplified out of the cDNA and sequenced
using Sanger sequencing through Genhunter (Nashville,
TN). The B cell receptor sequences were then cloned into
mammalian expression vectors for recombinant expression
in mammalian cells. The resulting antibodies were then
purified and tested for binding to the virus envelope proteins
using ELISA. These are the first identified antibodies to
recognize separate, diverse viruses.

TABLE 2

LIBRA-seq Identifies Multiple Unique HIV/HCV Cross-reactive Antibodies.
Sequences in Table: CARSEKRVTMTRKIKGRWFGPW (SEQ ID NO: 1822);
CARVAPPGVVNNKWFDIW (SEQ ID NO: 1821); CAAGLWSGDLSRPRYSDSW (SEQ ID
NO: 1817); CAKGLTTESRLEFW (SEQ ID NO: 1818); CVSSWGPESPYYFDYW (SEQ ID NO:
1819); CAREYCTGGDCHFFLDYW (SEQ ID NO: 1820); CQVWDSSSEHVVF (SEQ ID NO:
1888); CCLYAGSYSWVF (SEQ ID NO: 1887); CMQPLQLPDTF (SEQ ID NO: 1883);
CQQSYNVPTF (SEQ ID NO: 1884); CHQSSSLPFTF (SEQ ID NO: 1885); CQHFYSSPPTF
(SEQ ID NO: 1886).

| mAb name | IGHV gene | IGHJ gene | % SHM | CDR3 | IGLV gene | IGLI gene | % SHM | CDR3 |
|---|---|---|---|---|---|---|---|---|
| mAb180 | IGHV3-48 | IGHJ5 | 0.8877 | CARSEKRVTMTRKIKGRWFGPW | IGLV3-21 | IGLJ2 | 0.9283 | CQVWDSSSEHVVF |
| mAb692 | IGHV1-46 | IGHJ5 | 0.9132 | CARVAPPGVVNNKWFDIW | IGLV2-11 | IGLJ3 | 0.9028 | CCLVAGSYSWVF |
| mAb504 | IGHV3-15 | IGHJ4 | 0.8741 | CAAGLWSGDLSRPRYSDSW | IGKV2-28 | IGKJ4 | 0.9558 | CMWQPLQLPDTF |
| mAb688 | IGHV3-23 | IGHJ5 | 0.875 | CAKGLTTESRLEFW | IGKV1-39 | IGKJ1 | 0.8674 | CQQSYNVPTF |
| mAb803 | IGHV3-21 | IGHJ4 | 0.9514 | CVSSWGPESPVYFDYW | IGKV6-21 | IGKJ3 | 0.9642 | CHQSSSLPFTF |
| mAbKP1-8 | IGHV1-8 | IGHJ4 | 0.9028 | CAREYCTGGDCHFFLDYW | IGKV4-1 | IGKJ3 | 0.9327 | CQHFYSSPPTF |

TZM-bl or Huh-7 cell lines, and infectivity is measured by
a luciferase reporter in relative light units (RLU). Neutral-
ization is evaluated by ID50, here defined as the dilution at
which the antibody is able to inhibit 50% of the cells from
being infected. Established panels of twelve and six diverse
strains are used for the neutralization assays with HIV and
HCV, respectively, to determine overall neutralization
breadth for the tested antibodies.

Epitope mapping. Standard mapping techniques are
applied, such as binding competition with monoclonal anti-
bodies, neutralization or binding of Env variants containing
epitope-specific knockout mutations, and neutralization
blocking by epitope-specific antigens. In addition, the neu-
tralization fingerprint (NFP) epitope mapping approach is
used.

This study results in the identification and characteriza-
tion of antibodies that are specific to HIV or HCV, or
antibodies that are cross-reactive. The analysis of multiple
timepoints for each donor provides insights into the evolu-
tion of the antibody response to each virus. This large-scale
sequencing data allows the generation of detailed lineages of
antigen-specific antibodies. Hence, lineage sequence analy-
sis can determine properties such as CDR3 length and
physicochemical composition, somatic hypermutation dis-
tributions, numbers of antibody lineage members, etc. Such
assessments can compare and identify similarities and dif-
ferences between HIV-specific vs. HCV-specific lineages,
and determine how these change over time.

Disclosed herein are antibodies that can bind both Hepa-
titis C virus (HCV) envelope protein and Human Immuno- Sequences A large number of sequences were analyzed throughout
this application. Additional sequences reviewed and ana-
lyzed include:

SEQ ID NOs: 1905-2627 which are "Barcode" sequences;

SEQ ID NOs: 2628-3258 which are "SEQUENCE_
VDJ.H" sequences;

SEQ ID NOs: 3259-3880 which are "JUNCTION.H"
sequences;

SEQ ID NOs: 7771-8518 which are "SEQUENCE_
VDJ.L" sequences;

SEQ ID NOs: 8520-9189 which are "JUNCTION.L"
sequences.

Unless defined otherwise, all technical and scientific
terms used herein have the same meanings as commonly
understood by one of skill in the art to which the disclosed
invention belongs. Publications cited herein and the mate-
rials for which they are cited are specifically incorporated by
reference.

Those skilled in the art will appreciate that numerous
changes and modifications can be made to the preferred
embodiments of the invention and that such changes and
modifications can be made without departing from the spirit
of the invention. It is, therefore, intended that the appended
claims cover all such equivalent variations as fall within the
true spirit and scope of the invention.

SEQUENCE LISTING

The patent contains a lengthy sequence listing. A copy of the sequence listing is available in electronic form from the USPTO web site (https://seqdata.uspto.gov/docdetail?docId=US12624091B2). An electronic copy of the sequence listing will also be available from the USPTO upon request and payment of the fee set forth in 37 CFR 1.19(b)(3).

What is claimed is:

1. A recombinant antibody for binding both Human Immunodeficiency virus (HIV) and Hepatitis C virus (HCV), said antibody comprising a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

(i) CDRH1 is SEQ ID NO: 13107, CDRH2 is SEQ ID NO: 13113, CDRH3 is SEQ ID NO: 110 or 1822, CDRL1 is SEQ ID NO: 13125, CDRL2 is SEQ ID NO: 13131, and CDRL3 is SEQ ID NO: 101 or 1888;

(ii) CDRH1 is SEQ ID NO: 13106, CDRH2 is SEQ ID NO: 13112, CDRH3 is SEQ ID NO: 104 or 1821, CDRL1 is SEQ ID NO: 13124, CDRL2 is SEQ ID NO: 13130, and CDRL3 is SEQ ID NO: 88 or 1887;

(iii) CDRH1 is SEQ ID NO: 13102, CDRH2 is SEQ ID NO: 13108, CDRH3 is SEQ ID NO: 1817, CDRL1 is SEQ ID NO: 13120, CDRL2 is SEQ ID NO: 13126, and CDRL3 is SEQ ID NO: 13 or 1883;

(iv) CDRH1 is SEQ ID NO: 13103, CDRH2 is SEQ ID NO: 13109, CDRH3 is SEQ ID NO: 1818, CDRL1 is SEQ ID NO: 13121, CDRL2 is SEQ ID NO: 13127, and CDRL3 is SEQ ID NO: 25 or 1884;

(v) CDRH1 is SEQ ID NO: 13104, CDRH2 is SEQ ID NO: 13110, CDRH3 is SEQ ID NO: 1819, CDRL1 is SEQ ID NO: 13122, CDRL2 is SEQ ID NO: 13128, and CDRL3 is SEQ ID NO: 39 or 1885; or (vi) CDRH1 is SEQ ID NO: 13105, CDRH2 is SEQ ID NO: 13111, CDRH3 is SEQ ID NO: 1820, CDRL1 is SEQ ID NO: 13123, CDRL2 is SEQ ID NO: 13129, and CDRL3 is SEQ ID NO: 49 or 1886.

2. The recombinant antibody of claim 1, wherein the VL comprises an amino acid sequence selected from SEQ ID NOs: 119, 227, 242, 351, 1399, 1406, and 1899-1904.

3. The recombinant antibody of claim 1, wherein the VH comprises an amino acid sequence selected from the group consisting of SEQ ID NOs: 1694-1756.

4. The recombinant antibody of claim 1, wherein the VH comprises an amino acid sequence selected from the group consisting of SEQ ID NOs: 1895-1898, 1694, and 1718.

5. A method of treating a HIV/HCV co-infection comprising administering to a subject a therapeutically effective amount of the recombinant antibody of claim 1.

6. A method of treating an HIV infection comprising administering to a subject a therapeutically effective amount of the recombinant antibody of claim 1.

7. A method of treating an HCV infection comprising administering to a subject a therapeutically effective amount of the recombinant antibody of claim 1.

8. The recombinant antibody of claim 1, wherein CDRH1 is SEQ ID NO: 13107, CDRH2 is SEQ ID NO: 13113, CDRH3 is SEQ ID NO: 110 or 1822, CDRL1 is SEQ ID NO: 13125, CDRL2 is SEQ ID NO: 13131, and CDRL3 is SEQ ID NO: 101 or 1888.

9. The recombinant antibody of claim 8, wherein the VH comprises SEQ ID NO: 1718, or an amino acid sequence at least 60% identical thereto, and wherein the VL comprises SEQ ID NO: 1406, or an amino acid sequence at least 60% identical thereto.

10. The recombinant antibody of claim 1, wherein CDRH1 is SEQ ID NO: 13106, CDRH2 is SEQ ID NO: 13112, CDRH3 is SEQ ID NO: 104 or 1821, CDRL1 is SEQ ID NO: 13124, CDRL2 is SEQ ID NO: 13130, and CDRL3 is SEQ ID NO: 88 or 1887.

11. The recombinant antibody of claim 10, wherein the VH comprises SEQ ID NO: 1694, or an amino acid sequence at least 60% identical thereto, and wherein the VL comprises SEQ ID NO: 1399 or 1903, or an amino acid sequence at least 60% identical thereto.

12. The recombinant antibody of claim 1, wherein CDRH1 is SEQ ID NO: 13102, CDRH2 is SEQ ID NO: 13108, CDRH3 is SEQ ID NO: 1817, CDRL1 is SEQ ID NO: 13120, CDRL2 is SEQ ID NO: 13126, and CDRL3 is SEQ ID NO: 13 or 1883.

13. The recombinant antibody of claim 12, wherein the VH comprises SEQ ID NO: 1895, or an amino acid sequence at least 60% identical thereto, and wherein the VL comprises SEQ ID NO: 1899, or an amino acid sequence at least 60% identical thereto.

14. The recombinant antibody of claim 1, wherein CDRH1 is SEQ ID NO: 13103, CDRH2 is SEQ ID NO: 13109, CDRH3 is SEQ ID NO: 1818, CDRL1 is SEQ ID NO: 13121, CDRL2 is SEQ ID NO: 13127, and CDRL3 is SEQ ID NO: 25 or 1884.

15. The recombinant antibody of claim 14, wherein the VH comprises SEQ ID NO: 1896, or an amino acid sequence at least 60% identical thereto, and wherein the VL comprises SEQ ID NO: 1900, or an amino acid sequence at least 60% identical thereto.

16. The recombinant antibody of claim 1, wherein CDRH1 is SEQ ID NO: 13104, CDRH2 is SEQ ID NO: 13110, CDRH3 is SEQ ID NO: 1819, CDRL1 is SEQ ID NO: 13122, CDRL2 is SEQ ID NO: 13128, and CDRL3 is SEQ ID NO: 39 or 1885.

17. The recombinant antibody of claim 16, wherein the VH comprises SEQ ID NO: 1897, or an amino acid sequence at least 60% identical thereto, and wherein the VL comprises SEQ ID NO: 1901, or an amino acid sequence at least 60% identical thereto.

18. The recombinant antibody of claim 1, wherein CDRH1 is SEQ ID NO: 13105, CDRH2 is SEQ ID NO: 13111, CDRH3 is SEQ ID NO: 1820, CDRL1 is SEQ ID NO: 13123, CDRL2 is SEQ ID NO: 13129, and CDRL3 is SEQ ID NO: 49 or 1886.

19. The recombinant antibody of claim 18, wherein the VH comprises SEQ ID NO: 1898, or an amino acid sequence at least 60% identical thereto, and wherein the VL comprises SEQ ID NO: 1902, or an amino acid sequence at least 60% identical thereto.

* * * * *